US012718006B2

(12) United States Patent
Potts et al.

(10) Patent No.: US 12,718,006 B2
(45) Date of Patent: Aug. 25, 2026

(54) METHODS, APPARATUS AND SYSTEMS FOR ANNOTATION OF TEXT DOCUMENTS

(71) Applicant: PAREXEL International, LLC, Waltham, MA (US)

(72) Inventors: Christopher Potts, Palo Alto, CA (US); Evan Lin, San Francisco, CA (US); Andrew Maas, Redwood City, CA (US); Abhilash Itharaju, Fremont, CA (US); Kevin Reschke, San Mateo, CA (US); Jordan Vincent, San Francisco, CA (US)

(73) Assignee: PAREXEL International, LLC, Newton, MA (US)

( * ) Notice: Subject to any disclaimer, the term of this patent is extended or adjusted under 35 U.S.C. 154(b) by 238 days.

(21) Appl. No.: 18/667,852

(22) Filed: May 17, 2024

(65) Prior Publication Data

US 2025/0021748 A1 Jan. 16, 2025

Related U.S. Application Data

(63) Continuation of application No. 17/578,390, filed on Jan. 18, 2022, now Pat. No. 12,014,135, which is a (Continued)

(51) Int. Cl.

*G06F 40/169* (2020.01)
*G06F 3/04842* (2022.01)
*G16H 10/60* (2018.01)

(52) U.S. Cl.

CPC ........ *G06F 40/169* (2020.01); *G06F 3/04842* (2013.01); *G16H 10/60* (2018.01)

(58) Field of Classification Search

CPC .. G06F 40/169; G06F 3/04842; G06F 40/151; G16H 10/60; G16H 50/20; G16H 15/00
See application file for complete search history.

(56) References Cited

U.S. PATENT DOCUMENTS 5,450,535 A 9/1995 North
8,423,523 B2 4/2013 Vergnory-Mion et al.
(Continued)

FOREIGN PATENT DOCUMENTS

EP 1361522 A2 11/2003
JP 2009-259250 A 11/2009
(Continued)

OTHER PUBLICATIONS

Extended European Search Report dated Nov. 9, 2022 in connection with European Application No. 20770117.8.
(Continued)

*Primary Examiner* — Pei Yong Weng
(74) *Attorney, Agent, or Firm* — Wolf, Greenfield & Sacks, P.C.

(57) ABSTRACT

Methods and apparatus to facilitate annotation projects to extract structured information from free-form text using NLP techniques. Annotators explore text documents via automated preannotation functions, flexibly formulate annotation schemes and guidelines, annotate text, and adjust annotation labels, schemes and guidelines in real-time as a project evolves. NLP models are readily trained on iterative annotations of sample documents by domain experts in an active learning workflow. Trained models are then employed to automatically annotate a larger body of documents in a project dataset. Experts in a variety of domains can readily develop an annotation project for a specific use-case or business question. In one example, documents relating to the health care domain are effectively annotated and employed to train sophisticated NLP models that provide valuable insights regarding many facets of health care. In another example, annotation methods are enhanced by utilizing domain-specific information derived from a novel knowledge graph architecture.

20 Claims, 48 Drawing Sheets

Related U.S. Application Data continuation of application No. 16/815,873, filed on Mar. 11, 2020, now Pat. No. 11,263,391.

(60) Provisional application No. 62/816,596, filed on Mar. 11, 2019.

(56) References Cited

U.S. PATENT DOCUMENTS

| | | | |
|---|---|---|---|
| 8,452,851 | B2 | 5/2013 | Kabiljo et al. |
| 8,996,555 | B2 | 3/2015 | Kuchmann-Beauger et al. |
| 9,910,903 | B1 | 3/2018 | Jilani et al. |
| 10,191,734 | B1 | 1/2019 | Totale et al. |
| 10,262,030 | B1 | 4/2019 | Burtenshaw et al. |
| 10,713,252 | B1 | 7/2020 | Bourne et al. |
| 10,878,000 | B2 | 12/2020 | Vaquero Gonzalez et al. |
| 11,263,391 | B2 | 3/2022 | Potts et al. |
| 11,507,629 | B2 | 11/2022 | Dingwall et al. |
| 11,657,044 | B2 | 5/2023 | Reschke et al. |
| 12,014,135 | B2 | 6/2024 | Potts et al. |
| 2003/0149685 | A1 | 8/2003 | Trossman et al. |
| 2003/0212544 | A1 | 11/2003 | Acero et al. |
| 2005/0027664 | A1 | 2/2005 | Johnson et al. |
| 2005/0090911 | A1 | 4/2005 | Ingargiola et al. |
| 2005/0262081 | A1 | 11/2005 | Newman |
| 2005/0273730 | A1 | 12/2005 | Card et al. |
| 2006/0036568 | A1 | 2/2006 | Moore et al. |
| 2006/0248045 | A1 | 11/2006 | Toledano et al. |
| 2007/0106499 | A1 | 5/2007 | Dahlgren et al. |
| 2008/0213768 | A1 | 9/2008 | Cai et al. |
| 2011/0252355 | A1 | 10/2011 | Nixon et al. |
| 2011/0264291 | A1 | 10/2011 | Le Roux et al. |
| 2011/0295788 | A1 | 12/2011 | Kowalski |
| 2012/0072468 | A1 | 3/2012 | Anthony et al. |
| 2012/0221558 | A1 | 8/2012 | Byrne et al. |
| 2012/0246153 | A1 | 9/2012 | Pehle |
| 2012/0259895 | A1 | 10/2012 | Neely, III et al. |
| 2013/0151572 | A1 | 6/2013 | Brocato et al. |
| 2013/0191718 | A1 | 7/2013 | Luke |
| 2013/0262449 | A1 | 10/2013 | Arroyo et al. |
| 2013/0262501 | A1 | 10/2013 | Kuchmann-Beauger et al. |
| 2013/0332438 | A1 | 12/2013 | Li et al. |
| 2014/0059084 | A1 | 2/2014 | Adams et al. |
| 2014/0098101 | A1 | 4/2014 | Friedlander et al. |
| 2014/0136520 | A1 | 5/2014 | Digana |
| 2014/0214834 | A1 | 7/2014 | Ozonat et al. |
| 2014/0222826 | A1 | 8/2014 | DaCosta et al. |
| 2014/0236579 | A1 | 8/2014 | Kurz |
| 2014/0244325 | A1 | 8/2014 | Cartwright |
| 2014/0258301 | A1 | 9/2014 | Misra et al. |
| 2014/0337306 | A1 | 11/2014 | Gramatica |
| 2015/0095303 | A1 | 4/2015 | Sonmez et al. |
| 2015/0117216 | A1 | 4/2015 | Anand et al. |
| 2015/0127677 | A1 | 5/2015 | Wang et al. |
| 2015/0161521 | A1 | 6/2015 | Shah et al. |
| 2015/0324425 | A1 | 11/2015 | Behzadi et al. |
| 2015/0350440 | A1 | 12/2015 | Steiner et al. |
| 2015/0370787 | A1 | 12/2015 | Akbacak et al. |
| 2016/0117322 | A1 | 4/2016 | Ramaswamy et al. |
| 2016/0117752 | A1 | 4/2016 | Chacko et al. |
| 2016/0162456 | A1 | 6/2016 | Munro et al. |
| 2016/0162458 | A1 | 6/2016 | Munro et al. |
| 2016/0179877 | A1 | 6/2016 | Koerner et al. |
| 2016/0267128 | A1 | 9/2016 | Dumoulin et al. |
| 2016/0275196 | A1 | 9/2016 | Lee et al. |
| 2016/0311113 | A1 | 10/2016 | Markey et al. |
| 2017/0249309 | A1 | 8/2017 | Sarikaya |
| 2017/0270418 | A1 | 9/2017 | Reschke et al. |
| 2017/0277841 | A1 | 9/2017 | Shankar et al. |
| 2017/0308620 | A1 | 10/2017 | Cao et al. |
| 2018/0075359 | A1 | 3/2018 | Brennan et al. |
| 2018/0081937 | A1 | 3/2018 | Broecheler |
| 2018/0121500 | A1 | 5/2018 | Rescchke et al. |
| 2018/0121546 | A1 | 5/2018 | Dingwall et al. |
| 2019/0034591 | A1 | 1/2019 | Mossin et al. |
| 2020/0293712 | A1 | 9/2020 | Potts et al. |
| 2021/0191924 | A1 | 6/2021 | Reschke et al. |
| 2022/0129766 | A1 | 4/2022 | Potts et al. |
| 2022/0253594 | A1 | 8/2022 | Potts et al. |

FOREIGN PATENT DOCUMENTS

| | | |
|---|---|---|
| JP | 2011-501847 A | 1/2011 |
| JP | 2018-060529 A | 4/2018 |

OTHER PUBLICATIONS

International Search Report and Written Opinion mailed Jun. 15, 2020 in connection with International Application No. PCT/US2020/022107.

Japanese Office Action dated Apr. 30, 2024 in connection with Japanese Application No. 2021-555078.

[No Author Listed], Data modeling. Wikipedia. Oct. 2018. 8 pages. URL:https://en.wikipedia.org/wiki/data_modeling [last accessed Dec. 14, 2018].

[No Author Listed], Transform Complex Text Documents into Data, Insights, & Value. 2022, 12 pages. URL:https://www.lexalytics.com [last accessed Aug. 15, 2022].

Eifrem, How Graph Search Works. Jun. 13, 2013. 2 pages. URL:https://neo4j.com/news/how-graph-search-works.

Forest et al., Dedupe. 2022, 5 pages. URL:https://github.com/datamade/dedupe. [last accessed Apr. 7, 2022].

Gawriljuk et al., A scalable approach to incrementally building knowledge graphs. International conference on theory and practice of digital libraries. Sep. 2016, pp. 188-199.

Kaufmann et al., Evaluating the usability of natural language query languages and interfaces to Semantic Web knowledge bases. Journal of Web Semantics. Nov. 2010;8(4):377-93. DOI:10.1016/j.websem.2010.06.001.

Li et al., Under the hood: The natural language interface of Graph Search. Apr. 29, 2013. 9 pages. URL:https://code.facebook.com/posts/316353631844205/under-the-hood-the-natural-language-interface-of-graph-search [last accessed Apr. 7, 2022].

Park et al., Introducing: Project open data. May 16, 2013. 3 pages. URL:https://www.whitehouse.gov/blog/2013/05/16/introducing-project-open-data [last accessed Apr. 7, 2022].

Reddy et al., Large-scale semantic parsing without question-answer pairs. Transactions of the Association for Computational Linguistics. Dec. 1, 2014;2:377-92.

Rui et al., Visualization and Forecast Analysis of Science and Technology Intelligence Based on Knowledge Graph. 2018 17th International Symposium on Distributed Computing and Applications for Business Engineering and Science (DCABES). Oct. 2018, pp. 44-47.

Setia, Create a knowledge base using domain specific documents and the mammoth python library. Jun. 17, 2018. 6 pages. URL:http://web.archive.org/web/20180617181315/https://github.com/IBM/build-knowledge-base-with-domain-specific-documents [last accessed Jul. 27, 2022].

Stichbury, WTF is a knowledge graph? Hacker Noon. May 10, 2017. 10 pages. URL:https://hackernoon.com/wtf-is-a-knowledge-graph-a16603a1a25f [last accessed Nov. 17, 2018].

Sun et al., Data Processing and Text Mining Technologies on Electronic Medical Records: A Review. Hindawi. Journal of Healthcare Engineering. Apr. 2018. 10 pages. URL:https://www.hindawi.com/journals/jhe/2018/4302425 [last accessed Aug. 15, 2022].

Yankova, Text Mining & Graph Databases—Two Technologies that Work Well Together. Jul. 5, 2014. 7 pages. URL:https://www.ontotext.com/blog/text-mining-graph-databases-work-well-together [last accessed Aug. 15, 2022].

Zaki et al., Knowledge graph construction and search for biological databases. 2017 International Conference on Research and Innovation in Information Systems (ICRIIS). Jul. 2017, pp. 1-6.

Japanese Office Action dated Oct. 14, 2025 in connection with Japanese Application No. 2024-202391.

FIG. 12
1100A
1128
Back
Annotation Scheme
1120A
Edit
View Guidelines
Spans
1102A
Drug
1102aA
Subject
1102bA
Adverse Drug Event
1102cA
Drug Effective
1102dA
Drug Ineffective
1102eA
Contributing Factor
1102fA
Relations
1104A
has_ADE: Drug → Adverse Drug Event
1104aA
has_contributing_factor: Adverse Drug...
1104bA
is_effective: Drug → Drug Effective
1104cA
not_effective: Drug → Drug Ineffective
1104dA
Tags
Case Report
Non-Clinical Study
Observational Study
Randomized Controlled Trial
Review/Meta-Analysis
Previous
2 of 200
Next
Completed
concentration of methionine. Further DNA sequencing
analysis showed 665C&gt;T homozygous mutations in the
MTHFR gene. The patient was diagnosed with MTHFR
deficiency-associated schizophrenia and treatment with
Drug
1110A
1110B
1110C
and
1110D
was initiated.
Drug Effective
1112A
After 3 months of treatment, the
patient returned to school. He is now living with normal
school life. In summary, children with late-onset MTHFR
deficiency and secondary cerebral folate deficiency may
is_effect...
1114a
1114b
1114c
1114d

1400A

Back

Spannotations

Nutrition 1202aA

Outcome 1202bA

Domain 1202cA

Diet Plan 1202fA

Exercise 1202dA

Substance 1202eA

Relations 1204A

Reason

Edit Scheme

| Patient Info | More Info |
| --- | --- |
| Birth Date | May 23, 1952 |
| State | **California** |
| Gender | |
| City | |
| Provider ID | |
| Weight | **238 lb** |
| Race | **Asian** |

Previous 104 of 900 Next

DEMOGRAPHICS 94% DISEASE 99% WEIGHT 92%
A 66yo female with heart failure and weight of 238

HISTORY 78%, TREATMENT 97%
pounds, status post gastric band placement 15 years

WEIGHT LOSS 95%
ago. Experienced an initial loss of 78 pounds but has

WEIGHT GAIN 81%
regained almost all of the weight. She feels

FEELING 96% FEELING 96%
frustrated and unhappy due to her weight. She

DRUG 99%
denies thoughts of self harm. She takes Lexapro for

DISEASE 89% DIET-PLAN DISEASE 73%
depression. She has been prescribed a diabetic diet. + REASON NUTRITION
She attempts to eat mostly lean meats and FREQUENCY 69%
vegetables. She goes on walks occasionally. Her FAMILY STRUCTURE 86%
husband is supportive. The patient would like to TREATMENT 96%
proceed with laparoscopic gastric band removal WEIGHT GAIN 81%
since she regained the weight.

1210A

1212A

1214A

AUTOMATIC 1208A

- ☑ model/drug
  2 matches
- ☑ model/disease
  2 matches
- ☑ model/demographics
  2 matches
- ☑ model/time
  2 matches
- ☑ model/feeling
  2 matches
- ☑ model/weight change
  3 matches
- ☑ model/family structure
  1 match

MANUAL

- ☑ Andy Snow
  2 labels, 1 relation

FIG. 15

Figure 17:
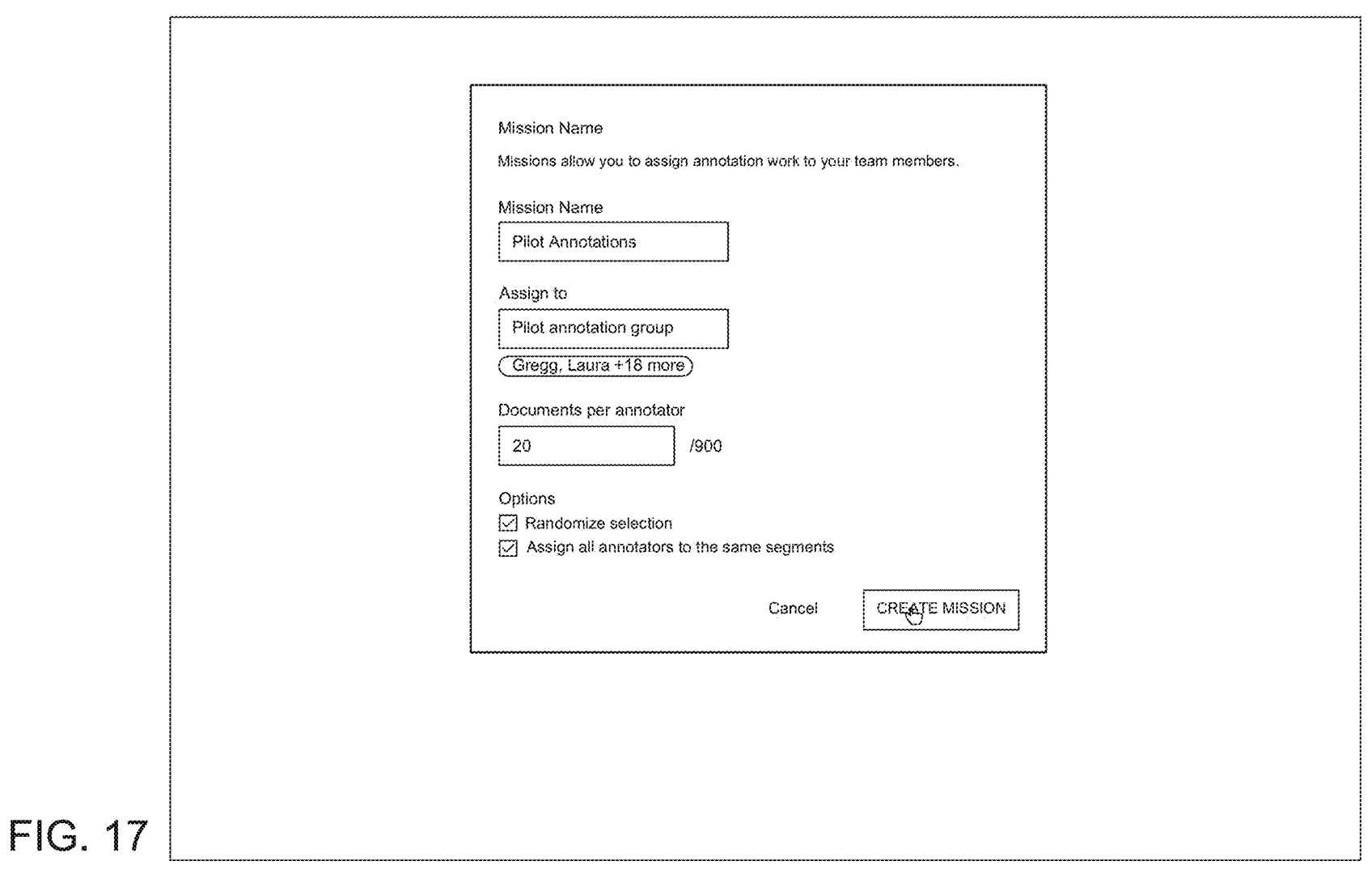

Mission Name

Missions allow you to assign annotation work to your team members.

Mission Name

Pilot Annotations

Assign to

Pilot annotation group

Gregg, Laura +16 more

Documents per annotator

20 /900

Options

☒ Randomize selection

☒ Assign all annotators to the same segments

Cancel

CREATE MISSION

FIG. 22
2100
PV Abstract First Scale
Display 2 sets
Filter by All documents
Contains All
X-Ray
182/182
Reconcile
Kim's annotations
Case Report
The intra-host evolutionary process of hepatitis C virus
(HCV) was analyzed by phylogenetic and coalescent
methodologies in
. Direct sequence analysis of
the E2 and NS5A regions showed diverse evolutionary
dynamics, in agreement with different relationships
between these regions and the host factors. The Bayesian
Skyline Plot analyses of the E2 sequences (cloned) yielded
different intra-host evolutionary patterns for each
genotype: a steady state of a "consensus" sequence for
HCV-1a; a pattern of lineage splitting and extinction for
HCV-2a; and a two-phase (drift/diversification) process
for HCV-3a. Each genotype evolving in the same patient
and at the same time presents a different pattern
apparently modulated by the immune pressure of the
Bill's annotations
Case Report
The intra-host evolutionary process of hepatitis C virus
(HCV) was analyzed by phylogenetic and coalescent
methodologies in a
Direct sequence analysis of
the E2 and NS5A regions showed diverse evolutionary
dynamics, in agreement with different relationships
between these regions and the host factors. The Bayesian
Skyline Plot analyses of the E2 sequences (cloned) yielded
different intra-host evolutionary patterns for each
genotype: a steady state of a "consensus" sequence for
HCV-1a; a pattern of lineage splitting and extinction for
HCV-2a; and a two-phase (drift/diversification) process
for HCV-3a. Each genotype evolving in the same patient
and at the same time presents a different pattern
apparently modulated by the immune pressure of the

Patient #78982

Patient Info

| | |
|---|---|
| Birth Date | May 23, 1952 |
| State | California |
| Gender | |
| City | |
| Provider ID | |
| Weight | 238 lb |
| Race | Asian |

Roam's NLP Variables

| | |
|---|---|
| Disease | heart failure, depression |
| Procedures | gastric band placement, laparoscopic... |
| Mental disposition | frustrated, unhappy |
| Exercise | walks occasionally |
| Diet-Plan | diabetic diet |

FIG. 32

PARSE TREE LOGICAL FORM CYPHER STATEMENT RESULTS

```
MATCH (cmsprescriptions_provider1 :"CMSPrescriptions/Provider")
MATCH (cmsprescriptions_provider1 :"CMSPrescriptions/Provider")-
[cmsprescriptions_provider_prescribed_cmsprescriptions_cmsdrug1:"PRESCRIBED"]->(cmsprescriptions_cmsdrug1
s"CMSPrescriptions/CMSDrug")
MATCH (cmsprescriptions_cmsdrug1 :"CMSPrescriptions/CMSDrug")
MATCH (cmsprescriptions_cmsdrug1 :"CMSPrescriptions/CMSDrug")-
[cmsprescriptions_cmsdrug_instance_of_cmsprescriptions_drug1:"INSTANCE_OF"]->(cmsprescriptions_drug1
:"CMSPrescriptions/Drug")
MATCH (cmsprescriptions_drug1 :"CMSPrescriptions/Drug" { uuid: 'CMSPrescriptions/Drug/JANUVIA' })
MATCH (cmsprescriptions_j?rovider1 :"CMSPrescriptions/Provider")-
[cmsprescriptions_provider_state_cmsprescriptions_state1:"STATE"]->(cmsprescriptions_state1
i"CMSPrescriptions/State")
MATCH (cmsprescriptions_state1 :"CMSPrescriptions/State" { uuid: 'CMSPrescriptions/State/NY' })
RETURN
cmsprescriptionsproviderjrescribed_cmsprescriptions_cmsdrug1.total_claim_count,cmsprescriptions_j>rovider1
ORDER BY cmsprescriptions_provider_prescribed_cmsprescriptions_cmsdrug1.total_claim_count DESC
LIMIT 10
```

FIG. 44(c)

METHODS, APPARATUS AND SYSTEMS FOR ANNOTATION OF TEXT DOCUMENTS

CROSS-REFERENCE TO RELATED APPLICATIONS

This Application is a Continuation of U.S. patent application Ser. No. 17/578,390, filed Jan. 18, 2022, entitled "METHODS, APPARATUS AND SYSTEMS FOR ANNOTATION OF TEXT DOCUMENTS", which is a Continuation of U.S. patent application Ser. No. 16/815,873, filed Mar. 11, 2020, entitled "METHODS, APPARATUS AND SYSTEMS FOR ANNOTATION OF TEXT DOCUMENTS", which claims the priority benefit, under 35 U.S.C. § 119 (e), of U.S. Patent Application Ser. No. 62/816,596, filed Mar. 11, 2019, entitled "METHODS, APPARATUS AND SYSTEMS FOR ANNOTATION OF TEXT DOCUMENTS". The entire contents of these applications are incorporated herein by reference in their entirety.

BACKGROUND

Natural language processing (NLP) is a subfield of artificial intelligence (AI) concerned with the interactions between computers and human (natural) languages (e.g., how to program computers to process and analyze large amounts of natural language data). NLP generally relies on machine learning (ML) algorithms to learn rules for processing languages through the analysis of text corpora (e.g., large and structured sets of annotated documents) representative of typical real-world contextual examples of text. Once these ML algorithms sufficiently learn certain processing rules for language in a given context, they can be applied to new samples of language to automatically identify certain elements of the language (e.g., certain words or phrases, particular topics or concepts mentioned in the language, certain relationships between topics or concepts). Since language cannot be processed directly by computers, NLP first relies on translating language to structured mathematical representations that can be processed by ML algorithms.

More specifically, in NLP, a "feature representation" is a structured mathematical representation for language (e.g., some portion of text) that is suitable for computer processing. A feature representation is generated by applying one or more "feature functions" to the text in question to translate that text to the feature representation (this translation process is sometimes referred to as "featurization"). The feature representation in turn determines what information an ML algorithm has access to regarding the text. In one example of featurization, a word might be translated into a single number or a vector of numbers respectively representing certain aspects of the word (e.g., how many letters it has, a first numeric code for part of speech or grammar type, a second numeric code for capitalization, etc.). Thus, in one aspect, the predictive value of the feature representation to an ML algorithm for NLP may be based, at least in part, on the complexity of the feature representation (e.g., a simpler mathematical representation for the text, like a single number, generally has less predictive value to the machine learning algorithm than a more complex representation, like a vector of numbers).

ML algorithms for NLP (also referred to herein as "NLP models") generally utilize statistical methods that make probabilistic decisions based on attaching real-valued weights to feature representations. Such models have the advantage that, when they are applied to a new sample of text to automatically identify certain portions of the text, they can express the relative certainty of many different possible answers rather than only one; this probabilistic approach generally produces more reliable results when such a model is included as a component of a larger system. Statistical methods have proven to be an effective way to approach NLP, but NLP models often work better when the models are provided with "pointers" to what is relevant about a source text, rather than just massive amounts of text. Such pointers also are referred to as "annotations" to the original text in question; generally speaking, any metadata tag (or "label") added to one or more elements of text to categorize or specifically identify the text in some manner may be considered as an annotation.

"Supervised learning" refers to an NLP model that can learn to automatically label text with certain annotations, based on example text that is first annotated by humans according to a set of predetermined labels; this human-annotated text provides "labeled training data" for the NLP model. In one aspect, a supervised learning NLP model infers a function, based on labeled training data, to map text being processed to a corresponding label of the set of predetermined lab. The NLP model trained in this fashion can then process new unannotated text to automatically annotate it according to the set of predetermined labels. From the foregoing, it should be appreciated that for such NLP models to perform efficiently and effectively (e.g., correctly identify text and label it appropriately), the annotations provided in the labeled training data must be accurate and relevant to the task the NLP model is trying to achieve. Accordingly, the discipline of language annotation is an important component of effective NLP.

SUMMARY

Industrial applications of NLP involve analysis of large numbers of documents that include unstructured free-form text. These relatively large applications of NLP endeavor to extract structured information from a significant quantity of unstructured free-form text to thereby gain some valuable insight to support a particular use-case (e.g., a specific situation in which a product or service could potentially be used) or address a particular business question (e.g., exploring factors that influence a given use-case). To provide structured information from the unstructured free-form text documents, supervised learning NLP models process the text documents and automatically label the text according to a predetermined annotation scheme. However, as noted above, to be effective and reliable, such NLP models must be trained on accurately labeled training data.

Accordingly, industrial applications of NLP often depend on rapidly developing new annotated datasets in particular domains of interest and/or for specialized use-cases. To create such annotated datasets, a group of human "manual" annotators explore a significant sample of unannotated documents (relevant to the domain of interest/use-case) in free-form ways and collaborate to make numerous complex decisions toward providing an annotated dataset for training NLP models. In particular, as human annotators work together on a given annotation project, they generally collaborate on how to define labels for text (for an "annotation scheme"), and on what criteria to use for assigning those labels to text ("annotation guidelines"). These collaborative decisions often change from time to time and evolve during a given annotation project.

The Inventors have recognized and appreciated that existing conventional tools for annotation projects are substantially, if not exclusively, focused on the relatively isolated act of assigning labels to text, and virtually ignore the collaborative, exploratory steps that human annotators take during an annotation project (e.g., to define labels in the first instance, and to prescribe guidelines for assigning labels to text). Conventional annotation tools tend to presuppose that an annotation scheme and annotation guidelines are set in stone, such that even small changes like adjusting the label set for the annotation scheme, or changing a given name for a label, can be prohibitively cumbersome. Moreover, to the Inventors' knowledge, there is no single tool that contemplates and handles, in a holistic fashion, all of the required subtasks germane to a collaborative annotation project.

The foregoing situation might be acceptable for teams of researchers who annotate new documents only periodically; however, a fragmented and incomplete assembly of conventional annotation tools is prohibitive for industrial applications of NLP that depend on being able to rapidly create high-quality annotated training data. In the latter context, the annotators are likely to be teams of highly-trained and specialized experts in one or more domains germane to the use-case or business question at hand. Typically, such annotators are not necessarily computer science or software experts accustomed to working in a free-form software development environment that lets them assemble ad hoc annotation tools quickly. This problem is not solved by instead assigning computer scientists or NLP engineers to do the domain-specific annotation work; on the contrary, if the annotation project is designed by an engineering team, then it will arguably not benefit fully from the insights of the highly-trained specialized domain experts.

In view of the foregoing, the Inventors have designed an Annotation Manager (AM) as an integrated system that enables domain experts to design and run annotation projects essentially on their own. In the present disclosure, such a system is referred to as "Alpine." Alpine is an inventive GUI-based tool for facilitating annotation projects for unstructured text documents (or semi-structured documents including free-form text) in a given information domain, using NLP techniques, to extract structured information from free-form text. As discussed in greater detail below, in various aspects Alpine supports collaborative and non-linear workflows amongst multiple human annotators to facilitate successful annotation. Alpine users (annotators) can explore text documents via sophisticated search functions, discuss and create annotation labels and guidelines and capture those discussions in an annotation manual, annotate text in an active learning workflow, adjust annotation guidelines and labels on the fly, and study the resulting annotated documents. Alpine is also a powerful Annotation User Interface (AUI), supporting intuitive and flexible annotations for spans ("spannotations"), span attributes, and relationships between annotated spans ("spannotation relations"). Using Alpine, a team of domain experts can operate independently of engineering teams, allowing the domain experts to work directly with project managers and customers when defining a custom annotation project for a specific use-case or business question.

In one example implementation discussed herein, Alpine may be employed for annotation projects in the health care domain. Annotated datasets from the health care domain prepared using Alpine may in turn be employed to train sophisticated NLP models that provide valuable insights regarding many facets of health care including, but not limited to, patient experience and quality of life, brand recognition, diagnoses considered and rejected, treatment strategies, treatment rationales, provider assessments outside of labs, patient and provider attitudes, patient's view of disease progression, social and behavioral risk factors, areas of disagreement, obstacles to care, and perceptions of safety and efficacy. The health care domain specificity enables some advantageous and inventive features in Alpine for preannotating and searching text documents, as well as rapid development of NLP target models for the annotation project. That said, it should be appreciated that many inventive aspects of Alpine's functionality, user interfaces, and data handling capabilities as described in detail herein are domain independent, such that Alpine may be effectively employed for annotation projects and industrial applications of NLP across a wide variety of domains to address diverse use-cases and business questions.

In another significant aspect, some of Alpine's inventive technical features may be significantly enhanced by utilizing domain-specific information derived from a "Roam Knowledge Graph" (RKG). As discussed further below, a "knowledge graph" refers to a graph representation of data (e.g., using nodes to represent entities and edges to represent relationships between entities), wherein the graph representation is based at least in part on one or more datasets and/or ontologies pertaining to a particular information domain. A Roam Knowledge Graph is an inventive knowledge graph in which multiple subgraphs representing respective datasets from different data sources are interconnected via a linking layer (also referred to as a "canonical layer" or "semantic layer").

With respect to knowledge graphs and their utility for annotation of documents, the Inventors have recognized and appreciated that many things, if not everything-a name, a number, a date, an event description-acquires greater meaning in context, where it can be compared with other things. Context is essential for understanding, and the more context one has, the fuller one's understanding can be. Individual pieces of information or relatively confined sources of data are often unlikely to provide sufficient context to facilitate a deeper understanding of the meaning of the information at hand. Even with relatively larger amounts of information available, respective pieces of information may remain unconnected, inconsistent or disjointed in some manner, and relationships between certain pieces of information may not be readily apparent or even discernible from the respective (and often unconnected, inconsistent, or disjointed) pieces.

In view of the foregoing, the Inventors also have recognized and appreciated that multiple advantages leading to increased understanding of information are provided by connecting multiple pieces of information to the wider world from which they are extracted. Failure to make these connections is tantamount to pretending the world is less complex than it is. Accordingly, the Inventors have conceived of an inventive data storage and retrieval system that significantly facilitates the interconnection of multiple separate pieces of information (also referred to herein as "datasets") that may in some instances be heterogeneous in nature and obtained/derived from a wide variety of different sources. Various implementations of such an inventive data storage and retrieval system employ a knowledge graph including a unifying "linking layer" (also referred to as a "canonical layer") that provides a frame of reference for meaningfully connecting multiple subgraphs respectively representing diverse datasets. Such a knowledge graph is referred to herein as a "Roam Knowledge Graph" (RKG).

In various aspects discussed in greater detail below, understanding information and its context via the inventive data storage and retrieval system disclosed herein enables new discoveries and provides a stronger basis for influencing and/or controlling complex real-world interactions (between and among various entities). Additionally, exposing the context of data and its interrelationships with other data significantly enhances the ability to analyze the data and model it to make predictions and derive meaning from new data. In particular, data models based in part on information that is connected via the data storage and retrieval system disclosed herein, and the greater context this system provides, may be used to analyze new data in a more automated and meaningful way to enable actionable consequences for influencing and controlling complex real-world interactions. In yet another aspect, the inventive data storage and retrieval system disclosed herein particularly facilitates the storage and automated/semi-automated analysis and modeling of large bodies of text corpora (e.g., via the inventive Alpine annotation tool).

More specifically, in connection with facilitating annotation of documents by human annotators via the Alpine annotation tool, in one implementation Alpine may automatically "preannotate" documents in an annotation project dataset based on various information derived from an RKG. For example, through queries of the RKG, a particular lexicon may be built that includes various text strings (and optionally other metadata) relating to one or more particular concepts ("entity types") of potential interest mentioned in respective documents of the annotation project dataset. Based on this graph-derived lexicon (also referred to as an "RKG-based lexicon"), an NLP model referred to as an "extractor" may be designed to process a string of characters in a given document to find all mentions of a given concept or entity of interest that statistically matches one of the text strings in the RKG-based lexicon from which the extractor was built. In this manner, an extractor may be utilized in Alpine to serve as an automatic annotator to find and identify (e.g., label) particular concepts and entities of interest in documents and thereby provide "preannotations" in advance of annotation by a manual annotator. In one aspect, such preannotations are heuristic in nature and facilitate preliminary exploration of the annotation project dataset (e.g., by one or more domain experts/human annotators, data scientists, and/or NLP engineers).

Accordingly, it should be readily appreciated by those of skill in the relevant arts that the inventive concepts disclosed herein are firmly rooted in computer technology (e.g., inventive graphical user interfaces, and data storage and retrieval structures) and provide multiple technological solutions that improve the function of computers themselves (e.g., faster, more efficient, more reliable, and more intelligible data searching, data retrieval, and data modeling functionalities, as well as more expansive annotation functionality). Furthermore, the various technological solutions disclosed herein are not well-known, conventional, and/or well understood in the conventional arts to which the concepts disclosed herein pertain.

In some implementations, a method for displaying, and facilitating annotation of, at least a first document to be annotated as part of a collaborative annotation project in which a plurality of documents constituting an annotation project dataset are processed, by at least one computer including at least one processor executing code, to provide annotations in respective documents of the annotation project dataset, the annotations serving as training data for a supervised learning natural language processing (NLP) project target model is described herein. The method includes A) displaying, via the at least one computer, at least one first graphical user interface that facilitates definition and/or modification of, and displays, an annotation scheme for the annotation project. The annotation scheme can comprise a set of annotation labels that can be used to provide the annotations serving as the training data.

The method also includes B) displaying, via the at least one computer, at least one second graphical user interface that: B1) displays at least a portion of the first document in a first region of the at least one second graphical user interface; B2) displays the set of annotation labels of the annotation scheme in a second region of the at least one second graphical user interface; and B3) facilitates annotation of the portion of the first document displayed in the first region of the at least one second graphical user interface. The annotation of the portion of the first document displayed in the first region of the at least one graphical user interface can be facilitated via: B3a) selection of at least a first annotation label of the set of annotation labels displayed in the second region of the at least one second graphical user interface; and B3b) following selection of the first annotation label in B3a), placement of the selected first annotation label adjacent to at least a first span of text in the portion of the first document displayed in the first region of the at least one second graphical user interface.

In some implementations, a method for displaying, and facilitating annotation of, at least a first document to be annotated as part of a collaborative annotation project in which a plurality of documents constituting an annotation project dataset are processed, by at least one computer including at least one processor executing code, to provide annotations in respective documents of the annotation project dataset, the annotations serving as training data for a supervised learning natural language processing (NLP) project target model is disclosed herein. The method includes A) displaying, via the at least one computer, at least one first graphical user interface to facilitate exploration of at least some of the respective documents of the annotation project dataset based on a search query including at least one entity of interest. The method also includes B) in response to the search query, processing, by the at least one computer, the at least some of the respective documents based on at least one lexicon relating to the at least one entity of interest included in the search query, the at least one lexicon comprising at least one synonym, at least one acronym, at least one rephrasing, at least one identifier, and/or at least one code relating to the at least one entity of interest. The method also includes C) displaying, via the at least one first graphical user interface or at least one second graphical user interface, at least one categorization of the at least some of the respective documents of the annotation project dataset based on B).

The method also includes D) displaying, via the at least one computer, at least one third graphical user interface that facilitates definition and modification of, and displays, an annotation scheme for the annotation project based at least in part on the at least one categorization in C). The annotation scheme can comprise a set of annotation labels used to provide the annotations serving as the training data.

The method also includes E) displaying, via the at least one computer, at least one fourth graphical user interface that: E1) displays at least a portion of the first document in a first region of the at least one fourth graphical user interface; E3) facilitates annotation of the portion of the first document displayed in the first region of the at least one fourth graphical user interface via: E3a) selection of at least a first annotation label of the set of annotation labels displayed in the second region of the at least one fourth graphical user interface; and E3b) following selection of the first annotation label in B3a), placement of the selected first annotation label adjacent to at least a first span of text in the portion of the first document displayed in the first region of the at least one second graphical user interface.

In some implementations, at least one non-transitory computer-readable medium encoded with processor-executable instructions that, when executed by at least one processor, perform a method for displaying, and facilitating annotation of, at least a first document to be annotated as part of a collaborative annotation project in which a plurality of documents constituting an annotation project dataset are processed, by at least one computer including at least one processor executing code, to provide annotations in respective documents of the annotation project dataset, the annotations serving as training data for a supervised learning natural language processing (NLP) project target model is described herein. The method includes A) displaying, via the at least one computer, at least one first graphical user interface that facilitates definition and/or modification of, and displays, an annotation scheme for the annotation project. The annotation scheme can comprise a set of annotation labels used to provide the annotations serving as the training data. The method also includes B) displaying, via the at least one computer, at least one second graphical user interface that: B1) displays at least a portion of the first document in a first region of the at least one second graphical user interface; B2) displays the set of annotation labels of the annotation scheme in a second region of the at least one second graphical user interface; and B3) facilitates annotation of the portion of the first document displayed in the first region of the at least one second graphical user interface via: B3a) selection of at least a first annotation label of the set of annotation labels displayed in the second region of the at least one second graphical user interface; and B3b) following selection of the first annotation label in B3a), placement of the selected first annotation label adjacent to at least a first span of text in the portion of the first document displayed in the first region of the at least one second graphical user interface.

In some implementations, at least one computer for displaying, and facilitating annotation of, at least a first document to be annotated as part of a collaborative annotation project in which a plurality of documents constituting an annotation project dataset are processed by the computer to provide annotations in respective documents of the annotation project dataset, the annotations serving as training data for a supervised learning natural language processing (NLP) project target model is disclosed herein. The at least one computer can comprise at least one computer memory, and at least one processor communicatively coupled to the at least one computer memory. Upon execution by the at least one processor of processor-executable code, the at least one computer: A) displays at least one first graphical user interface that facilitates definition and/or modification of, and display of, an annotation scheme for the annotation project. The annotation scheme can comprise a set of annotation labels used to provide the annotations serving as the training data; and B) displays at least one second graphical user interface that: B1) displays at least a portion of the first document in a first region of the at least one second graphical user interface; B2) displays the set of annotation labels of the annotation scheme in a second region of the at least one second graphical user interface; and B3) facilitates annotation of the portion of the first document displayed in the first region of the at least one second graphical user interface via: B3a) selection of at least a first annotation label of the set of annotation labels displayed in the second region of the at least one second graphical user interface; and B3b) following selection of the first annotation label in B3a), placement of the selected first annotation label adjacent to at least a first span of text in the portion of the first document displayed in the first region of the at least one second graphical user interface.

In some implementations, a method for facilitating design and execution of annotation projects for natural language processing (NLP) applications, by at least one computer including at least one processor executing code is described herein. The method can include A) displaying, via the at least one computer, at least one first graphical user interface that facilitates preannotation of at least some documents of a first annotation project dataset comprising a plurality of documents pertaining to a first information domain; B) displaying, via the at least one computer, at least one second graphical user interface that facilitates annotation of at least a first document in the first annotation project dataset by at least one domain expert in the information domain to which the first annotation project dataset pertains; and C) displaying, via the at least one computer, at least one third graphical user interface, to facilitate design and/or training of at least one natural language processing (NLP) project target model to be used by the at least one computer to automatically annotate at least a first number of the plurality of documents of the first annotation project dataset.

In some implementations, at least one graphical user interface (GUI)-based computer for facilitating an annotation project for unstructured text documents or semi-structured documents including free-form text in a given information domain is described herein. The GUI-based computer can support collaborative workflows amongst multiple human annotators. The GUI-based computer can include at least one computer memory, and at least one processor communicatively coupled to the at least one computer memory. Upon execution by the at least one processor of processor-executable code, the GUI-based computer: A) displays a first graphical user interface to allow exploration of the unstructured text documents or semi-structured documents via at least one search function based on at least one lexicon; B) displays a second graphical user interface to allow at least a first human annotator of the multiple human annotators to discuss, create and adjust annotation labels and guidelines for the annotation project; and C) displays a third graphical user interface to allow the first human annotator to annotate the free-form text in at least a first document of the unstructured text documents or semi-structured documents based on the annotation labels and guidelines to create a plurality of annotations in the first document, the plurality of annotations including a plurality of spannotations and at least one spannotation relation.

It should be appreciated that all combinations of the foregoing concepts and additional concepts discussed in greater detail below (provided such concepts are not mutually inconsistent) are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 15 illustrates an eleventh screen shot of the AUI showing an example of a spannotation relation that has been added between the spannotations in the document shown in FIG. 14, according to one inventive aspect.

FIG. 17 illustrates a twelfth screen shot of the AUI showing the designation of a mission in which certain annotators are assigned to review and annotate documents of a project dataset, according to one inventive implementation.

FIG. 27 illustrates a twenty-first screen shot of the AUI, showing a document that includes preannotations (in gray shading) together with model-generated spannotations (colors) from applying the initially-trained project NLP target model from FIG. 25 to the document, according to one inventive implementation.

FIG. 32 illustrates a twenty-sixth screen shot of the AUI, showing the type of structured information (e.g., Roam's NLP Variables) that may be added to respective documents of a project dataset relating to automatic annotations generated by a sufficiently-trained project NLP target model, according to one inventive implementation.

FIG. 44C illustrates an example Cypher query generated by a semantic parsing engine, according to one inventive implementation.

DETAILED DESCRIPTION

Figure 1:
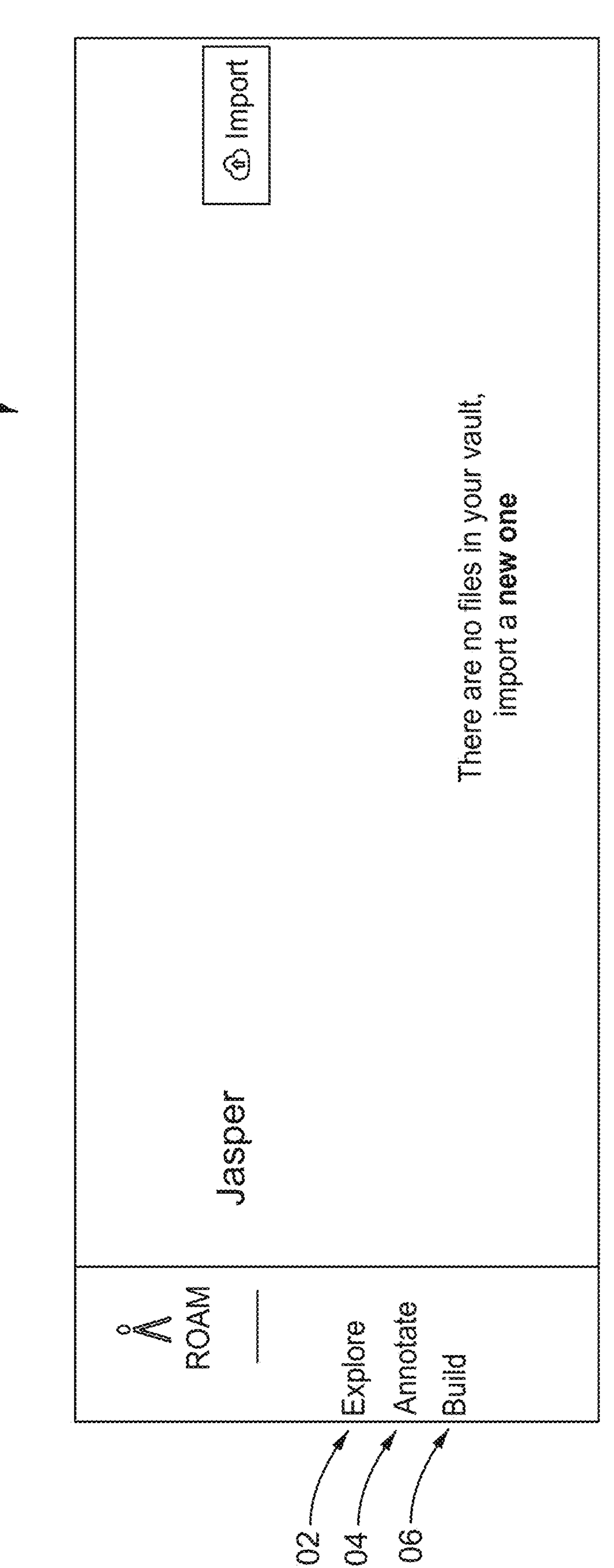
FIG. 1 illustrates a first screen shot of Alpine's Annotation User Interface (AUI) showcasing various functionalities that AUI can facilitate in order to autonomously design and run projects for NLP applications, according to one inventive implementation.

Following below are a glossary of terms and detailed descriptions of various concepts related to, and embodiments of, methods, apparatus and systems for annotation of text documents. It should be appreciated that various concepts discussed herein may be implemented in multiple ways, as the disclosed concepts are not limited to any particular manner of implementation. Examples of specific implementations and applications are provided herein primarily for illustrative purposes.

The figures, appendices, and example implementations described below are not meant to limit the scope of the present disclosure to the example implementations discussed herein. Other implementations are possible by way of interchange of at least some of the described or illustrated elements. Moreover, where certain elements of the disclosed example implementations may be partially or fully instantiated using known components, in some instances only those portions of such known components that are necessary for an understanding of the present implementations are described, and detailed descriptions of other portions of such known components are omitted so as not to obscure the salient inventive concepts underlying the example implementations.

Glossary

Information Domain-A "domain" refers to an area of particular activity and/or knowledge. A domain may define or encompass a set of common or shared subjects (e.g., people and/or things), ideologies, academic or research areas, professions, disciplines, concepts, characteristics, requirements, and/or terminology. Examples of domains include, but are not limited to, health care (discussed further below), finance, insurance, e-commerce, entertainment, law, sports, social media, transportation, energy resources and consumption, climate science, education, agriculture, housing, immigration, and other scientific/academic endeavors. Some domains may include one or more subdomains, and one or more subdomains in a given domain may be nested inside one another; additionally, respective domains or subdomains may overlap with one another to some extent (e.g., the health care domain may include a "medical tests" subdomain and a "surgical procedures" subdomain, wherein some tests don't involve surgery, some surgeries are not tests, but some biopsies are arguably both medical tests and surgical procedures). An "information domain" refers to any electronic information in various forms pertaining to a particular domain (including one or more subdomains if applicable).

Health Care Domain—As an example of a domain, the "health care domain" encompasses a wide variety of activity and knowledge relating to human health and well-being. Examples of such activity and knowledge include but are not limited to: the study and treatment of various ailments and diseases; mitigation and prevention of various ailments and diseases; various forms and techniques of care; diagnoses and administration of drugs; formulation of new drugs, diagnoses and treatments; genes and their relationship to phenotypic expression; various specializations and credentialing for health care practitioners; health care economics, insurance and regulation; and patient demographics. Various electronic information pertaining to the health care domain (e.g., the "health care information domain") includes, but is not limited to, public health statistics and databases, adverse event databases, medical ontologies, regulatory documents, insurance company policy documents, electronic medical records (e.g., electronic hospital records or "EHRs"), patient surveys, insurance claims, Medical Science Liaison (MSL) notes, and Medical Information Requests (MIRs).

Dataset-A "dataset" refers to one or more electronic files provided by a particular source. Examples of sources that may provide a dataset include, but are not limited to, business entities (public or private companies), academic institutions, research organizations, government agencies, non-profit organizations, news outlets, and individuals. In some instances, multiple files included in a dataset include information that in some respects is related and relevant to the source of the dataset. One or more files in a dataset may include, for example, data that was generated by the source, data that was collected by the source, data that was received by the source, and/or data that was generated, collected and/or received by the source and modified or curated in some manner by the source. Multiple files in a given dataset may in some instances represent different tables of a database. The file(s) in a dataset may have any of a number of different formats, and multiple files in a dataset may have the same format or different formats. In some examples, a dataset may include a single .csv file (comma-separated values file) or multiple .csv files obtained from a given source.

Fundamental/Golden Dataset—In some implementations discussed herein, a "fundamental dataset" (also referred to as a "golden dataset") refers to a dataset of factual information from a trusted (and often public) source (e.g., a list of United States zip codes obtained from the U.S. Postal Service; National Provider Identifier (NPI) records obtained from the National Plan and Provider Enumeration System (NPPES) of the U.S. Department of Health and Human Services).

Structured Data—"Structured data" refers to multiple data elements than can be meaningfully aggregated, and that generally are organized into a formatted repository of data elements (e.g., a spreadsheet or database including one or more tables with rows and columns), so that respective elements of the data are addressable and easily accessible and searchable (e.g., for processing and analysis). In one aspect, respective data elements of structured data are numerical and on the same or similar scale; in this case, examples of meaningful aggregation may include, but are not limited to, sums or averages. In another aspect, respective data elements of structured data may be numeric, alphanumeric or text-based, and come from a fixed set of possible values (e.g., U.S. states, shoe sizes, a predetermined set of email addresses); in this case, examples of meaningful aggregations may include, but are not limited to, counts of each unique value from the fixed set of possible values. In yet another aspect, at least some data elements of structured data may be normalized (see below). In yet another aspect, a given spreadsheet, database or file may include one or more elements of structured data, together with one or more other elements of unstructured data (see below) (e.g., one or more columns of a spreadsheet may include a defined range of numerical values, while one or more other columns of the spreadsheet may include free-form text).

Unstructured Data—"Unstructured data" refers to data that either does not have a pre-defined data model or is not organized in a pre-defined manner. Unstructured data is typically text-heavy (e.g., human language), and may contain data such as dates, numbers, and facts as well. Unstructured data is not associated with any tags or metadata about the data, and it has no established schema. This generally results in irregularities and ambiguities in the unstructured data that make it relatively difficult to understand, access, search, and process using traditional programs (as compared to data stored in databases, for example). Examples of unstructured data include, but are not limited to, the body of e-mail messages, word processing documents, videos, photos, audio files, presentations, webpages, and various kinds of business or regulatory documents.

Semi-structured Data—"Semi-structured data" refers to data that is not in a relational database, but nonetheless has some organizational structure (i.e., a known schema) or carries a tag (e.g., XML extensible markup language used for documents on the web), thereby rendering the data somewhat easier to organize, access, search, and analyze.

Heterogeneous Data/Heterogeneous Datasets—"Heterogeneous data" refers to multiple elements of data (or multiple data files) that vary in type and/or format. A "heterogeneous dataset" refers to a given dataset from a particular source that includes heterogeneous data (e.g., one or more files having different types of data and/or multiple files having respective different formats). "Heterogeneous datasets" refers to respective datasets from different sources wherein the respective datasets vary in type and/or format amongst each other (but any given dataset itself of the multiple datasets may or may not include heterogeneous data).

Normalize/Normalization—The terms "normalize" or "normalization" refer to a process of modifying one or more disparate pieces of data relating to a same or similar thing, such that all of the pieces of data relating to the same or similar thing are homogenized in some manner (e.g., according to a predetermined standard or format). For example, considering a first element of data as "Fort Laud" and a second element of data as "Ft. Lauderdale" (both of which presumably refer to the same city in the state of Florida, U.S.A.), the first element of data may be normalized to "Ft. Lauderdale," the second element of data may be normalized to "Fort Laud," or both the first and second elements of data may be normalized to "Ft. Laud" or another predetermined standard (e.g., the airport code "FLL"). In some examples of normalization, the predetermined standard or format to which one or more data elements are normalized may be an official, widely accepted, certified, and/or pre-ordained format for the data element in question, also referred to herein as a "canonical source." In this respect, when normalization utilizes a canonical source as the target for modifying data elements if/as needed, such a normalization may also be referred to as "canonicalization."

Namespace-A "namespace" is a logical construct for organizing datasets (and multiple files in a given dataset) in computer storage (e.g., a file system). In various implementations discussed herein, a dataset received from a particular source is stored in a namespace associated with the particular source. The namespace itself has an identifier that may be representative of the source (e.g., a namespace for a dataset from the U.S. Postal Service may be labeled as "USPS"). Each element (e.g., a file or other object) within the namespace has a local name that serves as a unique identifier for that element within the namespace (e.g., "zip codes," "States," "Counties"). A namespace makes it possible to distinguish files (or other objects) with similar or identical local names in one or more other namespaces (e.g., files or other objects with similar/identical names that originate from different sources). For example, consider a first dataset of zip codes received from the U.S. Postal Service including the file "California zip codes" logically stored in the namespace "USPS," and a second dataset of zip codes received from a particular state's government records (e.g., California) including the file "California zip codes" logically stored in the corresponding namespace "ca.gov;" in this example, "USPS/California zip codes" may be identified as a different file from "ca.gov/California zip codes" by virtue of the different namespaces, even though the two files have the same local name. In this manner, namespaces may also enable the identification of data provenance (e.g., the file "USPS/zip codes" is known to originate from the USPS source, and the file "ca.gov/zip codes" is known to originate from the California state government source). In general, a namespace is a set of symbols that is used to organize objects so that the objects may be referred to by a same or similar name in one or more other namespaces. Namespaces are commonly structured as hierarchies to allow reuse of names in different contexts (e.g., naming of people with proper names and family surnames, differently-named directories of a computer file system in which a particular file of the same name may be stored in two or more different directories, and computer programming namespaces in which symbols and identifiers pertaining to a particular functionality may be grouped accordingly to avoid name collisions between multiple symbols/identifiers having the same name).

Entity/Entity Type—An "entity" refers to a thing represented in one or more files of a dataset, and an "entity type" refers to a particular category or label for a given entity or multiple entities sharing at least one common aspect (the word "concept" is sometimes used as a synonym for "entity type"). Examples of different entity types include, but are not limited to, persons, physical/tangible objects or compositions of matter, places (geographical references), concepts, legal or professional constructs (e.g., companies, organizations, institutions, government agencies, groups and/or networks, and hierarchies within same), products and/or services and various specifications or other information relating to same, events, occupations or roles, professional and/or academic credentials or specialization, publications, financial information, demographic information, statistical information, health-related information (e.g., diagnoses, medical conditions, symptoms, medical research information), and ontologies (see below). As may be readily appreciated from the foregoing, a given dataset may include data pertaining to a significant number of entities of the same type and/or different types, and there may be a wide variety of different types of entities represented in a given dataset or amongst multiple datasets. An example of a particular entity of the entity type "doctor" is "Dr. Einstein." An example of a particular entity of the entity type "U.S. State" is "California." An example of a particular entity of the entity type "disease" is "lymphoma."

Namespaced Entity Type-A "namespaced entity type" uniquely identifies a set of entities of a given type in a given dataset stored in a corresponding namespace. For example, "U.S. State" is an entity type that may appear in multiple datasets respectively stored in different namespaces, but "USPS/U.S. State" uniquely identifies the collection of U.S. State entities as they are referenced in the USPS dataset from the USPS source.

Relationship-A "relationship" refers to a nexus between two entities of the same type or different types. For example, a first relationship between a first entity (e.g., a person "Erunia") and a second entity of a different type (e.g., a town "Kalamazoo") may be "works in" (i.e., Erunia "works in" Kalamazoo). A second relationship between the same first entity (i.e., Erunia) and a third entity of the same type (e.g., a person "Ahmed") may be "works with" (i.e., Erunia "works with" Ahmed).

Attribute—An "attribute" is an identifier, aspect, quality, or characteristic of an entity or a relationship. Examples of attributes for the entity "Dr. Einstein" may be the surname attribute "Einstein," an arbitrary identifier attribute "DR123," and an aspect attribute "retired." An example of an attribute for the relationship "works with" may be the aspect attribute "occasionally."

Dataset Graph/Subgraph-A "dataset graph" (also referred to herein as "subgraph") refers to a graph representation of a dataset (and, in some instances, a normalized dataset). A dataset graph (or subgraph) typically includes multiple nodes (see below) respectively representing respective entities in the dataset, and multiple edges interconnecting nodes and respectively representing relationships between entities. A given subgraph typically is associated with a particular namespace (which may indicate a source of the dataset that is represented by the subgraph).

Node-A "node" refers to a graph element that represents an entity in a graph representation of a dataset (or data in general). A node typically has a primary identifier that is independent of a name for the entity that the node represents and that is unique in the namespace for the dataset. As with entities, nodes may be categorized according to different node types, and a given node may be associated with one or more attributes. For example, a node in a graph for the entity "Dr. John Einstein" from the National Provider Identifier (NPI) Registry dataset of health care practitioners stored in the namespace "NPI" may have the unique primary identifier "00642," a node type "Physician," a surname attribute "Einstein," and a professional status attribute "retired."

Edge—An "edge" refers to a graph element that represents a relationship between two entities in a dataset in a graph representation of the dataset. As with nodes, edges may be categorized according to different types (i.e., of relationships), and a given edge may be associated with a unique primary identifier and one or more attributes. In one aspect, a primary identifier for an edge may be denoted as a "triple" including the primary identifier of the from-node, a descriptor for the type of edge, and the primary identifier of the to-node (e.g., "DR76, WORKS_WITH, DR18"). In another aspect, one attribute of an edge may relate to a probability regarding the certainty of the relationship represented by the edge (e.g., a numerical value between 0 and 1, inclusive).

Graph Schema-A "graph schema" for a namespace refers to a model for representing, as a graph of nodes and edges, a dataset (or data in general) logically stored in the namespace. A graph schema defines the types of entities in the dataset that are to be represented by nodes in a graph and the relationships between entities of various types that are to be represented by edges in the graph. The graph schema may also define one or more attributes for a given node and/or edge. Given the variety of actual data elements of respective different entity types that may appear in a given dataset (and the corresponding attributes of each entity type), the graph schema for the namespace may be only partially instantiated when a graph of the dataset is generated. For example, a graph schema for the namespace "NPI" (National Provider Identifier Registry of health care practitioners) may include a first node type "Provider" (a unique identifier representing a single health care practitioner in some instances and a health care organization in other instances), a second node type "Specialty" and a third node type "AuthorizedOfficial." The graph schema may include a first edge of type "has" between node types "Provider" and "Specialty" (e.g., Provider, HAS, Specialty), and a second edge of type "has" between node types "Provider" and "AuthorizedOfficial" (e.g., Provider, HAS, AuthorizedOfficial). In an actual graph instantiated according to this graph schema, there may be no node of type "Provider" that would be connected via HAS edges to both a node of type "Specialty" and a node of type "AuthorizedOfficial;" rather, nodes of type "Provider" for single practitioners would be connected to a node of type "Specialty" and not to any node of type "AuthorizedOfficial," and nodes of type "Provider" for organizations would be connected to a node of type "AuthorizedOfficial" and not to any node of type "Specialty."

Ontology—An "ontology" refers to a definition, naming, and representation of categories and properties of entities, and relationships between entities, pertaining to a particular information domain, including subdomains and/or overlapping domains (this is sometimes referred to as a "domain ontology"). An ontology is typically based on logical formalisms that support some form of inference in connection with available data pertaining to the information domain(s), and thereby allows implicit information to be derived from the available explicit data. In this manner, an ontology may in some respects specify the semantics (meaning) of available data pertaining to the information domain(s). Ontologies have been created for some information domains to reduce complexity and organize knowledge and data in the domain(s); this in turn improves communication about the domain(s), and analysis of data and problem solving in the domain(s). In one aspect, an ontology defines a common vocabulary for practitioners who need to share information in a particular domain, and may include machine-interpretable definitions of basic concepts in the domain and relations among the concepts. For example, in the health care domain, health care professionals use ontologies to represent knowledge about symptoms, diseases, and treatments, and pharmaceutical companies use ontologies to represent information about drugs, dosages, and allergies. Some examples of ontologies in the health care domain include, but are not limited to, the Unified Medical Language System from the U.S. National Library of Medicine, RxNorm (drugs), SNOMED CT (Systemized Nomenclature of Medicine), SNOP (Systemized Nomenclature of Pathology), the GALEN Common Reference Model, the National Drug Data File (NDDF), the International Statistical Classification of Diseases and Related Health Problems, a medical classification list by the World Health Organization (ICD10), Chemical Entities of Biological Interest (ChEBI), Current Procedural Terminology (CPT), the Anatomical Therapeutic Chemical (ATC) classification system (classification of active ingredients of drugs according to the organ or system on which they act and their therapeutic, pharmacological and chemical properties, including Defined Daily Doses (DDD)), the International Classification of Functioning, Disability and Health (ICF), LOINC (for health measurements, observations, tests and documents), and the Medical Dictionary for Regulatory Activities (MedDRA).

Knowledge Graph—a "knowledge graph" refers to a graph representation of data (e.g., using nodes to represent entities and edges to represent relationships between entities), wherein the graph representation is based at least in part on one or more datasets and/or ontologies pertaining to a particular information domain. In one aspect, a knowledge graph may be self-descriptive and may provide a single place to find data pertaining to an information domain and understand its meaning (e.g., by virtue of the one or more ontologies on which the knowledge graph is based); in this respect, a knowledge graph encodes the meaning of the data that it represents (e.g., by using node and edge identifiers, types and attributes that are familiar to those interested in, or practitioners of, the information domain). A knowledge graph can be queried to traverse nodes and edges and thereby discover how data from different parts of an information domain may relate to each other. To this end, various graph-computing techniques may be employed (e.g., shortest path computations, network analysis) to uncover "hidden" knowledge represented in the knowledge graph that may be too complex for human cognition. In another aspect, a knowledge graph may be queried in a style that is closer to a natural language (e.g., by virtue of the ontologies employed, which would include vocabulary familiar to practitioners in the domain of interest); this facilitates search and discovery of information encoded in the knowledge graph. In yet another aspect, characteristics pertaining to both nodes and edges in a knowledge graph (e.g., identifiers, types, attributes associated with nodes and edges) may be subjected to computer analytical operations (e.g., being passed as an argument, returned from a function, modified, and assigned to a variable). In yet another aspect, new data items or datasets may be added to a knowledge graph over time; in particular, one or more ontologies on which the knowledge graph is based may be extended and/or revised as new data is considered for addition to the graph, and new entities and/or entity types in datasets may be represented as nodes and connected via edges to existing nodes (based on existing or extended/revised ontologies). This makes knowledge graphs convenient for storing and managing data in use-cases where regular data updates and/or data growth are important, particularly when data is arriving from diverse, heterogeneous sources. In yet another aspect, a knowledge graph is also able to capture diverse metadata annotations such as provenance or versioning information, which make a knowledge graph well-suited for working with dynamic datasets.

Roam Knowledge Graph—The "Roam Knowledge Graph" (RKG) is an innovative knowledge graph in which multiple subgraphs representing respective datasets in different namespaces are interconnected via a linking layer (also referred to as a "canonical layer" or "semantic layer," discussed below). In one aspect, the respective datasets represented by subgraphs in different namespaces of an RKG may pertain to a particular information domain and/or overlapping information domains. In other aspects, the respective datasets represented by subgraphs in different namespaces of an RKG may include heterogeneous datasets, and a given dataset represented by a subgraph in a particular namespace of an RKG may include heterogeneous data.

Canonical/Semantic/Linking Layer-A "canonical layer" (also referred to as a "semantic layer" or a "linking layer") of a Roam Knowledge Graph (RKG) refers to a set of linking nodes ("canonical nodes") of predetermined node types ("canonical node types"), wherein the canonical nodes are connected via edges to nodes in respective subgraphs in different namespaces of the RKG. The canonical node types for the canonical nodes of the canonical layer correspond to selected node types that: 1) are present in multiple subgraphs of the RKG, or present in one subgraph of the RKG and likely to appear in one or more other datasets pertaining to the information domain (that may be later added to the RKG as one or more new subgraphs); and 2) have some significance in the information domain(s) (e.g., ontology or ontologies) on which the RKG is based. In the health care information domain, examples of canonical node types include, but are not limited to: disease, drug, FDA device code, FDA device name, geography (e.g., address, census region, city, country, county, geocoordinates, MSA code, state, zip code), health care organization, health care professional, hospital, manufacturer, procedure, industry event, and specialization. The canonical node types present in the canonical layer do not necessarily include all of the node types present in the multiple subgraphs of the RKG (i.e., there may be some node types present in one or more subgraphs that do not have a corresponding canonical node type in the canonical layer of the RKG).

The canonical layer of an RKG generally includes a quantity of canonical nodes that is less than (and sometimes significantly less than) the sum of all nodes present in the multiple subgraphs of the RKG. Each canonical node is unique in the canonical layer (it is only found once in the canonical layer); stated differently, each canonical entity is represented uniquely by only one node in the canonical layer. In some implementations, identical or closely related nodes to a given canonical node appear in at least two subgraphs in different namespaces of the RKG; in this case, at least one canonical node in the canonical layer is connected via multiple edges to at least two corresponding nodes in respective subgraphs in different namespaces of the RKG (and in some implementations all of the canonical nodes are connected to multiple subgraphs in this manner). In other implementations, a given canonical node may be identical or closely related to, and hence connected via an edge to, a subgraph node that only appears in one namespace of the RKG; however, such a canonical node may nonetheless be of particular significance in the information domain(s) such that it is expected to be connected to one or more new subgraph nodes at a future time (e.g., as one or more additional datasets pertaining to the information domain(s) are added to the RKG in corresponding new namespaces).

In another aspect, each edge between a canonical node in the canonical layer and a node in one or more subgraphs of the RKG is one of the following types: "is," "is part of," or "contains." In some implementations, the direction of an edge between a node in one or more subgraphs and a canonical node may be toward the canonical node, but in other implementations the direction of an edge may be from the canonical node to one or more subgraph nodes.

Within the canonical layer of an RKG, a given canonical node may be connected to one or more other canonical nodes via respective edges of a wide variety of types, based at least in part on the diverse relationships that may exist between canonical nodes of the same type or different types. In some instances, edges between subgraph nodes and canonical nodes, or between any two canonical nodes, may be generated based on trained models that predict (based on a variety of criteria coded in logic for the model) that the nodes should be connected (with some corresponding probability).

Artificial Intelligence-Artificial intelligence (AI) is an area of computer science relating to the creation of intelligent machines that work and react like humans, sometimes referred to as "intelligent agents." Some of the activities computers with artificial intelligence are designed for include, but are not limited to, gaining knowledge, reasoning, perception (e.g., speech recognition), learning, planning, problem solving, and manipulating objects. Knowledge engineering is a core part of AI research and the design of intelligent agents; such agents can be designed to act and react like humans only if they have abundant information relating to the world. Artificial intelligence must have access to information regarding various entities (e.g., objects, categories, properties) and relationships between entities, to implement knowledge engineering. Intelligent agents often are designed based on one or more algorithms (i.e., a set of unambiguous instructions that a computer can execute). A complex algorithm for a given intelligent agent is often built on top of other, simpler, algorithms. Many AI algorithms are capable of learning from data; they can enhance themselves by learning new heuristics (strategies that have worked well in the past) or can themselves write other algorithms.

Machine Learning-Machine learning (ML) is a branch of artificial intelligence based on the idea that systems (e.g., intelligent agents) can learn from data, identify patterns and make decisions with minimal human intervention. Thus, ML relates to algorithms and statistical models that intelligent agents use to progressively improve their performance on a specific task. In more formal terms, an intelligent agent based on an ML model learns from experience Æ with respect to some class of tasks T' and performance measure P if its performance at tasks in T, as measured by P, improves with experience E.

Machine learning tasks conventionally are classified into multiple categories. In "supervised learning," an ML algorithm builds a mathematical model of a set of "training data" that contains both the inputs and the desired outputs from performing a certain task. For example, if the task were determining whether an image contained a certain object, the training data for a supervised learning algorithm would include images with and without that object (the input), and each image would have a label (the output) designating whether it contained the object. "Semi-supervised learning" algorithms develop mathematical models from incomplete training data, where a portion of the sample inputs are missing the desired output. "Classification" algorithms and "regression" algorithms are types of supervised learning. Classification algorithms are used when the outputs are restricted to a limited set of values (e.g., represented by the Boolean values one and zero), whereas regression algorithms have continuous outputs (e.g., any value within a range of values).

In "unsupervised learning," an ML algorithm builds a mathematical model of a set of data which contains only inputs and no desired outputs. Unsupervised learning algorithms are used to find structure in the data, like grouping or clustering of data points. Unsupervised learning can discover patterns in the data, and can group the inputs into categories, as in "feature learning." "Dimensionality reduction" is the process of reducing the number of "features" (e.g., inputs) in a set of data. "Active learning" algorithms access the desired outputs (training labels) for a limited set of inputs based on a budget and optimize the choice of inputs for which it will acquire training labels. When used interactively, these inputs can be presented to a human user for labeling ("annotation").

Examples of various ML models known in the relevant arts include, but are not limited to, Linear Regression, Logistic Regression, Decision Tree, Support Vector Machine, Naive Bayes, kNN, K-Means, and Random Forest.

Natural Language Processing-Natural language processing (NLP) is a subfield of artificial intelligence (AI) concerned with the interactions between computers and human (natural) languages (e.g., how to program computers to process and analyze large amounts of natural language data). NLP generally relies on machine learning (ML) to learn rules for processing languages through the analysis of text corpora (e.g., large and structured sets of documents) of typical real-world examples (that may have human or computer annotations). Various classes of ML algorithms have been applied to NLP tasks. These algorithms generally take as input a set of "features" that are generated from the input data. For supervised learning algorithms, the input to the algorithms also includes one or more labels (outputs). NLP research has increasingly focused on statistical models, which make probabilistic decisions based on attaching real-valued weights to each input feature. Such models have the advantage that they can express the relative certainty of many different possible answers rather than only one, generally producing more reliable results when such a model is included as a component of a larger system.

Feature Representation/Feature Function/Featurization: In natural language processing (NLP), a "feature representation" is a structured mathematical representation for text that is suitable for input into a machine learning system. A feature representation is generated by applying one or more "feature functions" to the text in question to translate the text to the feature representation (this translation process is sometimes referred to as "featurization"). The feature representation determines what information a machine learning algorithm has access to regarding the text. Thus, in one aspect, the predictive value of the feature representation to a machine learning algorithm may be based, at least in part, on the complexity of the feature representation (e.g., a simpler mathematical representation for the text generally has less predictive value to the machine learning algorithm).

To provide an illustrative example of feature representation using the analogy of a house in place of a span of text, consider a machine learning model that makes a prediction about how long it will take for a house to sell. Houses, like text, are complex real-world objects that cannot, of course, themselves be processed by a computational algorithm. Thus, the house needs to be "featurized," i.e., a "feature function" needs to be applied to the house to generate a feature representation for the house. Such a feature representation may be relatively simple, e.g., a feature function may be applied to the house to generate a feature representation that includes a single numerical value corresponding to the size of the house. The predictive value of this feature representation for the house, however, will be limited. Alternatively, a feature function may be designed to generate a more complex feature representation for the house; for example, the feature function might generate a vector of numbers respectively representing the number of bathrooms in the house, the previous sales price for the house, the house's proximity to a train station, etc. Such a vector of numbers representing a given house includes significantly more information and allows a machine learning algorithm to make significantly more nuanced and accurate predictions.

Applying the above analogy to a string of text, a string like "Discontinue Advil due to cost" cannot be understood properly by a computer in its raw text form. Instead, one or more feature functions are applied to the text to generate a feature representation that may be processed by a machine learning algorithm. This feature representation may include significant information about the string (e.g., the number of words and various lexical properties of those words).

Feature Engineering—"feature engineering" refers to the process of defining an implementing feature functions.

NLP Model—an "NLP model" is any machine learning (ML) algorithm that processes feature representations derived from text (and optionally other types of data not necessarily relating to text). In one aspect, a given NLP model may include one or more feature functions that translate text to the feature representations that are processed by the NLP model.

Document—a "document" is an electronic file that includes unstructured data in the form of text. In other aspects, a document may include one or more of 1) other unstructured data and 2) some amount of structured data (e.g., metadata associated with the text in the document). Accordingly, a given document includes some amount of unstructured data that may in some instances be accompanied by some amount of structured data. In this respect, some documents may be referred to as including semi-structured data.

In the health care domain, a common example of a document is an "electronic health record" (EHR) (also referred to as an "electronic medical record" or "EMR;" for purposes of the present disclosure, the terms EHR and EMR are used interchangeably). An EHR includes a variety of health-related information pertaining to a patient or population. Examples of data that may be included in an EHR include, but are not limited to, demographic information, medical history, medication and allergies, immunization status, laboratory test results, radiology images, vital signs, personal statistics (e.g., age and weight), and billing information. Some or all of the foregoing data may be codified as structured data (e.g., in specific fields of the EHR) or semi-structured data. An EHR also includes some amount of unstructured data, for example, in the form of text created by one or more health care providers relating to specific encounters in health-related settings (e.g., office visits, hospitals, ambulatory environments, clinical trials/medical studies).

Annotation/Annotator—an "annotation" refers to any electronic information that is added to a document, typically during a process of reviewing, analyzing, categorizing, and/or otherwise organizing various data in the document. In some examples, annotations identify certain entity types and corresponding entities in a document and, optionally, attributes of entities, relationships between entities, and/or attributes of such relationships. An "annotator" is anything that produces an annotation; a "manual annotator" is a human that creates annotations, whereas an "automatic annotator" is an apparatus (e.g., a computer executing a machine learning algorithm/statistical model) that automatically creates annotations without human intervention.

Annotation Label—an "annotation label" (also referred to herein simply as a "label") is a text string used in an annotation that identifies an entity type for an entity mentioned in the text of a document. An annotation label also may be used in an annotation that specifies a relationship between two entities mentioned in the text of a document. In addition to a text string constituting the label, a given annotation label may be associated with or include one or more label attributes (e.g., additional descriptive text, highlighting and/or various colors, particular font styles, various shapes for an outline around the text of the label). For example, in some implementations relating to automatic annotators, an annotation label may include a confidence value representing a probability with which an automatic annotator correctly identified a given entity type for an entity mentioned in the text of a document.

Span—a "span" is a set of consecutive characters in the text of a document. Given a string of consecutive characters s in the text document, the notation s [m:n] denotes a unique span in s beginning at character m and extending up to, but not including, character n (according to the common convention in computer science using 0-based indexing). Thus, for the string of characters s=The dog barked, the span s [0:3] is the word "The" and the span s [4:7] is the word "dog." It should be appreciated that multiple words, as well as the full text associated with a given document, may be designated as a span; if the full text is designated as the string of characters s, and the total number of characters in s is N, then the span representing the full text is given by s [0:N].

Spannotation—a "spannotation" is an annotation of a span of text in a document, in which the span mentions an entity having a particular entity type. In some examples, a spannotation particularly identifies in some manner the span mentioning the entity (e.g., by highlighting the span with shading and/or a particular color, changing a color of characters in the span, changing font style for characters in the span). A spannotation also includes an annotation label adjacent to the identified span, wherein the annotation label provides the entity type for the entity (or the "concept") mentioned in the span. A "multi-spannotation" refers to a set of multiple non-contiguous spans that collectively relate to a same entity; these multiple non-contiguous spans are identified in a same manner (e.g., by highlighting the multiple non-contiguous spans in a same color and/or font style), and a single annotation label denoting the entity type or concept is provided for the multiple spans. For example, in the text "Patient has arm and leg fractures," the span "leg fractures" refers to a first entity and may be identified with a spannotation having a label "Diagnosis," and the non-contiguous spans "arm" and "fractures" collectively relate to a second entity and may be collectively identified with a multi-spannotation having a single label "Diagnosis." In some implementations, an entity type in a given spannotation or multi-spannotation may correspond to a canonical node type of an RKG.

Spannotation Relation—a "spannotation relation" (also referred to simply as a "relation") is an annotation that connects two spannotations, two multi-spannotations, or a spannotation and a multi-spannotation. Like spannotations and multi-spannotations, a relation generally has a label (e.g., that denotes the type of relationship between the entities identified in the spannotations/multi-spannotations), and the label may have one or more attributes. A relation may be directed or undirected; when a relation is directed, the first spannotation/multi-spannotation is referred to as the "origin" and the second spannotation/multi-spannotation is referred to as the "target." For example, in the document text "Discontinue Advil due to cost," a first spannotation for the span "Advil" (first entity=Advil) may include the label DISCONTINUED_DRUG (denoting the first entity type), and a second spannotation for the span "due to cost" (second entity=cost) may include the label CARE_OBSTACLE (denoting the second entity type). To capture the semantic connection between these two spannotations, a directed spannotation relation can be added having a label REASON, with the origin being the first entity "Advil" and the target being the second entity "due to cost."

Annotation Project—an "annotation project" refers to a process in which multiple documents are processed by one or more annotators to provide spannotations, multi-spannotations, and/or spannotation relations for the multiple documents. In one aspect, an annotation project is designed to identify certain entity types and corresponding entities that appear to be germane to a particular use-case (e.g., a specific situation in which a product or service could potentially be used, such as "hospital readmission for heart failure patients") or business question (e.g., exploring factors that influence a use-case, such as "what factors influence hospital readmission for heart failure patients?"). For example, an annotation project may structuralize explicit information present in unstructured data contained in one or more documents, and/or expose latent information in unstructured data, to provide significant insight toward identifying, clarifying and/or supporting a use-case and/or answering a business question.

Project Dataset—a "project dataset" includes a set of documents for an annotation project. Generally, the documents are related to each other in some manner. For example, in some instances, respective documents may have a related theme or common aspect (e.g., the documents are all created or provided by a particular source and/or at a particular location; the documents are created according to a particular recording method; the documents concern related or similar subjects). However, in other instances, there may be no particular unifying theme for the documents in a project dataset (e.g., the project dataset may include a random sample of documents from multiple sources). In the health care domain, examples of project datasets include, but are not limited to, EHRs from a particular hospital, medical department or medical practice, anonymized patient records from a particular clinical trial or medical study, scientific papers, patient survey texts, social media texts, commercial reporting and marketing documents, sales notes, and notes created by medical science liaisons.

Annotation Scheme—an "annotation scheme" is a set of annotation labels for spannotations, multi-spannotations and/or spannotation relations that are developed and used in an annotation project. An annotation scheme also may include one or more constraints on where spannotations, multi-spannotations and/or spannotation relations may appear in a given document. For example, if the set of labels for an annotation scheme includes the labels {DRUG, DOSAGE} for spannotations/multi-spannotations and the label {PRESCRIPTION_COMPONENT} for relations, an example of a constraint for the annotation scheme specifies that every spannotation/multi-spannotation having the label DOSAGE must be connected via the relation PRESCRIPTION_COMPONENT to a spannotation/multi-spannotation with the label DRUG. An annotation scheme may be specified with precision and may be implemented computationally so as to be machine readable (such that the annotation scheme may employed as the basis of one or more NLP models for an automatic annotator).

Annotation Guidelines—"annotation guidelines" refers to one or more instructions describing how a manual annotator should use a particular annotation scheme to annotate respective documents of a project dataset. Annotation guidelines may be informal in nature and are generally not machine readable.

Lexicon—a "lexicon" is a list of text strings, optionally with associated metadata, relating to one or more entities of a particular entity type. In one aspect, a lexicon may include synonyms, acronyms and/or rephrasings for a given entity having the particular entity type; for example, a "disease lexicon" may include a list of text strings including multiple variations of names for respective diseases. In another aspect, some or all of the text strings in a lexicon may be paired with other information or identifiers (e.g., "codes" from one or more predefined code-sets) relating to the one or more entities of the particular entity type (e.g., one or more text strings relating to a particular disease may be paired with an identifier or code for the disease as specified in one or more ontologies relating to diseases). In this respect, a lexicon also may include information about one or more entities that is derived from ontological relationships or real-world relationships. In yet another aspect, a given lexicon may be obtained as the result(s) of one or more queries of a Roam Knowledge Graph (RKG), wherein the text strings of the lexicon (and, if present in the lexicon, various related ontological information, identifiers, codes and/or metadata relating to the text strings) are obtained from one or more canonical nodes in the canonical layer of the RKG and one or more nodes in one or more subgraphs of the RKG connected to the one or more canonical nodes. In this context, the lexicon may be referred to as an "RKG-based lexicon."

Extractor—an "extractor" is an NLP model built from an RKG-based lexicon and used to process a string of characters. In particular, given a string of characters s as input, an extractor finds all of the spans in s mentioning an entity that statistically matches one of the text strings in the lexicon from which the extractor was built. Thus, in one aspect, an extractor predicts matches between spans and contents of an RKG-based lexicon with some appreciable degree of certainty (probability). In the context of annotation, an extractor may be the basis of an automatic annotator to provide one or more spannotations, multi-spannotations, and/or spannotation relations in a document. For example, an extractor based on an RKG-based disease lexicon may be employed to automatically process one or more documents to identify mentions of diseases in the lexicon, generate spannotations or multi-spannotations for the respective mentions of the identified diseases, and optionally generate one or more spannotation relations between spannotations/multi-spannotations. In one aspect, as noted above, the annotation label for a spannotation, multi-spannotation, or spannotation relation automatically generated by an extractor may include a confidence value representing a probability with which the extractor correctly identified the entity mentioned in the span. In another aspect, spannotations, multi-spannotations, and/or spannotation relations automatically generated by an extractor may have one or more particular attributes denoting that they were automatically generated (e.g., a particular text and/or highlighting color may be assigned to automatically annotated spans). In yet another aspect, a given extractor may be designed to automatically identify entities of a given entity type corresponding to any of the canonical node types in the canonical layer of an RKG.

Project NLP Target Model—a "project NLP target model" is an NLP model based on supervised learning that is trained in connection with an annotation project on annotations made at least in part by manual annotators, according to the annotation scheme for the annotation project, on some number of documents in the project dataset for the annotation project. Rather than string matching, a project NLP target model featurizes its inputs and uses learned weights for feature representations to assign new annotations. In particular, a trained project NLP target model processes other unannotated documents in the project dataset to automatically generate spannotations, multi-spannotations, and/or spannotation relations in the other documents according to the annotation scheme. In one aspect, a project NLP target model for a given annotation project may be iteratively trained on successive sets of manually annotated documents in the project dataset to improve a performance of the project NLP target model (i.e., increase the statistical likelihood that the project NLP target model is correctly generating spannotations, multi-spannotations, and/or spannotation relations in remaining unannotated documents of the project dataset, according to the annotation scheme). In another aspect, one or more extractors can be the basis of one or more feature functions of a project NLP target model. In yet another aspect, as discussed above in connection with extractors, the annotation label for a spannotation, multi-spannotation, or spannotation relation automatically generated by a project NLP target model may include a confidence value representing a probability with which the model correctly identified the entity mentioned in the span.

Preannotation—a "preannotation" is a spannotation, multi-spannotation, or spannotation relation that is generated in documents of a project dataset by an automatic annotator in advance of annotation by a manual annotator. In one example, an extractor may serve as an automatic annotator to generate one or more preannotations. In another example, a project NLP target model that was previously trained in connection with another prior annotation project may be "re-used" in a new annotation project as an automatic annotator to generate one or more preannotations. In yet another aspect, it should be appreciated that the entity/entities and entity type(s) that a given extractor and/or previously-trained project NLP target model are designed to identify in documents may or may not be the same as one or more entity types corresponding to the annotation labels of an annotation scheme that is developed for the project dataset. Rather, more generally, one or more automatic annotators may be employed for preannotation to identify various entities and entity types so as to facilitate preliminary exploration of the dataset (e.g., by one or more domain experts/human annotators, data scientists, and/or NLP engineers); in this sense, the preannotations may be heuristic in nature, which does not necessarily require alignment of the entity types identified by the automatic annotators with the entity types corresponding to the annotation labels in the annotation scheme that is ultimately developed for the project dataset.

"Alpine" Annotation Manager (AM) Overview

Various inventive concepts discussed in detail herein are directed to an Annotation Manager (AM), which is an integrated system (including one or more computers executing code) that enables experts in a particular information domain to autonomously (or semi-autonomously) design and run annotation projects for natural language processing (NLP) applications. In the present disclosure, such a system is also referred to as "Alpine." Alpine employs inventive and intuitive methods for annotation of unstructured text documents (or semi-structured documents including free-form text) in a given information domain, as well as inventive techniques for developing and training NLP models to extract structured information from free-form text. In other aspects, Alpine significantly facilitates collaboration amongst multiple human annotators who are skilled experts in the particular information domain to which the documents of an annotation project dataset pertain; using Alpine, such experts can explore data via sophisticated search functions, discuss annotation policies (e.g., annotation schemes and annotation guidelines), capture these discussions electronically, annotate text in an active learning workflow, adjust annotation policies in real-time as an annotation project evolves, and study the resulting annotated documents.

More specifically, unlike conventional annotation tools, Alpine enables annotators to rapidly explore documents in a project dataset as they contemplate an annotation scheme for the dataset. Using Alpine, annotators can discuss (via embedded electronic communication functionality) more difficult "edge" cases for categorizing text, resolve conflicts or disagreements between examples of the same text annotated by different annotators during exploratory annotations, debate the merits of using specific entity types and label names—and capture valuable information relating to all of these activities and deliberations in real-time as an annotation project evolves. This ability to electronically preserve and memorialize the formative stages of an annotation project allows for iterative development of more effective and robust annotation schemes and annotation guidelines. Alpine also provides for creation, customization, and easy editing of annotation labels for annotation schemes during an annotation project; in particular, in one implementation, any edits to a particular annotation label may be automatically propagated to all prior annotations with that label.

Thus, Alpine is a fully-integrated annotation tool kit that enables domain specialists and/or highly-skilled experts to quickly translate a complex use case or business question relating to a project dataset into a customized set of NLP annotations and models for respective documents of the dataset. Moreover, Alpine's inventive functionality permits adjustments and updates to annotation labels, annotation schemes, and/or NLP models without the need of significant (if any) support from engineering or data science resources.

Figure 33:
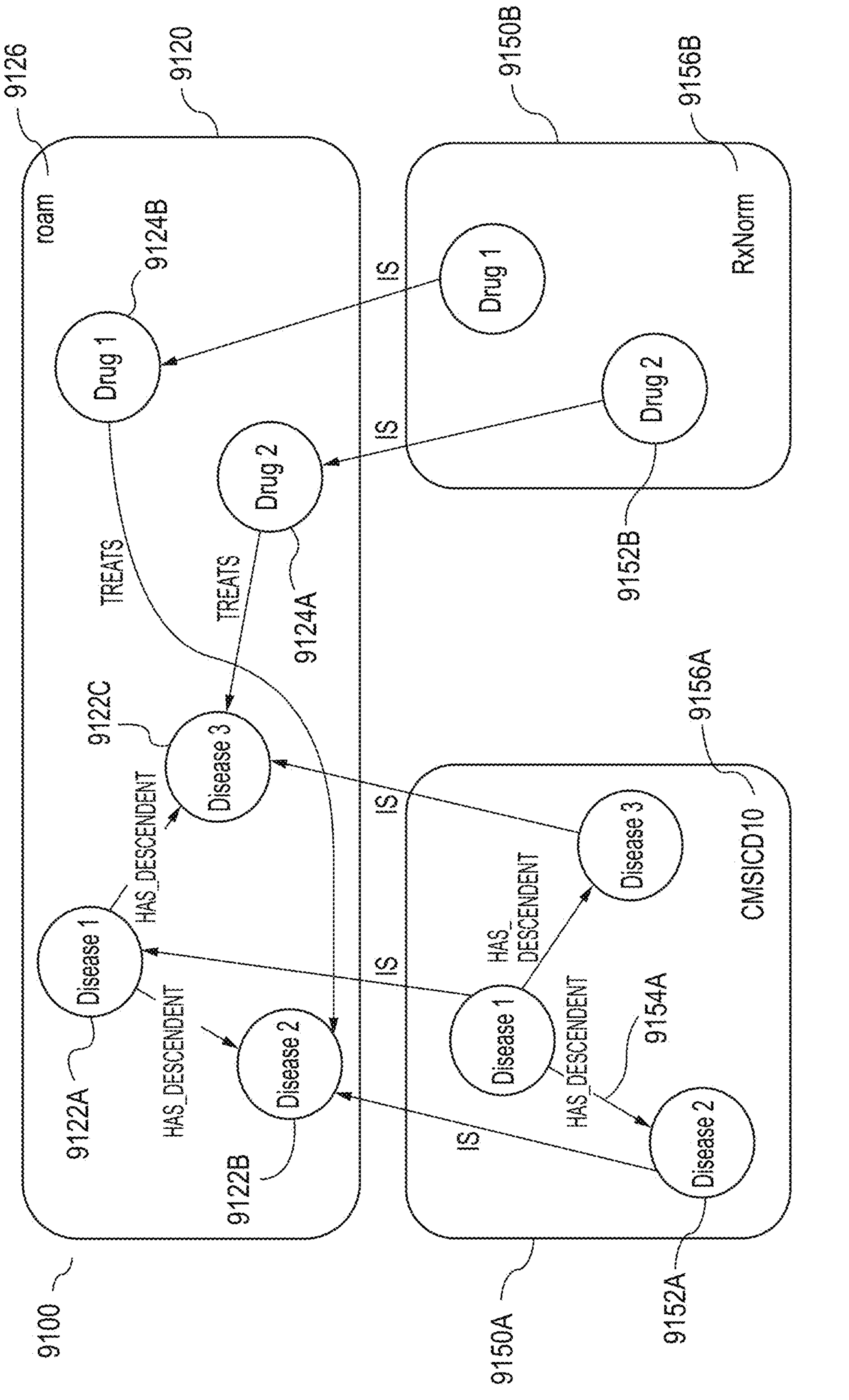
FIG. 33 illustrates an example of an inventive graph-based data storage and retrieval structure referred to herein as a Roam Knowledge Graph (RKG), according to various implementations.

In some inventive aspects, Alpine can be enhanced by utilizing various information derived from a Roam Knowledge Graph (RKG), described in detail further below. As illustrated in FIG. 33, an RKG includes multiple subgraphs representing corresponding datasets that pertain to a particular domain of interest. Each of the subgraphs is linked to a canonical layer (also referred to herein as a "linking layer" or "semantic layer") of the RKG. The canonical layer generally serves to strategically interconnect and unify information in the underlying datasets represented by the respective subgraphs of the RKG to provide broader context for the information and facilitate querying and discovery of relationships in the information.

In some implementations, an RKG can be used to develop lexical resources that may be subsequently employed by the Alpine Annotation Manager to facilitate annotation projects. For example, in one implementation, documents in an annotation project dataset may be explored and preannotated (prior to initial annotation by manual annotators) using one or more lexicons and/or NLP models referred to as "extractors." In some examples, such extractors are built on lexical resources harvested from an RKG and are employed in Alpine to process respective documents of the annotation project dataset to automatically find and label certain entity types ("concepts") mentioned in the documents. In one aspect, one or more extractors enable domain experts to quickly filter project documents and efficiently use their time and expertise (e.g., based in part on the entity types that the extractors are designed to automatically identify). Highly skilled experts/annotators can review/modify these preannotated documents to develop an annotation scheme for the project at hand.

In some inventive aspects, depending in part on the annotation project dataset and the use-case or business question at hand, Alpine may be employed to meaningfully represent unstructured text documents with annotations that correspond to information (e.g., entity types or "concepts") present in the canonical layer of an RKG. In this manner, the structured information derived from the annotations of the documents in the annotation project dataset can be readily coupled to the existing RKG, benefit from the broader context of RKG, and the RKG itself can be augmented with the structured information extracted from the text documents of the project dataset to provide greater context for the overall information domain of interest.

Alpine's Annotation User Interface (AUI)

Functionalities Provided by AUI

FIG. 1 illustrates a first graphical user interface (GUI) 100 (also referred to herein in some instances as a "screen shot") of Alpine's Annotation User Interface (AUI), showcasing various functionalities that the AUI can facilitate in order to autonomously design and run annotation projects for NLP applications. In the discussion below regarding various graphical user interfaces (GUI) that constitute the AUI of the Alpine Annotation Manager, it should be appreciated that one or more computers executing code cause the display of the respective GUIs of the AUI and, in some instances, accept various forms of input from a user viewing one or more of the GUIs (which input may in some aspects be related to or responsive to information displayed in one or more of the GUIs of the AUI). The one or more computers also perform various processing of the respective documents of an annotation project data set and, in some implementations, also facilitate NLP model building and training, according to the various functionalities described herein.

In the example implementation shown in the first screen shot 100 of FIG. 1, the AUI includes an "Explore" functionality 102 to facilitate exploration of at least some of the respective documents of an annotation project dataset, based on a search query including one or more entities/concepts of interest. In response to the search query, respective documents of the project dataset may be processed (queried) to look for the one or more entities/concepts of interest in the documents based on one or more lexicons (e.g., a list of text strings such as one or more synonyms, antonyms, rephrasings, identifiers and/or codes) relating to the one or more entities/concepts of interest in the search query. A given lexicon may be based on one of any number of ontologies (refer to Glossary above) to provide a rich set of text strings and/or codes that in some manner relate to an entity/concept of interest included in a search query; alternatively, a given lexicon may be an RKG-based lexicon derived from querying a Roam Knowledge Graph (RKG). In particular, RKG-based lexicons may serve as the basis of one or more NLP models (also referred to herein as "extractors"-refer to Glossary above) that may be employed to process the respective documents of a project dataset to facilitate exploration.

As a result of processing the documents based on one or more lexicons and/or one or more NLP models, the respective documents of the project dataset may be categorized and displayed to facilitate exploration of the contents of documents in the project dataset. Furthermore, in some implementations, one or more documents of the project dataset may be preannoatated (refer to Glossary above) as part of the processing based on one or more lexicons and/or one or more NLP models; as discussed further below, a document that is preannotated pursuant to the "Explore" functionality 102 of the AUI may be subsequently displayed as part of the "Annotate" functionality, discussed immediately below, to orient and otherwise facilitate annotation of the document.

As illustrated in the first screen shot 100 of FIG. 1, the AUI may also include an "Annotate" functionality 104 to facilitate one or more domain experts to manually annotate documents in a project dataset via multiple integrated graphical user interfaces (GUIs) serving as an innovative GUI-based annotation tool. The "Annotate" functionality 104 enables domain experts and/or annotators to analyze the documents in a project dataset, contemplate and decide on annotation guidelines and an annotation scheme for the project dataset, annotate the documents in the project dataset via intuitive and specialized graphical user interfaces, compare annotations by other domain experts and/or annotators, and resolve conflicts if any. The "Annotate" functionality 104 provides for iterative development of an effective and robust annotation scheme and annotation guidelines. Moreover, this functionality can allow for creation, customization, and easy editing of annotation labels.

As also shown in FIG. 1, the AUI can also include a "Build" functionality 106 to facilitate designing and/or training of one or more project NLP target models. More specifically, the "Build" functionality 106 can enable users, who need not necessarily be machine learning and/or NLP engineers or experts, to design and/or train project NLP target models. In example implementations, the annotations made in at least a subset of project dataset documents using the "Annotate" functionality 104 (and optionally the "Explore" functionality 102 as well) can be used as training data to design and/or train project NLP target models. Once a project NLP target model is trained and designed, this project NLP target model can then be used to automatically annotate other documents within the same project dataset and/or documents within a different project dataset (presumably involving a same or similar domain and associated entities/concepts). The automatically annotated documents (i.e., annotated by the project NLP target models) can then be analyzed and compared to determine if any corrections need to be made to the annotation scheme and/or the annotation guidelines. Once the corrections are made, the project NLP target model can be re-trained based on these corrections and can be used to annotate a larger number of documents in the project dataset. This iterative designing and training of a project NLP target model is referred to herein as an "active learning framework," which is discussed in detail in later sections of this document. The "Build" functionality 106 of the AUI 100 significantly facilitates access to this active learning framework, allowing users who may be experts in the domain to which the project dataset pertains, but not necessarily experts in machine learning or NLP, to nonetheless reliably and effectively design and train project NLP target models to automatically annotate larger numbers of documents in a project dataset.

High-Level Overview of Annotation and Model Training

As noted above, existing tools for annotating data are often focused exclusively on the act of assigning labels. Such tools tend to presuppose that the annotation guidelines are set in stone. The Inventors have recognized and appreciated that there is not a single tool for annotation projects that offers the "Explore," "Annotate," and "Build" functionalities together. Providing a GUI-based computer tool that includes these functionalities integrated together supports collaborative, non-linear workflows that are needed for successful annotation and enables domain experts to design and run annotation projects on their own. Via the Alpine AM and its AUI, a team of domain experts can operate independently of engineering teams, allowing the domain experts to work directly with project managers and customers when defining a custom annotation project for a specific use-case.

Figure 2A:
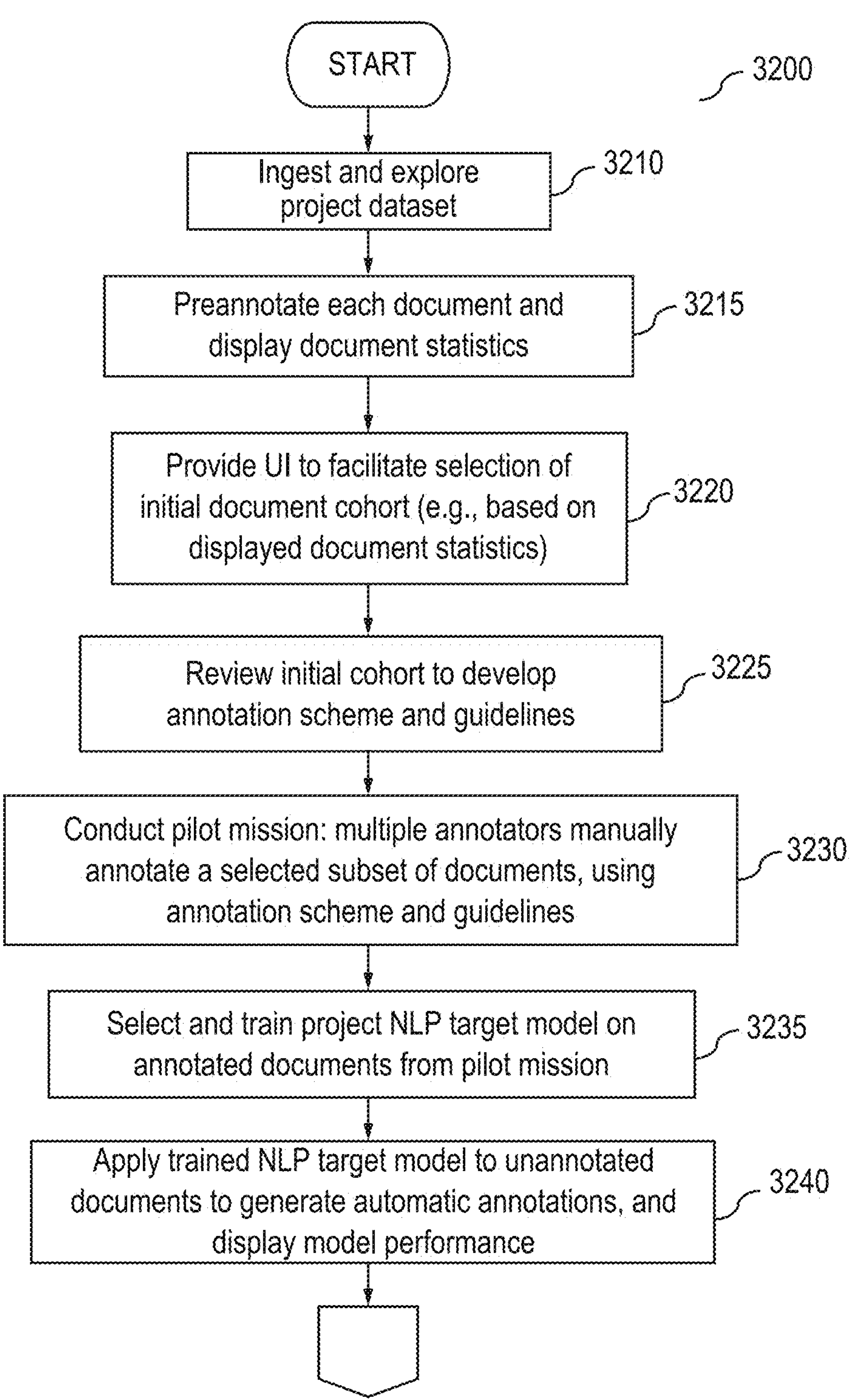
FIGS. 2A and 2B illustrate a flow diagram for an annotation method using the Alpine AUI, according to one inventive implementation.
Figure 2B:
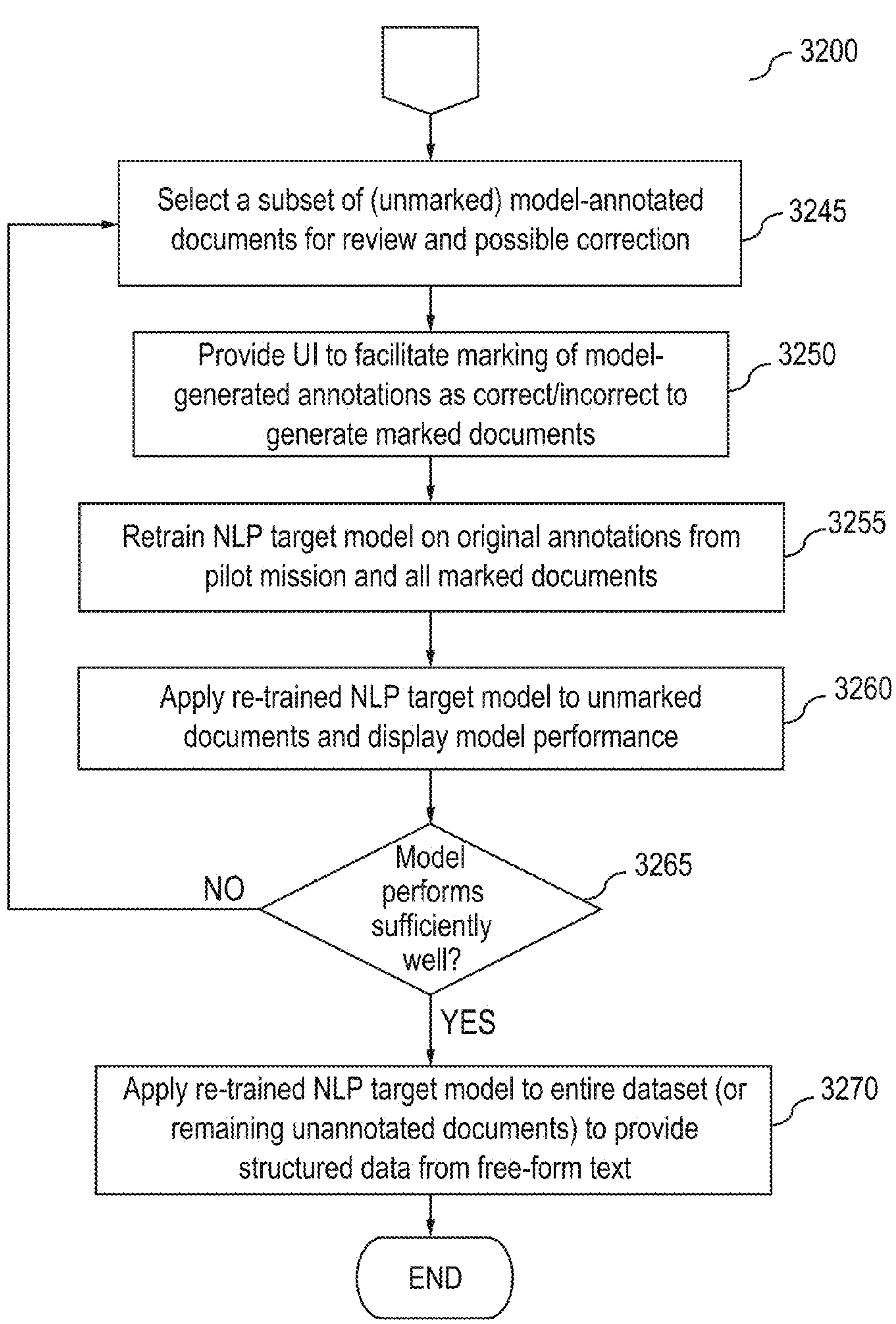

FIGS. 2A and 2B illustrate a flow diagram for an annotation and model training method 3200 including an "active learning workflow," as implemented by the Alpine AM including the AUI according to one example implementation. It should be appreciated that the flow diagram shown in FIGS. 2A and 2B provides an introductory overview of various aspects of an annotation and model training method, and that these various aspects of the method are explained in additional detail following the introductory overview.

At 3210 in FIG. 2A, the Alpine AM can ingest a project dataset, and then the AUI can be used to explore the project dataset (via the "Explore" functionality 102 discussed above in connection with FIG. 1). In some examples, a project dataset pertaining to the domain(s) of interest may be downloaded (e.g., from the Internet or a private server of a particular source of the dataset) and imported into a corresponding isolated namespace of computer storage (which namespace may be labeled, based at least in part, on the source of the dataset). In some examples, one or more files in a dataset may be downloaded via the Internet from a website that provides a portal to an Internet-coupled server or servers maintained by (or providing hosting services to) the source of the dataset. In one example implementation, the method employs conventional techniques to crawl the Internet and download the one or more files relating to the dataset. In some instances, multiple files for a given dataset are obtained from the source as zipped files, and/or the file(s) may be in a particular file format or different file formats (e.g., .csv, .json).

The ingested project dataset may then be explored via the "Explore" functionality 102 introduced above in connection with FIG. 1 and discussed further below in connection with FIGS. 5-9. In particular, one or more lexicons and/or NLP models may be employed by the Alpine AM to enable sophisticated search functionality for document exploration. As indicated at 3215, in some implementations each document in the project dataset can be preannotated and categorized, and respective document statistics can be displayed according to various categorizations as part of the "Explore" functionality 102.

Based on the document statistics and categorizations, as indicated at 3220 of FIG. 2A, one or more GUIs of the AUI provide for selection of an initial document cohort to develop an annotation scheme and annotation guidelines for the annotation project. At 3225, the initial document cohort can be reviewed and analyzed by annotators to develop an annotation scheme and annotation guidelines to annotate the documents in the project dataset via various GUIs of the AUI (e.g., via the "Annotate" functionality 104 in FIG. 1). At 3230, multiple annotators can be assigned to manually annotate a selected subset of documents in the project dataset as part of a "pilot mission;" during this phase, the annotation scheme and guidelines may be further developed and revised, in some instances by analyzing disagreements in annotations between the multiple annotators and subsequently applying conflict resolution. At 3235, the annotated documents from the pilot mission can be used to select and train a project NLP target model (e.g., via the "Build" functionality 106 in FIG. 1). At 3240, the initially-trained project NLP target model can be applied to unannotated documents of the project dataset to generate automatic annotations and display model performance.

Turning now to FIG. 2B, at 3245 a GUI of the AUI may be provided so that a subset of these model-annotated documents can be selected for review by the annotators; the model-annotated documents of this subset are referred to herein as "unmarked" documents. At 3250, one or more GUIs of the AUI may be provided to facilitate review of the unmarked documents and, if needed, correction by the annotators of one or more of the model-generated automatic annotations. The provision of one or more GUIs of the AUI to allow annotators to readily mark model-annotated documents so as to correct model-generated automatic annotations provides a significant technological improvement to the active learning framework for iteratively training NLP models—in this manner, the AUI provides a valuable GUI-based tool for generating marked documents (i.e., documents with annotator-marked corrections of model-generated automatic annotations) for iteratively training an NLP model.

To this end, at 3255 in FIG. 2B, the project NLP target model can be re-trained on original annotations and all marked documents (e.g., via the "Build" functionality 106 in FIG. 1). At 3260, the re-trained project NLP target model can further be applied to unmarked documents (e.g., another subset of model-annotated documents that has not yet been corrected by the annotators). At 3265, a determination can be made on if the model performs sufficiently well (e.g., via the "Build" functionality 106 in FIG. 1). If the model does perform sufficiently well, at 3270, the re-trained NLP target model can be applied to the entire project dataset (or remaining unannotated documents) to provide structured data from free-form text. If the model does not perform sufficiently well, then the method reverts back to step 3245.

Creating Annotation Projects with AUI

Figure 3:
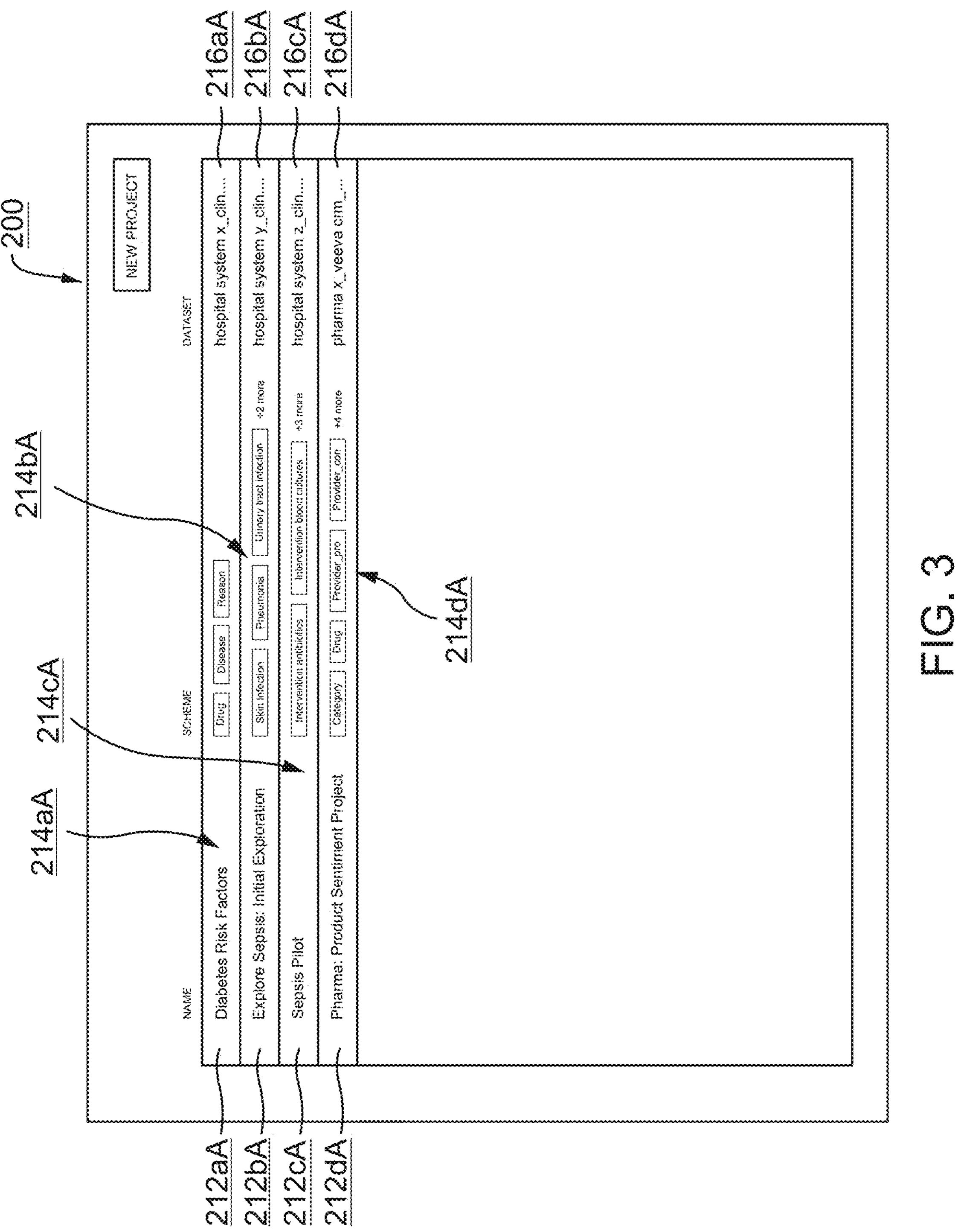
FIG. 3 illustrates a second screen shot of Alpine's AUI relating to an example list of annotation projects, according to one inventive implementation.

FIG. 3 illustrates a second screen shot 200 of Alpine's Annotation User Interface (AUI) relating to an example list of annotation projects (e.g., 'Diabetes Risk Factors" 212*a*A, "Explore Sepsis: Initial Exploration" 212*b*A, "Sepsis Pilot" 212*c*A, and "Pharma: Product Sentiment Project" 212*d*A), according to one inventive implementation. As illustrated in FIG. 3, each annotation project has an annotation scheme associated with it. For instance, in FIG. 3, annotation project 'Diabetes Risk Factors" 212*a*A has the annotation scheme {DRUG, DISEASE, REASON} 214*a*A associated with it. Each annotation scheme includes one or more annotation labels for spannotations (and optionally spannotation relations). For instance, annotation scheme {DRUG, DISEASE, REASON} 214*a*A includes labels for spannotations of entity types "Drug," and "Disease" and a spannotation relation label "REASON" to capture the connection between the spannotations "DRUG" and "DISEASE." As noted above and discussed in detail below, each annotation project generally is associated with one or more trained project NLP target models to automatically annotate the documents in the corresponding project dataset (e.g., 216*a*A-216*d*A) according to the annotation scheme for the project data set. These project NLP target models can be developed, improved (e.g., trained and retrained iteratively), and monitored using Alpine.

Figure 4:
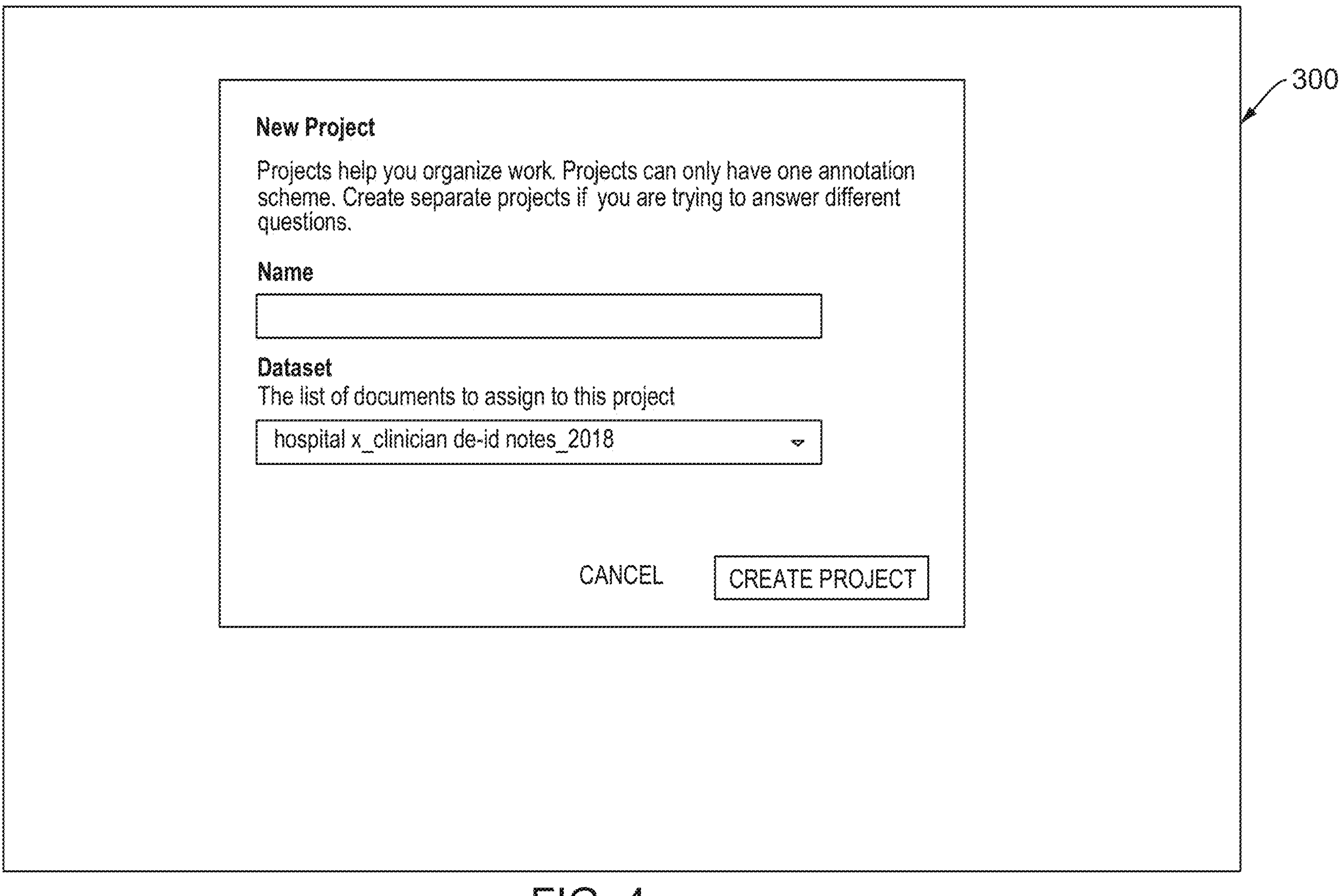
FIG. 4 illustrates a third screen shot of Alpine's AUI relating to creation of new annotations projects, according to one inventive implementation.

FIG. 4 illustrates a third screen shot 300 of Alpine's Annotation User Interface (AUI) relating to creation of new annotation projects, according to one inventive implementation. A creator of a new annotation project can give the project a name and specify the project dataset to be imported from a given source (e.g., in the health care domain, a source of a project dataset may be a medical provider or large hospital system). For purposes of illustrating some of the salient inventive concepts underlying the Alpine AUI, an example project dataset in the health care domain is considered. As noted above, however, it should be appreciated that project datasets for which Alpine may be employed to provide annotations and generate one or more project NLP target models may pertain to a variety of domains.

"Explore" Functionality

The "Explore" functionality 102 introduced in connection with FIG. 1 can facilitate searching, categorization (e.g., filtering, sorting), and preannotation of documents in an annotation project dataset. In some examples, the "Explore" functionality utilizes one or more lexicons and/or one or more NLP models to preliminarily search for one or more entities/concepts mentioned in at least some documents of a project dataset, to allow annotators to build an understanding of document contents and general scope of information and topics present in the project dataset.

In particular, the "Explore" functionality 102 facilitates exploration of at least some of the respective documents of an annotation project dataset based on a search query including one or more entities/concepts of interest. In response to the search query, respective documents of the project dataset may be processed (queried) to look for the one or more entities/concepts of interest in the documents based on one or more lexicons relating to the one or more entities/concepts of interest in the search query. As noted above in the Glossary, a "lexicon" may include a list of text strings such as one or more synonyms, antonyms, rephrasings, identifiers and/or codes relating to a given entity/concept.

In one aspect, searching the contents of documents of the project dataset based on one or more lexicons provides a more sophisticated and expansive search functionality. For example, a given lexicon may be based on one of any number of ontologies (refer to Glossary above) to provide a rich set of text strings and/or codes that in some manner relate to an entity/concept of interest included in a search query. Moreover, in some examples discussed further below (e.g., see the discussion in connection with FIG. 33 et seq.), a given lexicon may be an RKG-based lexicon derived from querying a Roam Knowledge Graph (RKG) (e.g., the information in an RKG-based lexicon may be obtained from one or more canonical nodes in a canonical layer of the RKG, and/or one or more nodes in at least one subgraph of the RKG). RKG-based lexicons also may serve as the basis of one or more NLP models (also referred to herein as "extractors"-refer to Glossary above) that may be employed to process the respective documents of a project dataset to facilitate exploration. In yet another example, in tandem with or in place of one or more lexicons, as part of the "Explore" functionality 102 respective documents of the annotation project dataset may be processed by one or more previously-trained NLP project target models relating to a prior annotation project, so as to facilitate exploration of the current annotation project dataset.

As a result of processing the documents based on one or more lexicons and/or one or more NLP models (e.g., extractors, previously-trained NLP project target models), the respective documents of the project dataset may be categorized (e.g., filtered and/or sorted) in some manner and displayed according to various categorizations to facilitate preliminary heuristic exploration of the contents of documents in the project dataset. Furthermore, in some implementations, one or more documents of the project dataset may be preannoatated (refer to Glossary above) as part of the processing based on one or more lexicons and/or one or more NLP models; as discussed further below, a document that is preannotated pursuant to the "Explore" functionality 102 of the AUI may be subsequently displayed as part of the "Annotate" functionality to orient and otherwise facilitate annotation of the document.

Extractors

As noted above and discussed in greater detail below (in connection with FIG. 33 et seq.), an RKG is a large knowledge graph that integrates numerous heterogenous data sources. In the context of Alpine and enhanced annotation techniques using Alpine, one illustrative use for an RKG relates to the development of lexical resources that facilitate exploration and automatic annotation of free-form text in documents. These lexical resources can be relatively straightforward, such as one or more lists of words relating to a particular entity or entity type; alternatively, the lexical resources developed using the RKG may include/encompass complex relationships between various information, such as a mapping from one or more words to nested key-value stores providing diverse metadata about those words.

Figure 5:
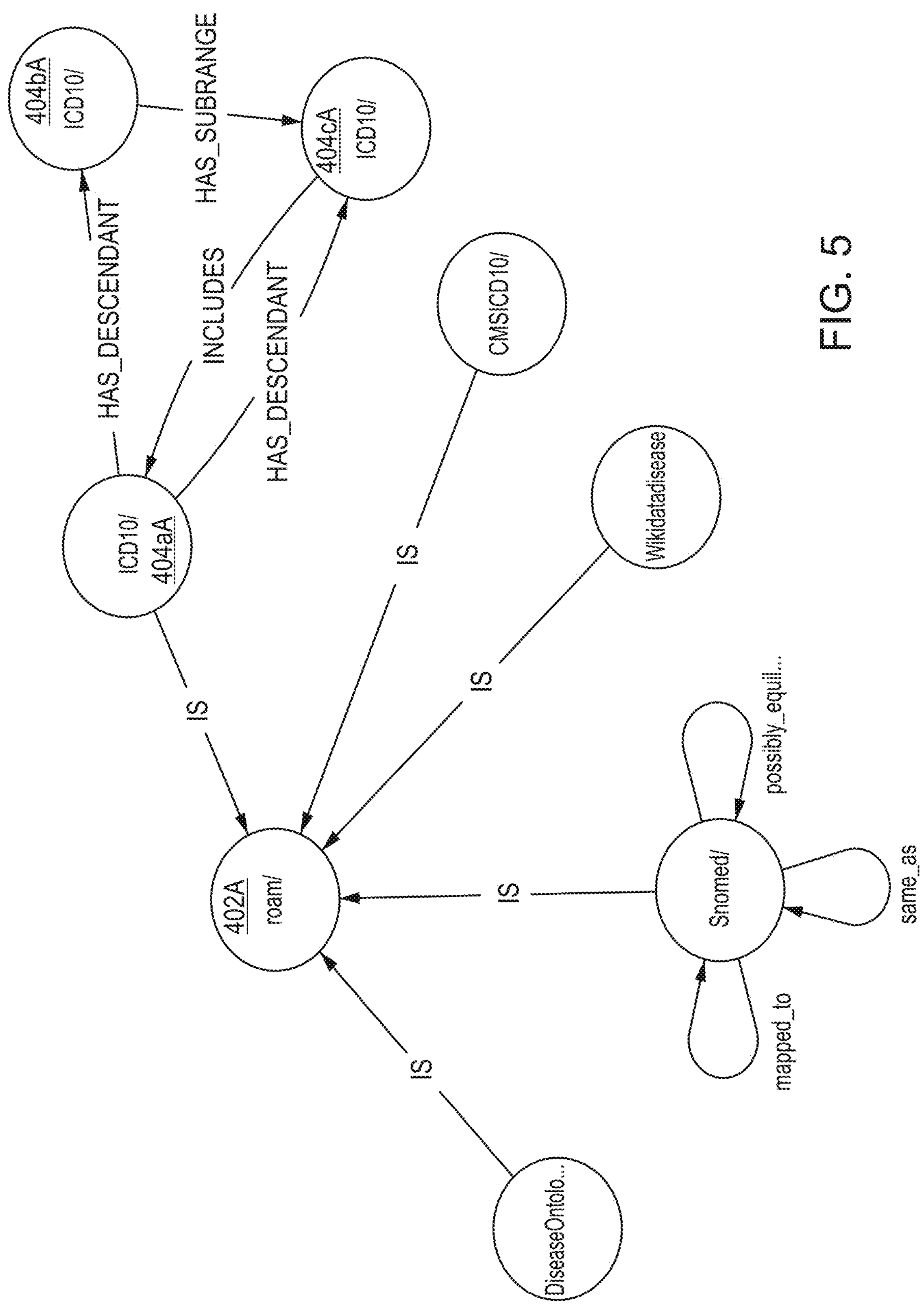
FIG. 5 illustrates an example of nodes and edges from a Roam Knowledge Graph (RKG) for developing lexical resources, according to various implementations.

These lexical resources can be used as a basis for NLP models (e.g., NLP project target models) that identify and/or aggregate diverse pieces of texts into more structured entities and connect these texts to more structured information. An RKG stores information that significantly facilitates creation and retrieval of various lexical resources that may serve as a basis for NLP models. In some inventive implementations, the canonical layer of an RKG plays a significant role in this process of creating and/or retrieving lexical resources that may be employed for NLP models. FIG. 5 illustrates this process with an example based on an RKG for the health care domain, in which the canonical layer of the RKG includes canonical nodes of the type roam/Disease.

More specifically, to capture all of the names for various diseases represented by nodes in the canonical layer of an RKG of the type roam/Disease 402A, one can query the RKG so as to access nodes in all of the adjacent namespaces connected to nodes of the type roam/Disease and harvest all of the name-type attributes from the nodes in the connected namespaces. Using the Cypher graph query language (as discussed further below), an exemplary graph query may take the form:

MATCH (d: 'roam/Disease')←[: IS]-(n)
RETURN d.code, n.name

The return value of such a query is a list of code-name pairs. For example:

E11 Type 2 diabetes
E11 T2D
E11 diabetes 2.
. . .

By grouping on the code values, a list of alternative names for the same code value can be obtained:

[E11: {Type 2 diabetes, T2D, diabetes 2, . . . }, . . . ]

In an RKG with several namespaces respectively corresponding to datasets including information about various diseases (e.g., based on one or more ontologies), many different spelling and naming variants for a given disease may be extracted from the RKG as lexical resources that could serve as an NLP model to find diverse mentions of the given disease in free-form text (e.g., based on an anchoring code for the given disease).

In the health care domain, and given various ontologies that may be represented by respective namespaces in an RKG, there may be different codes associated with the same disease. This may be codified as attributes on roam/Disease 402A nodes. Therefore, lexicons based around these code sets can be created by changing the attribute code in the above query. In some inventive aspects, other metadata may be optionally added at this stage by simply returning more graph values.

In some inventive aspects, a more informal lexicon can be created by relaxing standards for identity. For example, notice that the ICD10 nodes 404*a*A, 404*b*A, and 404*c*A form a hierarchy in FIG. 5. Names of ancestor nodes might also be appropriate as names for d in the query:

MATCH (d: 'roam/Disease')←[: IS]-(n)-[: HAS DESCENDANT]→(m) RETURN d.code, n.name, m.name In a similar manner, since several important health care entities such as diseases, procedures, devices, body parts etc., are situated in subgraphs of the RKG with the sort of structure seen in FIG. 5, lexicons can be created for all of them as well using the same logic and set of tools.

Lexical resources like the above can be used in many ways. For extractors, a mapping from names to compatible codes can be created:

[Type 2 diabetes: {E11}, T2D: {E11}, diabetes 2: {E11}]

With this resource created, the unstructured text in respective documents of an annotation project dataset can be explored via lexicons and extractors and preannotated using string matching with the keys of the map. Each match can be annotated with its corresponding code and perhaps also with a high-level classification like DISEASE (e.g., which can provide the text of an annotation label).

Example Graphical User Interfaces Provided by "Explore" Functionality

As part of the process for importing a project dataset into Alpine and providing access to respective documents of the dataset via the AUI, in some implementations Alpine automatically processes respective documents of the project dataset using one or more lexicons or "extractors" to provide preannotations for at least some of the documents in the dataset. In particular, using RKG-based lexicons, Alpine can search for specific terms within the documents based on a wide variety of information contained in an RKG. Lexical resources that group alternative names of the same term can also return documents within a project dataset that contain synonyms to the specific term. In addition to searching, these resources can aid in filtering and sorting documents within a project dataset. For instance, documents that include a specific term and/or synonyms of the specific term can be filtered out from the rest of the project dataset. In some instances, the preannotation can then be performed on the filtered set of documents.

Additionally, to the extent previously-trained NLP target models are available based on prior annotation projects and applicable in some manner to a new annotation project, in some implementations Alpine may apply one or more previously-trained project NLP target models (e.g., from prior annotation projects) to facilitate exploration and provide preannotations for the respective documents of the project dataset in a manner similar to that generated by RKG-based lexicons.

Figure 6:
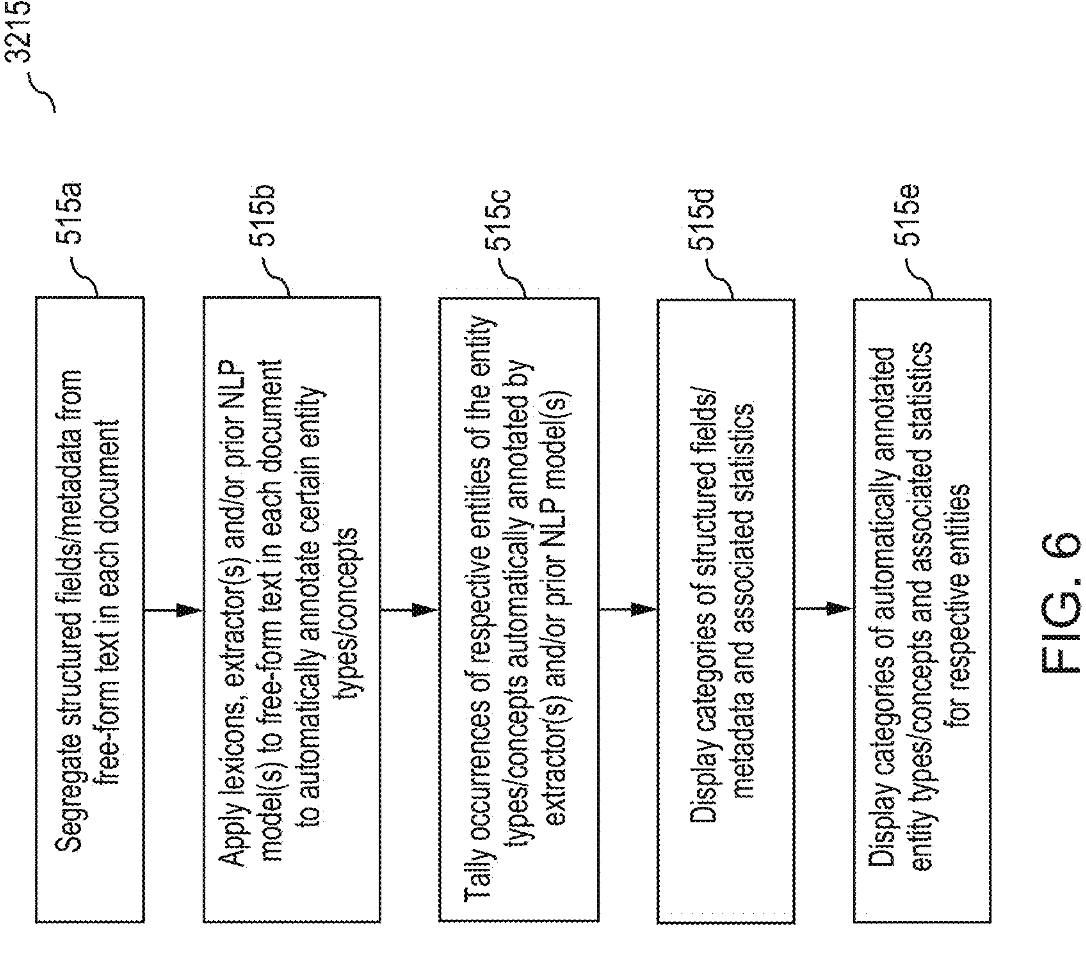
FIG. 6 illustrates further details relating to preannotation and display of document statistics in the method outlined in FIGS. 2A and 2B, according to one inventive implementation.

FIG. 6 is a flow diagram further illustrating a method 3215 with details relating to preannotation and display of document statistics in the method outlined in FIGS. 2A and 2B (e.g., via the "Explore" functionality 102 in FIG. 1), according to one inventive implementation. When documents of a project dataset are imported to Alpine, using the "Explore" functionality, at 515*a*, structured fields and/or metadata from each document in a project dataset can be segregated from the free-form text. At 515*b*, one or more lexicons, extractors and/or previously-trained NLP target models can be applied to the free-form text in each document to automatically annotate certain entity types/concepts. In some implementations, these lexicons, extractors and/or previously-trained NLP target models can also be applied to filter and/or sort documents in a project dataset. In some implementations, lexicons, extractors and/or previously trained NLP target models can be applied to search for specific terms and/or synonyms of the specific terms in the documents of the project dataset.

Once the entity types/concepts are automatically annotated using the lexicons, extractors and/or previously-trained NLP models, at 515*c*, the "Explore" functionality can facilitate tallying occurrences of respective entities of the entity types/concepts. At 515*d*, the categories of structured fields/metadata and associated statistics can be displayed on the graphical user interface. These statistics can include the total number of documents in which a specific structured field/metadata occurs in a project dataset. At 515*e*, the categories of automatically annotated entity types/concepts and the associated statistics for respective entity types/concepts can also be displayed on the graphical user interface.

Figure 7:
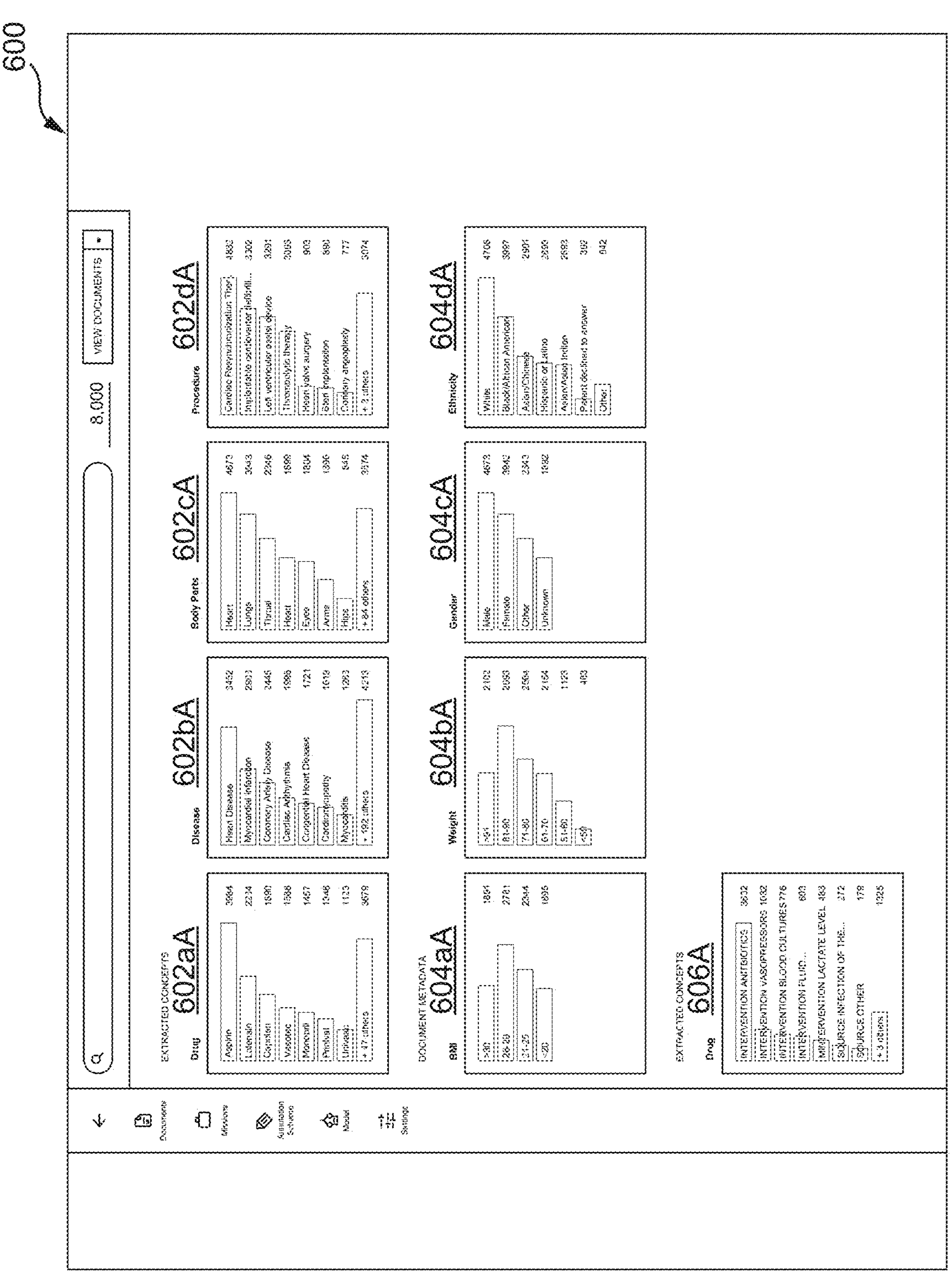
FIG. 7 illustrates a fourth screen shot of the AUI showing how respective documents of an imported project dataset have been explored and categorized, according to one inventive implementation.

FIG. 7 illustrates a fourth screen shot 600 of the Alpine AUI showing how respective documents of an imported project dataset have been automatically processed to provide preannotations and how these documents have been accordingly categorized, according to one inventive implementation. In FIG. 7, the screen includes multiple panels showing how a project dataset of 8000 documents has been imported to Alpine and preliminarily processed; for example, one panel illustrates various entity types present in the documents identified by extractors ("Extracted Concepts" 602A), another panel illustrates categories of any structured data that is present in the documents ("Document Metadata" 604A), and another panel illustrates other entity types present in the documents that were identified by previously-trained NLP models from prior annotation projects ("Customer Models" 606A). As shown in FIG. 7, in the context of a project dataset in the health care domain used for purposes of illustration, examples of extracted concepts 602A include, but are not limited to, Drugs 602*a*A, Diseases 602*b*A, Body Parts 602*c*A, and Procedures 602*d*A. Examples of document metadata obtained from structured fields of documents of the project dataset include BMI 604*a*A, Weight 604*b*A, Gender 604*c*A, Ethnicity 604*d*A.

Figure 8:
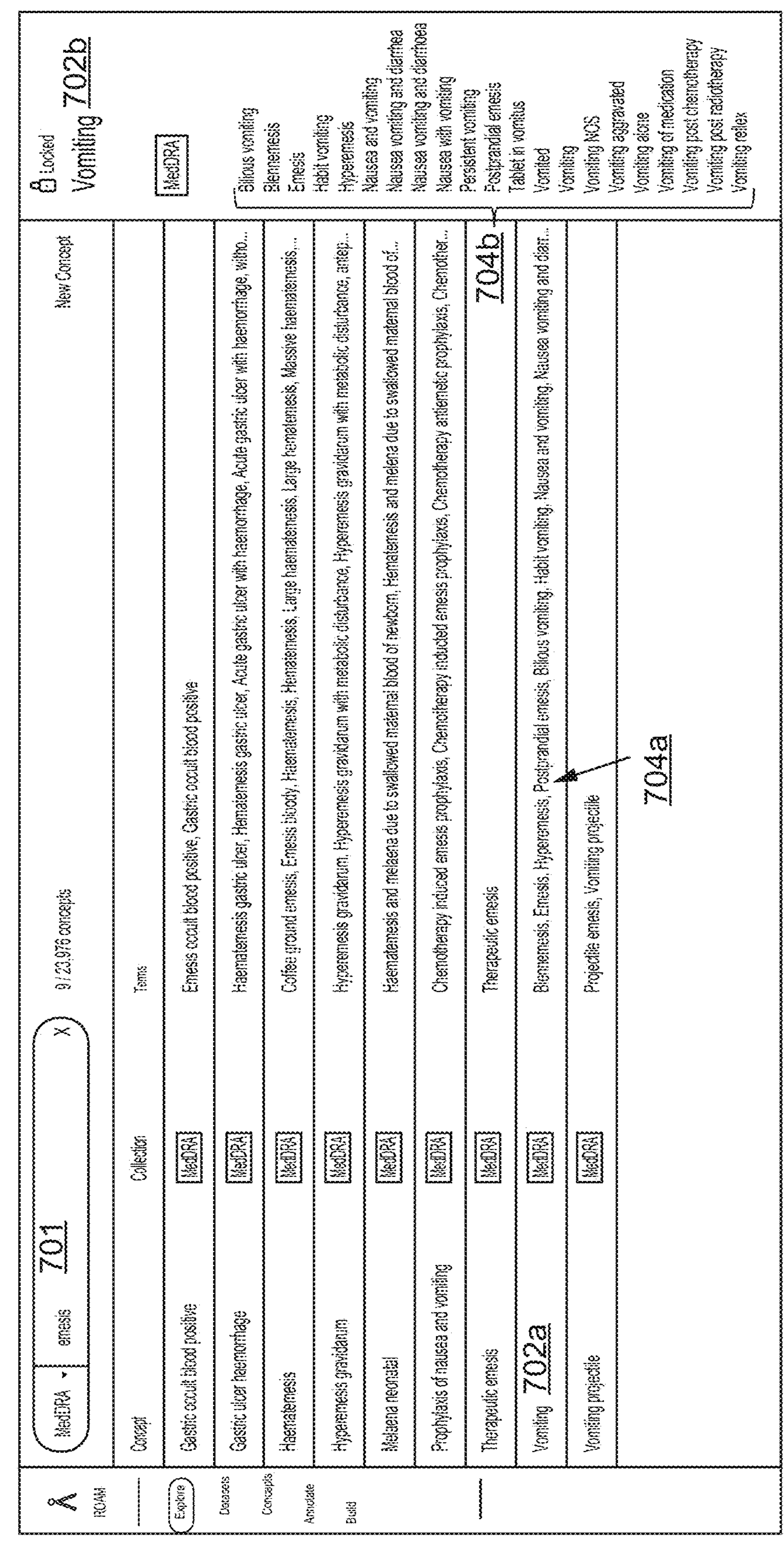
FIG. 8 illustrates a fifth screen shot of the Alpine AUI illustrating concept-based searching of documents within a project dataset based on one or more lexicons, according to one inventive implementation.

FIG. 8 illustrates a fifth screen shot 700 of the Alpine AUI showing how different variations and/or synonyms of the same term can be identified to enable sorting and filtering documents within a project dataset. In FIG. 8, a user can input a term (e.g., "emesis" 701) in the AUI. The display shows one or more concepts that can be identified by one or more lexicons and/or extractors used to process the documents of the project dataset. For instance, FIG. 8 illustrates a concept "vomiting" 702*a* identified by a lexicon or an extractor (not shown in the FIG. 8) that can map different variations 704*a* of the term "vomiting" 702*a* to the same code. As shown in FIG. 8, some of these variations include "bilous vomiting," "nausea and vomiting," "habit vomiting," "emesis," etc. that are displayed as 704*a* and 704*b*. Therefore, a reference to "emesis" 701 in a search query can access a lexicon or an extractor that identifies the concept "vomiting" 702*a* and its variations 704*a* in various documents of the project dataset.

Figure 9:
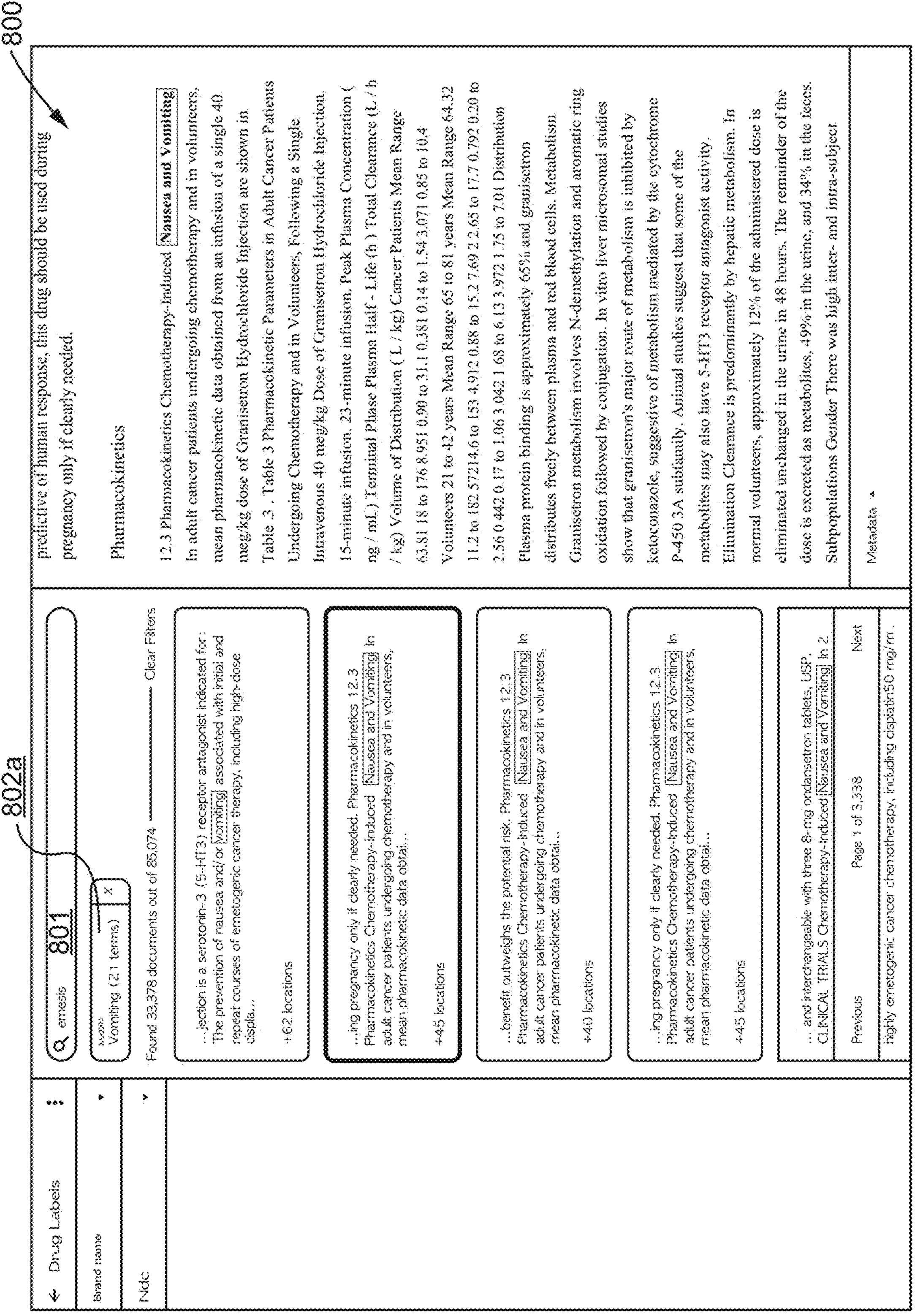
FIG. 9 illustrates a sixth screen shot of the Alpine AUI relating to concept-based searching of documents within a project dataset, according to one inventive implementation.

For instance, FIG. 9 illustrates a sixth screen shot 800 of the Alpine AUI searching for the term "emesis" 801 and its variations in documents of the project dataset. As seen in FIG. 9, "emesis" 801 is a variation of "vomiting," and "vomiting" is mapped to 21 different variations. Therefore, the AUI can determine the number of occurrences of any variation to "emesis" 801 and the number of documents in the project dataset in which the variation occurs. In FIG. 9, "emesis" 801 and its variations occur in 33,378 documents out of 85,074 documents. These 33,378 documents can be filtered out of the 85,074 documents if need be.

"Annotate" Functionality

The "annotate" functionality can enable annotators to develop an annotation scheme and annotation guidelines as well as manually annotate documents in a project dataset.

Designing Annotation Scheme and Guidelines

Figure 10:
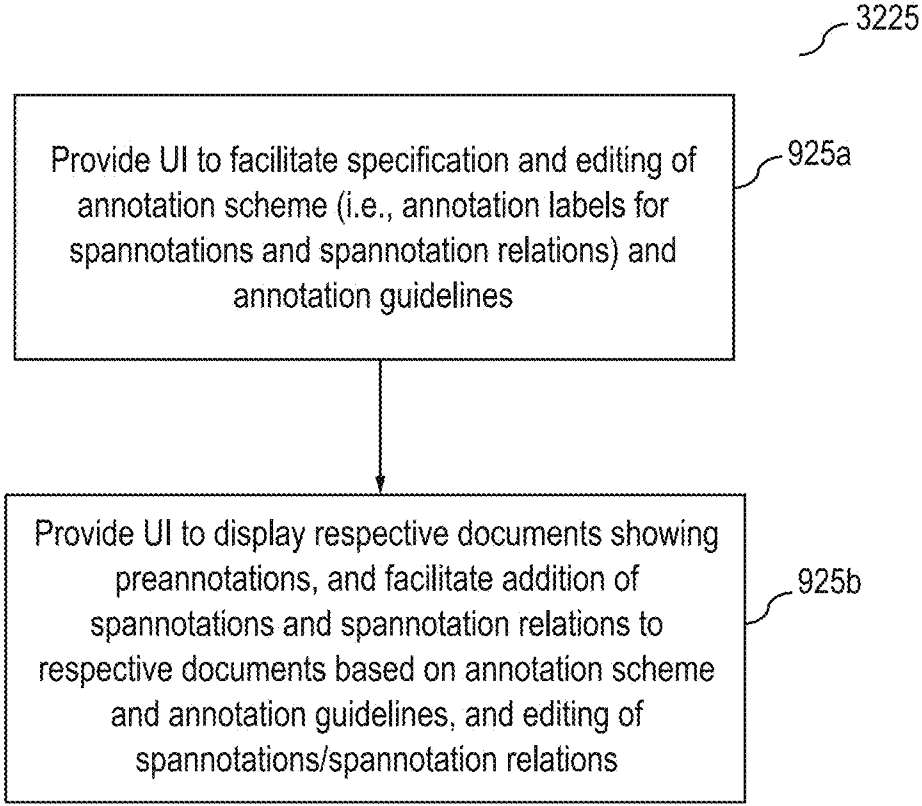
FIG. 10 illustrates further details relating to formulation of an annotation scheme, annotation guidelines, and facilitating annotations in the method outlined in FIGS. 2A and 2B, according to one inventive implementation.

FIG. 10 illustrates a method 3225 with further details relating to formulation of an annotation scheme, annotation guidelines, and facilitating annotation in the method outlined in FIGS. 2A and 2B (e.g., using "Annotate" functionality 104 in FIG. 1) in accordance with one inventive implementation. At 925*a*, the Alpine AUI can provide a graphical user interface to facilitate specification and editing of annotation schemes. These annotation schemes can include annotation labels for spannotations and spannotation relations (refer to Glossary). The Alpine AUI can also facilitate design and specification of annotation guidelines that the annotators can follow to manually annotate documents in the project dataset.

At 925*b*, the Alpine AUI can provide a graphical user interface to display the respective documents that, in some instances, may also show preannotations from the "Explore" functionality. Additionally, it can facilitate addition of spannotations and spannotation relations to respective documents based on the annotation scheme and guidelines. Put differently, one or more annotators can manually add spannotations and spannotation relations to respective documents based on annotation scheme and guidelines. Furthermore, it can also enable any further edits to spannotations and spannotation relations.

Figure 11:
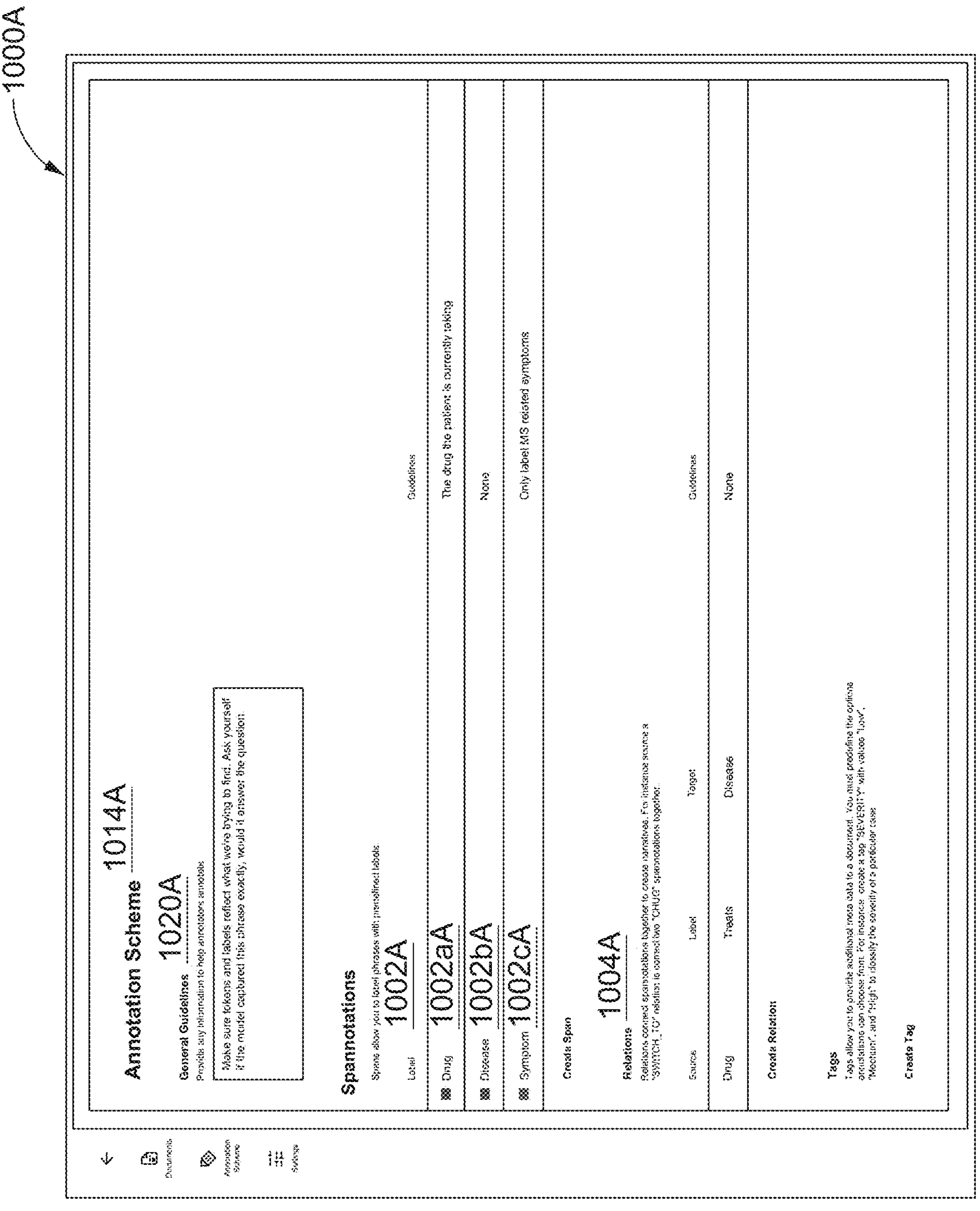
FIG. 11 illustrates a seventh screen shot of the AUI showing various elements of an annotation scheme for an annotation project, according to one inventive implementation.

As shown in step 925*a* in FIG. 10, and with reference to FIG. 11, annotators can initially develop an annotation scheme 1014A for an annotation project. FIG. 11 illustrates a seventh screen shot 1000A of the AUI showing an annotation scheme 1014A and annotation guidelines 1020A developed by annotators for an example project. As illustrated in FIG. 11, the annotation scheme 1014A includes a set of annotation labels 1002A that can be used for spannotations in the annotation project. For the purposes of illustration, the example annotation labels 1002A in FIG. 11 include drug 1002*a*A (for illustrative purposes as an example, a box on the left side of drug 1002*a*A is filled with green color indicating that spannotations of the type "drug" in the documents will display in green color), disease 1002*b*A (for illustrative purposes as an example, a box on the left side of disease 1002*b*A is filled with blue color indicating that spannotations of the type "disease" in the documents will display in blue color), and symptom 1002*c*A (for illustrative purposes as an example, the box on the left side of symptom 1002*c*A is filled with pink color indicating that spannotations of the type "symptom" in the documents will display in pink color). As noted above, however, it should be appreciated that the annotation labels for spannotations that are developed and used in Alpine may be different for different examples and may also pertain to a variety of domains. These annotation labels 1002A allow annotators to label spans in the text documents with predefined labels (i.e., provide spannotations and/or multi-spannotations in the text document). The screen in FIG. 11 also includes annotation labels 1004A for spannotation relations. For instance, the screen in FIG. 11 includes the spannotation relation-drug "TREATS" disease. In one aspect of Alpine, annotators may make changes to the annotation labels 1002A as they are developing an annotation scheme for a given project dataset, and any changes in annotation labels may be applied automatically (propagated) to previously-annotated documents in the project dataset. In another aspect, the annotation scheme 1014A can be machine readable (e.g., to serve as the basis of one or more project NLP target models).

The screen shot 1000A in FIG. 11 also includes annotation guidelines 1020A that can include instructions describing how a manual annotator should use a particular annotation scheme to annotate respective documents of a project dataset. Manual annotators can also add notes and examples for specific policies using Alpine if need be. In one aspect, the annotation guidelines 1020A illustrated in FIG. 11 are not part of the annotation scheme itself, and as such these guidelines need not necessarily be machine readable.

Figure 12:
FIG. 12 illustrates an eighth screen shot of the AUI showing a document level view in which annotations may be added to a document, according to one inventive implementation.

FIG. 12 illustrates an eighth screen shot 1100A of the AUI showing a document level view of annotation. A given annotation scheme developed using Alpine on a preliminary subset of documents from a project dataset can be used for annotating additional subsets of documents in the project dataset (e.g., to increase the number of documents used for training a project NLP target model). In this example, consider an annotation scheme that was previously developed using Alpine (similar to the development of annotation scheme 1014A in FIG. 11) that includes annotation labels for spannotations 1102A and spannotation relations 1104A. As noted above, it should be appreciated that different examples of annotation labels for spannotations and spannotation relations are shown in different figures for purposes of illustrating different possible annotation schemes.

As shown in FIG. 12, the eight screen shot 1100A of the AUI can be include two regions. A first region can display at least a portion of the document 1128 that is being annotated. In this example, the document 1128 appears on the right side of the display. A second region can display the annotation scheme 1120A for annotation. In this example, the annotation scheme 1120A is on the left side of the display.

The annotation scheme 1120A includes annotation labels 1102A for spannotations (under the heading "Spans" on the left side of FIG. 12) and annotation labels 1104A for spannotation relations (under the heading "Relations" on the left side of FIG. 12). In this example, the annotation labels 1102A for spannotations include "Drug" 1102*a*A (for illustrative purposes as an example, the box on the left to "Drug" 1102*a*A is filled with green color indicating that spannotations that are labelled "Drug" 1102*a*A will be highlighted in green color), "Subject" 1102*b*A (for illustrative purposes as an example, the box on the left to "Subject" 1102*b*A is filled with yellow color indicating that spannotations that are labelled "Subject" 1102*b*A will be highlighted in yellow color), "Adverse Drug Event" 1102*c*A (for illustrative purposes as an example, the box on the left to "Adverse Drug Event" 1102*c*A is filled with blue color indicating that spannotations that are labelled "Adverse Drug Event" 1102*c*A will be highlighted in blue color), "Drug Effective" 1102*d*A (for illustrative purposes as an example, the box on the left to "Drug Effective" 1102*d*A is filled with pink color indicating that spannotations that are labelled "Drug Effective" 1102*d*A will be highlighted in pink color), "Drug Ineffective" 1102*e*A (for illustrative purposes as an example, the box on the left to "Drug Ineffective" 1102*e*A is filled with orange color indicating that spannotations that are labelled "Drug Ineffective" 1102*e*A will be highlighted in orange color), and "Contributing Factor" 1102*f*A (for illustrative purposes as an example, the box on the left to "Contributing Factor" 1102*f*A is filled with purple color indicating that spannotations that are labelled "Contributing Factor" 1102*f*A will be highlighted in purple color).

The annotation scheme 1104A for spannotation relations include "has_ADE:Drug→Adverse Drug Event" 1104*a*A (in this example, the box to the left of the spannotation relation "has_ADE: Drug→Adverse Drug Event" 1104*a*A is filled with two colors—the left part of the box is filled with green color and right part of the box is filled with blue color. This indicates that the spannotation relation 1104*a*A indicates the relationship between spannotation "Drug" 1102*a*A and "Adverse Drug Event" 1102*c*A), "has_contributing_factor: Adverse Drug" 1104*b*A (in this example, the box to the left of the spannotation relation "has_contributing_factor: Adverse Drug" 1104*b*A is filled with two colors—the left part of the box is filled with blue color and right part of the box is filled with purple color. This indicates that the spannotation relation 1104*b*A indicates the relationship between spannotation "Adverse Drug Event" 1102*c*A and "Contributing Factor" 1102*f*A), "is_effective: Drug→Drug Effective" 1104*c*A (in this example, the box to the left of the spannotation relation "is_effective: Drug→Drug Effective" 1104*c*A is filled with two colors—the left part of the box is filled with green color and right part of the box is filled with pink color. This indicates that the spannotation relation 1104*c*A indicates the relationship between spannotation "Drug" 1102*a*A and "Drug Effective" 1102*d*A), and "not_effective: Drug→Drug Ineffective" 1104*d*A (in this example, the box to the left of the spannotation relation "not_effective: Drug→Drug Ineffective" 1104*d*A is filled with two colors—the left part of the box is filled with green color and right part of the box is filled with orange color. This indicates that the spannotation relation 1104*d*A indicates the relationship between spannotation "Drug" 1102*a*A and "Drug Ineffective" 1102*e*A).

An annotator may annotate the document by selecting one of the annotation labels 1102A or 1104A on the left side of the display. Following the selection of an appropriate annotation label, an annotator can place the annotation label 1102A or 1104A adjacent to a span of text in the displayed portion of the document 1128. In this example, the annotator selects the annotation label "Drug" 1102*a*A for spans "calcium folinate" 1110A, "vitamin B12" 1110B, "vitamin B6" 1110C, and "betaine" 1110D. As a result, spans "calcium folinate" 1110A, "vitamin B12" 1110B, "vitamin B6" 1110C, and "betaine" 1110D in the document 1128 are highlighted in green, and the annotation label "Drug" is placed adjacent to (e.g., immediately above) each of the highlighted spans. The annotator selects the annotation label "Drug Effective" 1102*d*A for span "After the treatment for 1 week, his plasma and urine levels of homocysteine were decreased to a normal range and the clinical symptoms were significantly improved" 1112A. As a result, span 1112A is highlighted in pink, and the annotation label "Drug Effective" is placed adjacent to (immediately above) the highlighted span. The annotator may then add spannotation relation "is_effective: Drug→Drug Effective" 1104*c*A to indicate the relationship between the respective spannotations. In this case, the spannotation relation 1114*a* indicates the relationship between spans 1110A and 1112A. In a similar manner, spannotation relation 1114*b* indicates the relationship between spans 1110B and 1112A, spannotation relation 1114*c* indicates the relationship between spans 1110C and 1112A, and spannotation relation 1114*d* indicates the relationship between spans 1110D and 1112A.

Thus, FIG. 11 and FIG. 12 together illustrate an instantiation of a method for displaying, and facilitating annotation of, one or more documents to be annotated as part of a collaborative annotation project. In FIG. 11, a first graphical user interface is generated that facilitates definition, modification, and display of an annotation scheme for the annotation project, in which the annotation scheme comprises a set of annotation labels. In FIG. 12, a second graphical user interface is generated that 1) displays at least a portion of a first document in a first region of the second graphical user interface (e.g., center-right portion of the GUI); 2) displays the set of annotation labels of the annotation scheme in a second region of the second graphical user interface (e.g., left portion of the GUI); and 3) facilitates annotation of the portion of the first document displayed in the first region of the second graphical user interface. This annotation is facilitated via selection of a first annotation label of the set of annotation labels displayed in the second region of the second graphical user interface and, following selection of the first annotation label, placement of the selected first annotation label adjacent to at least a first span of text in the portion of the first document displayed in the first region of the second graphical user interface.

As discussed above in connection with FIG. 12, the annotation of the first document is further facilitated by the second GUI by providing a first visual identifier for the first span of text in the portion of the first document displayed in the first region of the second graphical user interface so as to form a first spannotation, wherein the first spannotation comprises the first visual identifier and the selected first annotation label adjacent to the first span of text. The first span of text mentions a first entity having a first entity type (e.g., "Drug"), and the selected first annotation label includes a first text string ("Drug") that identifies the first entity type for the first entity mentioned in the first span of text. In the example of FIG. 12, the selected first annotation label includes a first label attribute (e.g., green color), and the first visual identifier for the first span of text and the first label attribute of the selected first annotation label are selected to visually indicate a correspondence between the first span of text (e.g., green highlighting) and the selected first annotation label (e.g., green color for the label text).

Regarding a visual correspondence between the annotation label and the span of text being labeled, FIG. 12 generally illustrates that the first visual identifier for the first span of text includes highlighting the first span of text with a first span highlighting color, and the first label attribute includes a first label color for the first text string of the selected first annotation label, wherein the first span highlighting color and the first label color are the same or have a same hue. More generally, various examples of visual identifiers for spans of text include, but are not limited to, highlighting the span of text with span shading and/or a particular span highlighting color; a particular span text color for at least one character in the span of text; or a particular span font style of at least one character in the first span of text. Similarly, various examples of label attributes for a given annotation label include, but are not limited to, highlighting for the text string of the annotation label with label shading and/or a particular label highlighting color; a particular label color for the first text string of the selected first annotation label; or a particular label font style for the first text string of the selected first annotation label.

Figure 13:
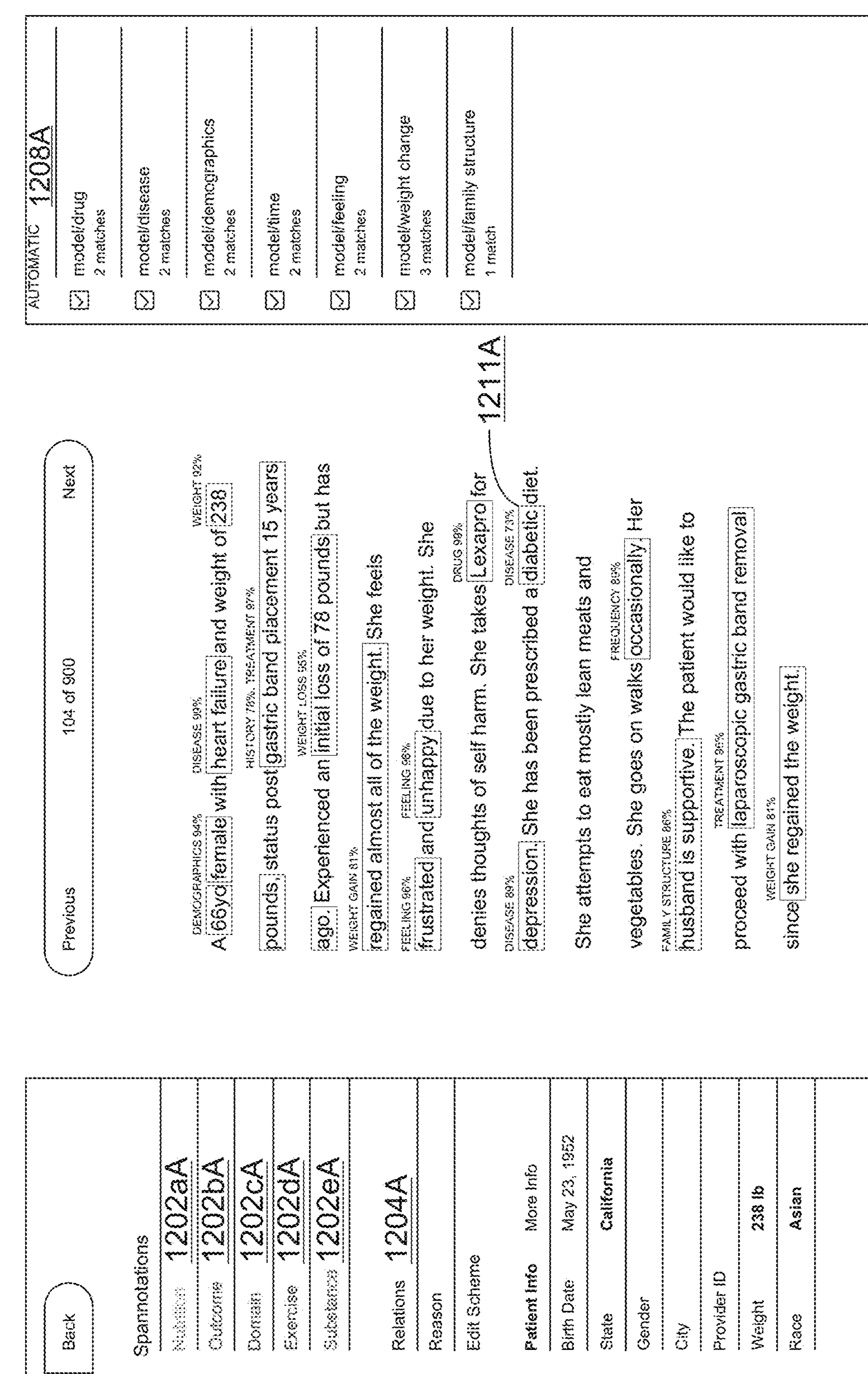
FIG. 13 illustrates a ninth screen shot of the AUI showing another document level view in which preannotations are illustrated in a document, according to one inventive implementation.

FIG. 13 illustrates a ninth screen shot 1200A of the AUI showing another document level view of annotation. The annotation scheme developed using Alpine is shown on the left side of the screen shot. In this example, the annotation scheme includes annotation labels "Nutrition" 1202*a*A (for illustrative purposes as an example, the text "Nutrition" 1202*a*A is in orange color indicating that spannotations that are labelled "Nutrition" 1202*a*A will be highlighted in orange color), "Outcome" 1202*b*A (for illustrative purposes as an example, the text "Outcome" 1202*b*A is in dark blue color indicating that spannotations that are labelled "Outcome" 1202*b*A will be highlighted in dark blue color), "Domain" 1202*c*A (for illustrative purposes as an example, the text "Domain" 1202*c*A is in green color indicating that spannotations that are labelled "Domain" 1202*c*A will be highlighted in green color), "Exercise" 1202*d*A (for illustrative purposes as an example, the text "Exercise" 1202*d*A is in violet color indicating that spannotations that are labelled "Exercise" 1202*d*A will be highlighted in violet color), and "Substance" 1202*e*A (for illustrative purposes as an example, the text "Substance" 1202*e*A is in pink color indicating that spannotations that are labelled "Substance" 1202*e*A will be highlighted in pink color) for spannotations. The annotation scheme also includes spannotation relation 1204A. The right side of the screen shot 1200A shows extractors 1208A that when executed automatically preannotate the text. In some implementations, these extractors correspond to a canonical node type in the RKG. For example, the extractors "model/drug" and "model/disease" may correspond to canonical node types "roam/Drug" and "roam/disease" in the RKG. In other implementations, it should be appreciated that one or more of the extractors 1208A may not correspond to a canonical node type in the RKG.

As illustrated in FIG. 13, multiple entity types (concepts) may be preannotated (e.g., highlighted text in FIG. 13, for illustrative purposes as an example, the highlighted text is highlighted in grey color indicating that the spannotations that are preannotated by extractors are highlighted in grey color) as a result of the extractors 1208A. Each preannotation has a probability value associated with it. The probability value represents the probability that an extractor 1208A generates regarding the statistical correctness of each of its predictions.

In some inventive aspects, annotators can change and/or delete spannotation labels and spannotation relations, annotate new spans using existing annotation scheme, and/or alter/augment the annotation scheme in real time with new spannotation labels and spannotation relations. In any and all of these cases, Alpine automatically updates the annotation scheme.

Figure 14:
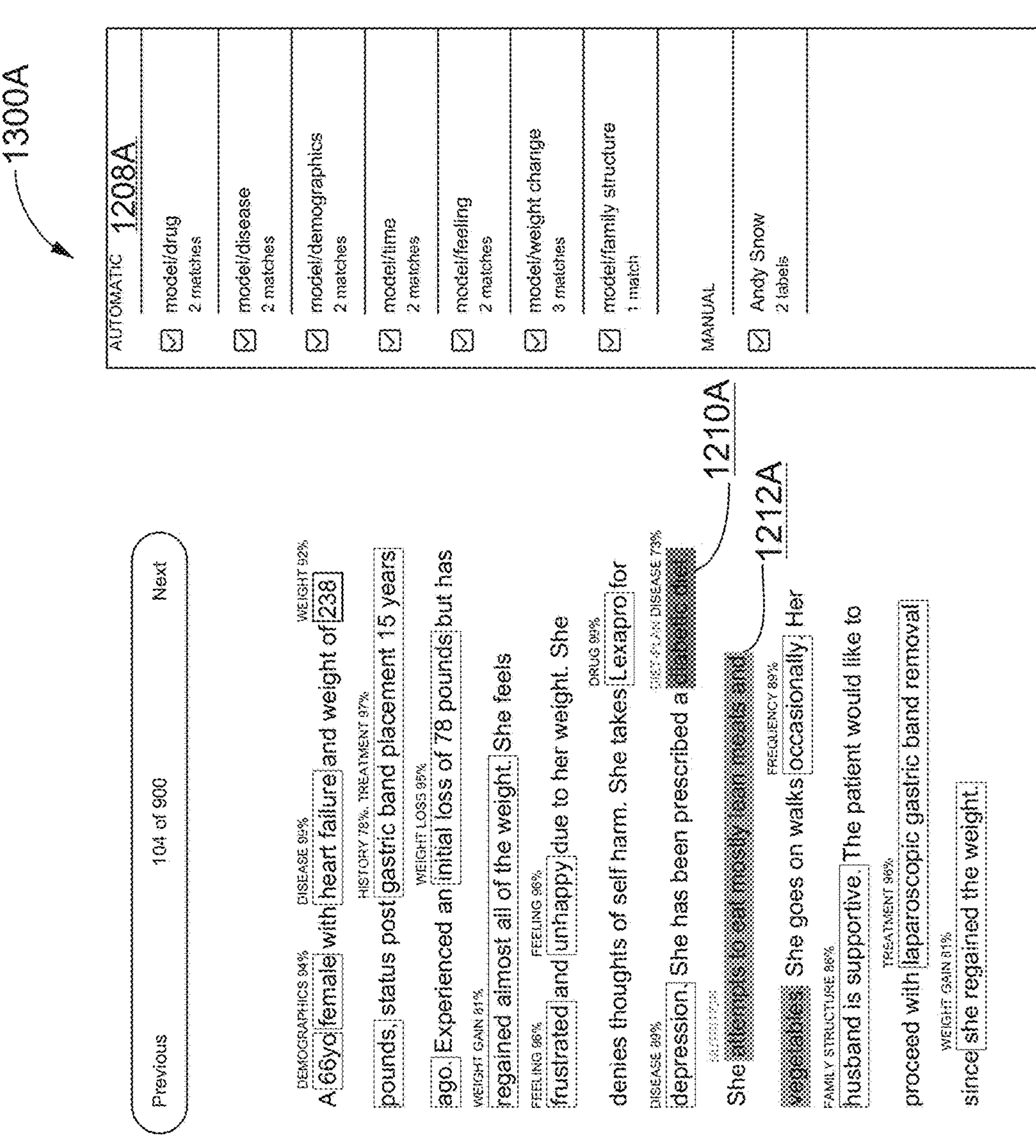
FIG. 14 illustrates a tenth screen shot of the AUI showing an example of spannotations that have been added to the document shown in FIG. 13, according to one inventive implementation.

FIG. 14 illustrates a tenth screen shot 1300A of the AUI showing manual annotation of the document. In this example, an annotator manually annotates the highlighted text 1212A "attempts to eat mostly lean meats and vegetables" (for illustrative purposes as an example, the highlighted text 1212A is highlighted in orange color) with the annotation label "Nutrition" 1202*a*A. In FIG. 13, the span "diabetic" (highlighted text 1211A, for illustrative purposes as an example, the highlighted text 1211A is highlighted in grey color) was preannotated as "Disease" as a result of the extractor "model/disease." However, a manual annotator may realize that this annotation does not capture information in the text in a manner that is valuable to the project. The manual annotator can therefore change or correct the annotation label for a spannotation. In this example, the manual annotator adds a new annotation label "Diet Plan" 1202*f*A (for illustrative purposes as an example, the text "Diet Plan" 1202*f*A is in light blue color indicating that spannotations that are labelled "Diet Plan" 1202*f*A will be in highlighted light blue color) and changes the annotation label for the span "diabetic diet" to "Diet Plan" 1202*f*A (for illustrative purposes as an example, the highlighted text "diabetic diet" 1210A is highlighted in light blue color). Therefore, the annotation scheme is expanded to include the annotation label "Diet Plan" 1202*f*A. As shown in FIG. 15, an annotator can add an annotation label 1214A to capture the relationship between two spannotations (1210A and 1212A).

Setting Missions and Resolving Conflicts

In some inventive aspects, after developing an annotation scheme based on preliminary manual annotation subsequent to preannotation, one or more annotators can be assigned to another subset of sample documents of the project dataset to further annotate the sample documents according to the annotation scheme.

Figure 16:
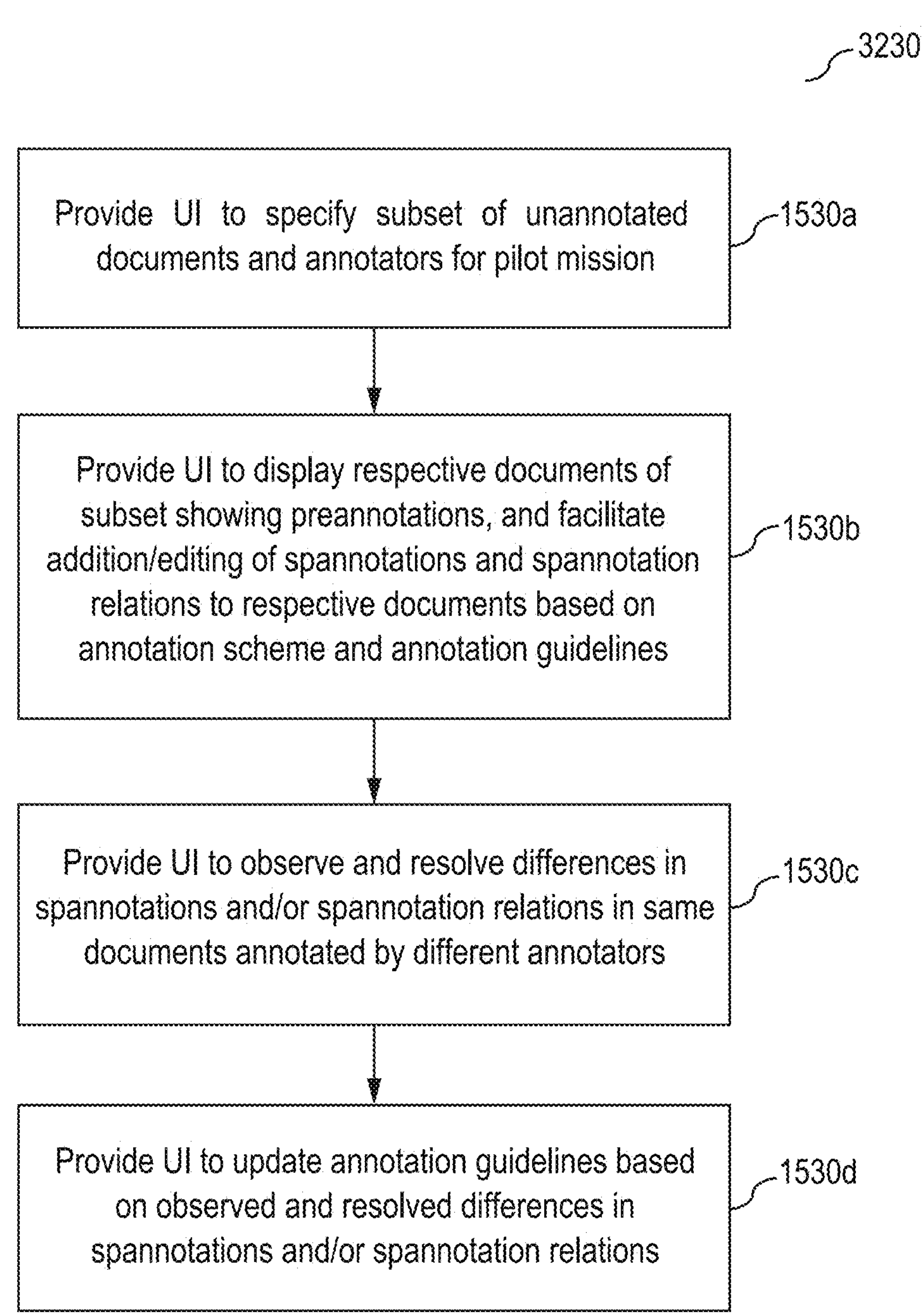
FIG. 16 illustrates further details relating to conducting a pilot mission for annotating documents in the method outlined in FIGS. 2A and 2B, according to one inventive implementation.

FIG. 16 illustrates a method 3230 with further details relating to conducting a pilot mission for annotating documents in the method outlined in FIGS. 2A and 2B (e.g., using "Annotate" functionality 104 in FIG. 1), according to one inventive implementation. At 1530*a*, the Alpine AUI can present a graphical user interface that can enable a user to specify a subset of unannotated documents for annotation and assign annotators who can manually annotate the documents. At 1530*b*, the respective subset of unannotated documents showing preannotations can be displayed. The assigned annotators can add and/or edit spannotations and spannotation relations based on annotation scheme and annotation guidelines.

At 1530*c*, the graphical user interface can display disagreement and/or conflicts between different annotators on the spannotations and/or the spannotation relations to the same document. These differences can be resolved by the Alpine AUI. At 1530*d*, the annotation scheme and guidelines can be updated based on the observed and resolved differences in spannotation and/or spannotation relations.

In some inventive aspects, Alpine can enable setting up one or more missions to assign annotators to annotate sample documents. FIG. 17 illustrates a twelfth screen shot of the AUI showing an example mission to assign annotators to text documents. In some inventive aspects, a mission can identify a subset of text documents to annotate according to the annotation scheme. In some inventive aspects, a mission can organize the work of expert annotators in a way that is most useful to the use case goal of the annotation project. In FIG. 17, an initial mission such as "pilot annotation" can be set up to assign sample documents to be annotated by an elite team of annotators. Best annotators/elite group of annotators are often trained to identify overlooked concepts and make changes to the annotation scheme. In this example, a small document sample set (e.g., 20 documents) is assigned to each annotator participating in the mission (for e.g., see FIG. 17). Thus, each document is annotated by multiple annotators.

Alpine also allows users to review disagreements between annotators and resolve disagreements between annotators. In this manner, Alpine enables improvement of annotation scheme and annotation guidelines.

Figure 18:
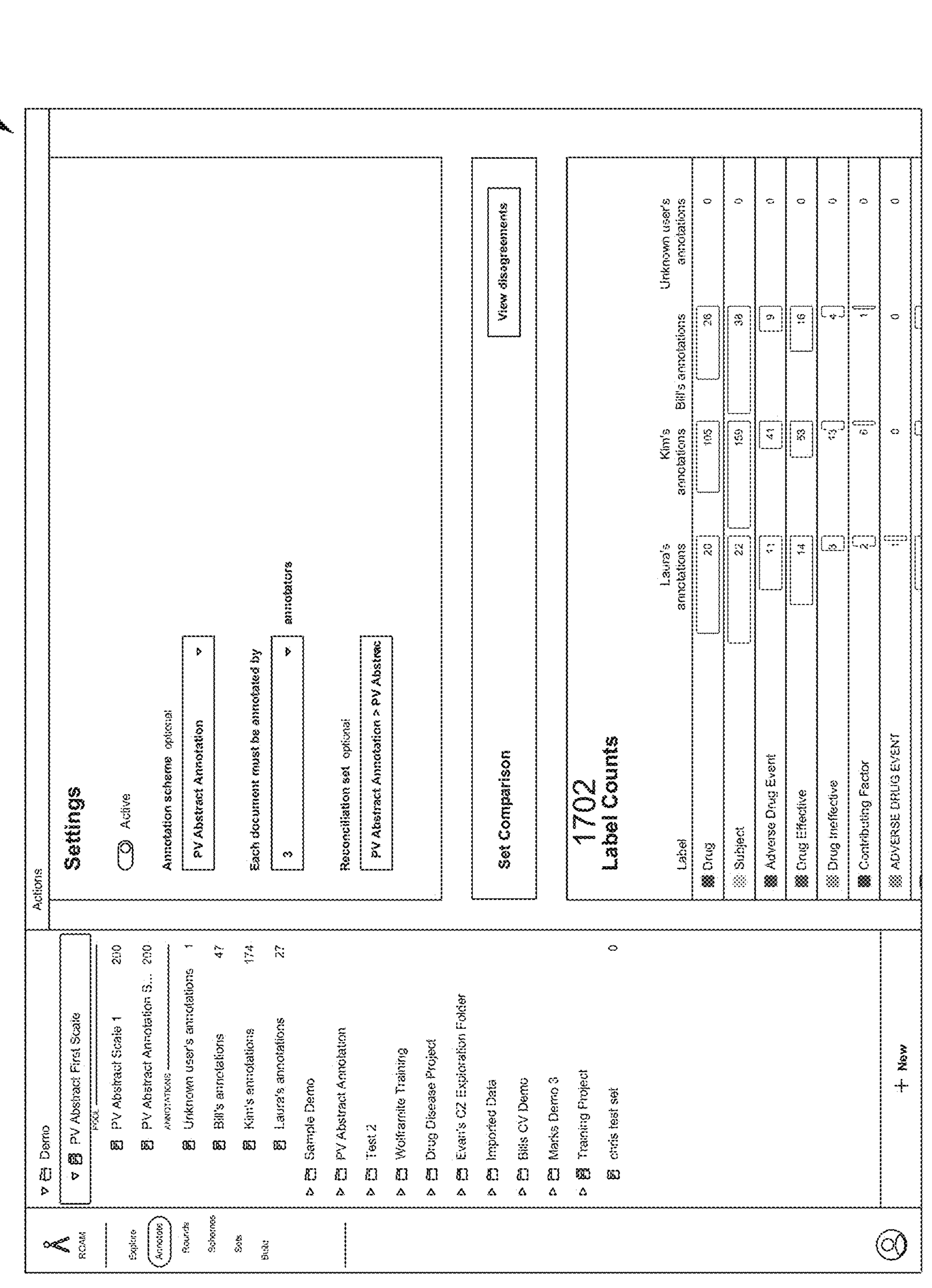
FIG. 18 illustrates a thirteenth screen shot of the AUI showing an option to review disagreements between annotators on spannotations and spannotation relations during the mission, according to one inventive implementation.

In some inventive aspects, once the annotators annotate a set of documents, Alpine allows users to review disagreements between the annotators on annotation labels for spannotations and spannotation relations (for e.g., see FIG. 18). In conventional methods, separate tools are employed to resolve disagreements between annotators. For instance, ad hoc interfaces are used to resolve disagreements, or data scientists and engineers are employed to do so (in some instances manually). This can lead to poor choices such as, taking the majority label, or deferring to the most senior annotator.

In contrast, Alpine has in-built tools to review and resolve disagreements between the annotators on annotation labels for spannotations and spannotation relations. As seen in FIG. 18, the label counts 1702 display the number of times each annotator has used each of the annotation labels in order to annotate the documents in the project dataset. In this example, the display shows the number of times each of the annotators, "Laura," "Kim," and "Bill" have used each of the annotation labels "Drug," "Subject," "Adverse Drug Event," "Drug Effective," "Drug Ineffective," and "Contributing Factor" to annotate the documents in the project dataset.

Figure 19:
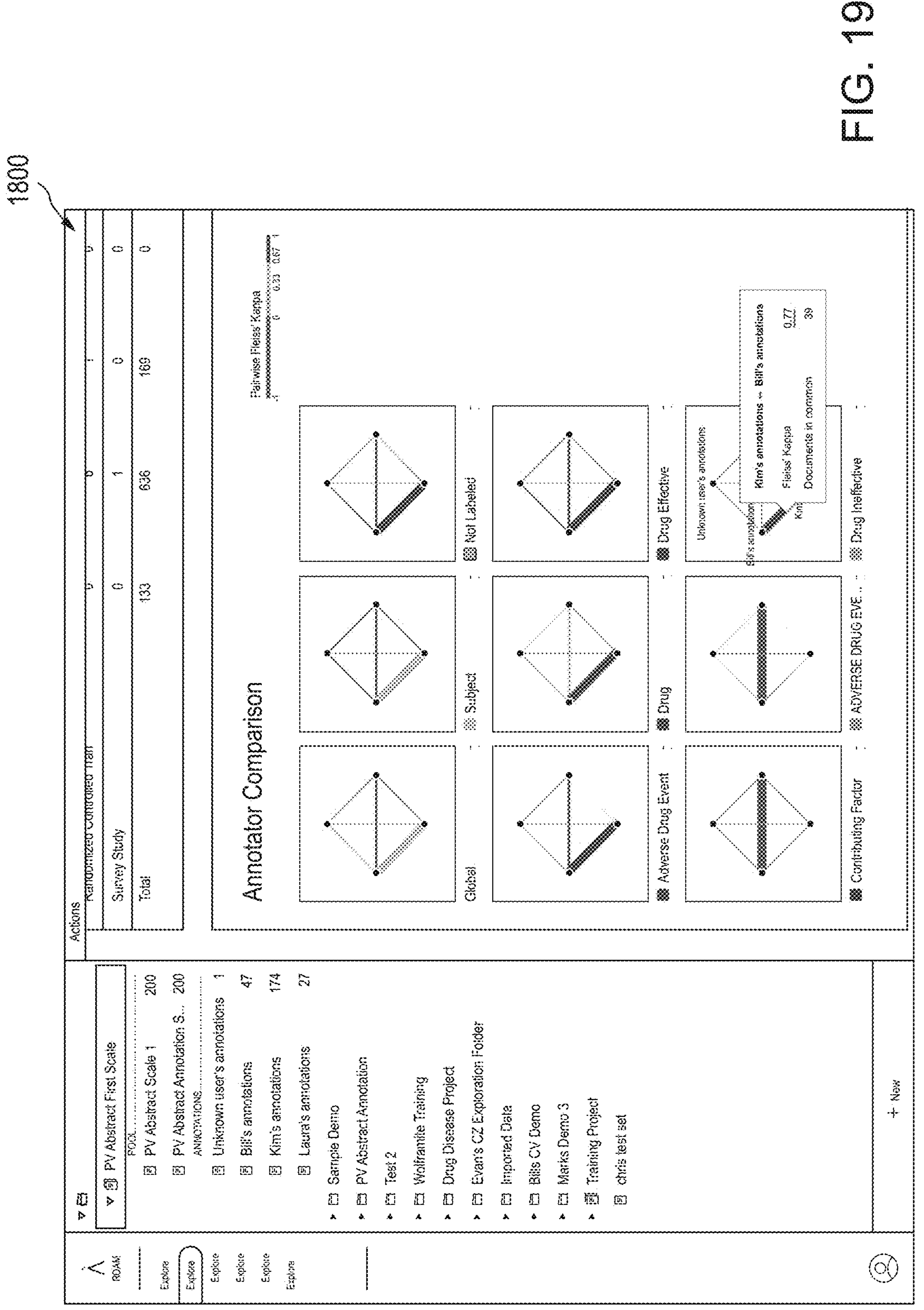
FIG. 19 is a fourteenth screen shot of the AUI showing a comparison of annotation by different reviewers, according to one inventive implementation.

Alpine AUI can provide a visual comparison of disagreements between the reviewers. FIG. 19 is a fourteenth screen shot 1800 of the AUI showing a comparison of annotation by different reviewers. For each annotation label, a Fleiss Kappa score can be displayed to show the reliability of agreement between two annotators. A Fleiss Kappa score is a statistical measure for assessing the reliability of agreement between the annotators when they annotate the documents based on the existing annotation scheme and guidelines. As seen in the example illustrated in FIG. 19, the Fleiss Kappa score for the annotation label "Drug Ineffective" between annotators "Kim" and "Bill" is 0.77.

Figure 20:
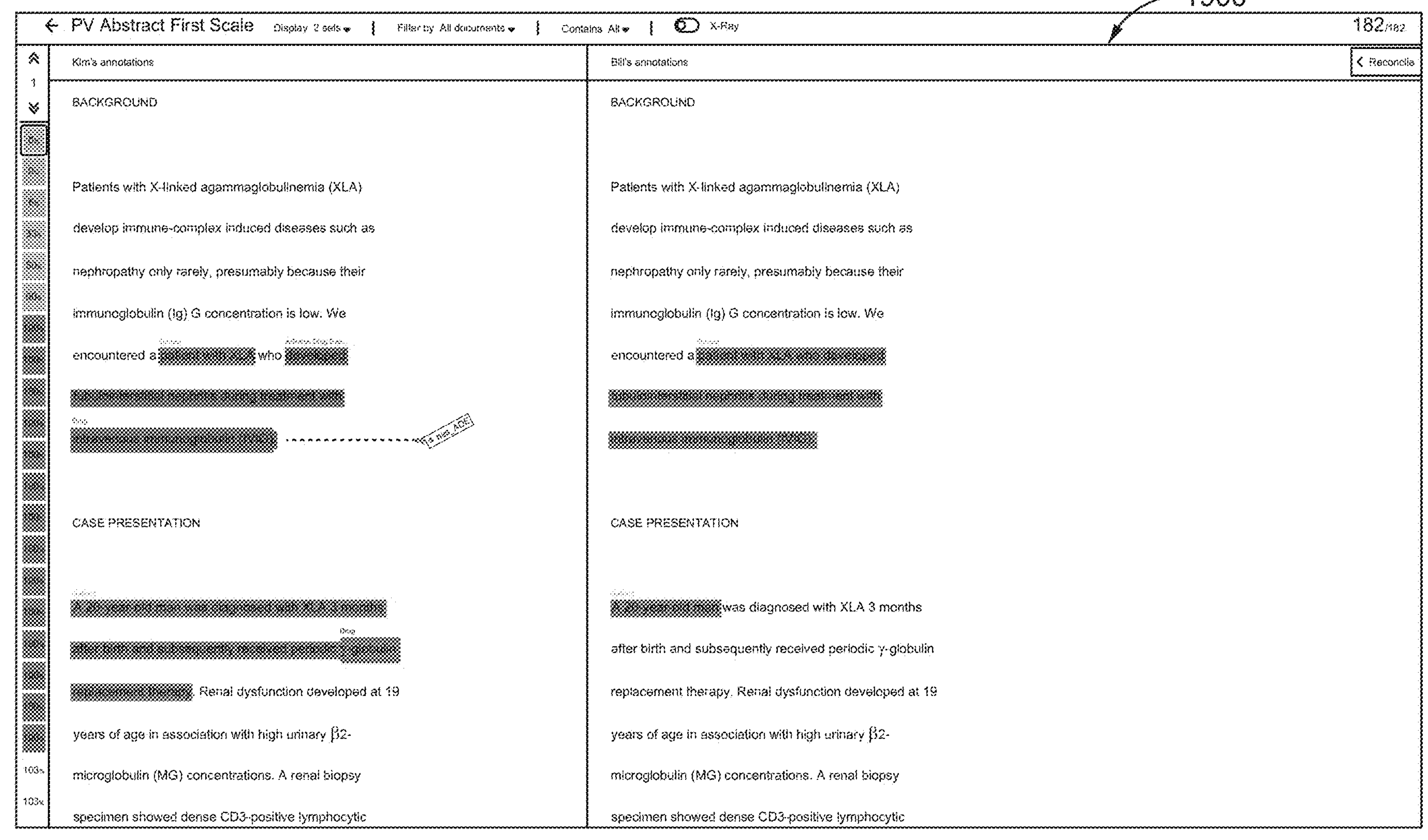
FIG. 20 is a fifteenth screen shot of the AUI when there is poor agreement between two annotators, according to one inventive implementation.

A display of each annotated document by two different annotators shows the disagreements between the annotators. FIG. 20 is a fifteenth screen shot 1900 of the AUI when there is poor agreement between two annotators. In the example shown in FIG. 20, a sample document annotated by two annotators "Kim" (annotated sample document on the left side of the screen shot) and "Bill" (annotated sample document on the right side of the screen shot) have no agreement. Put differently, the annotation labels assigned by "Kim" is completely different from the annotation labels assigned by "Bill" for the same sample document.

Figure 21:
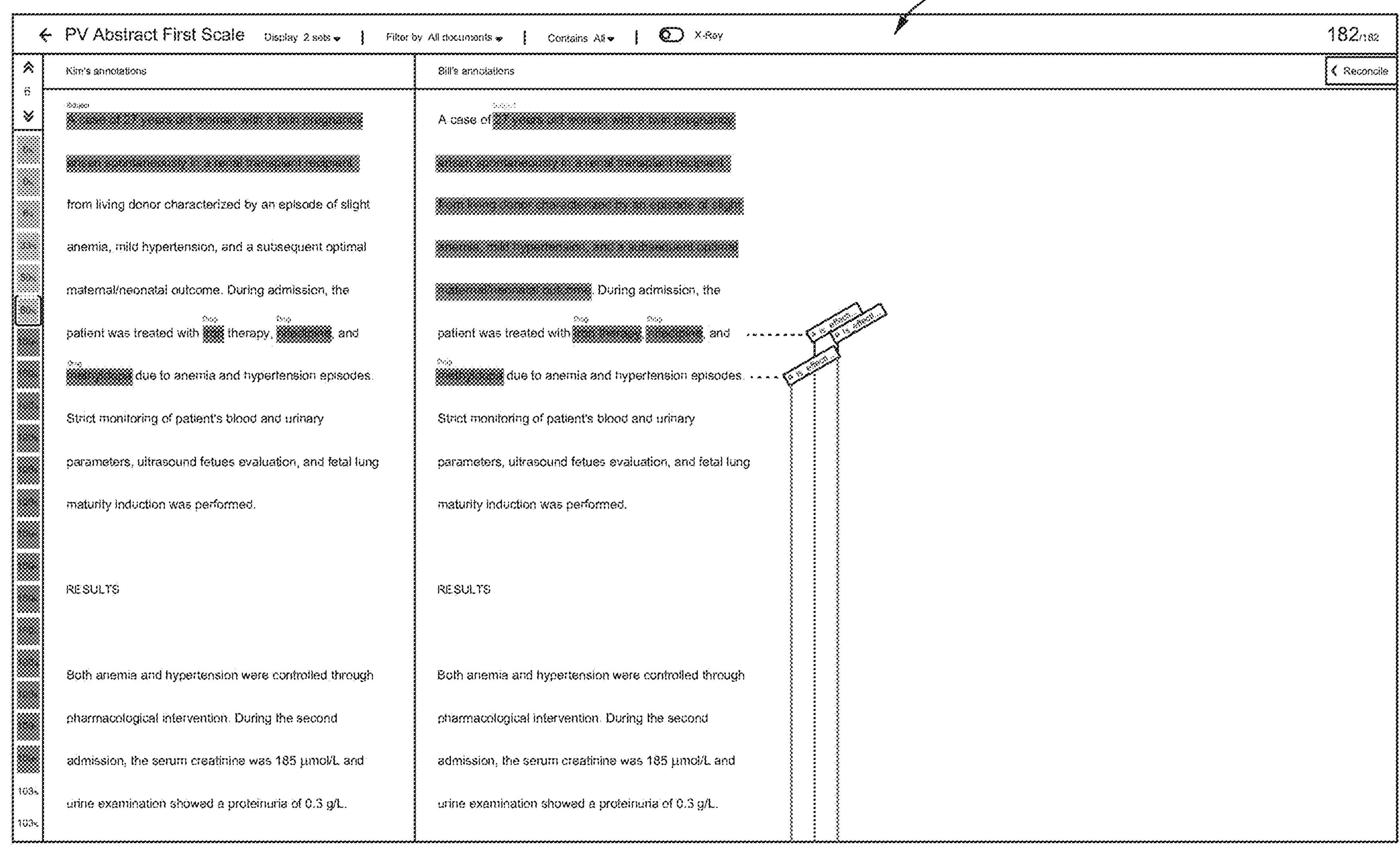
FIG. 21 is a sixteenth screen shot of the AUI when there is moderate agreement between two annotators, according to one inventive implementation.

FIG. 21 is a sixteenth screen shot 2000 of the AUI when there is moderate agreement between two annotators. In this example, a sample document annotated by "Kim" (annotated sample document on the left side of the screen shot) and "Bill" (annotated sample document on the right side of the screen shot) have about 60 percent agreement.

Figure 22:
FIG. 22 is a seventeenth screen shot of the AUI when there is perfect agreement between two annotators, according to one inventive implementation.

FIG. 22 is a seventeenth screen shot 2100 of the AUI when there is perfect agreement between two annotators. In this example, a sample document annotated by "Kim" (annotated sample document on the left side of the screen shot) and "Bill" (annotated sample document on the right side of the screen shot) are in perfect agreement.

Figure 23:
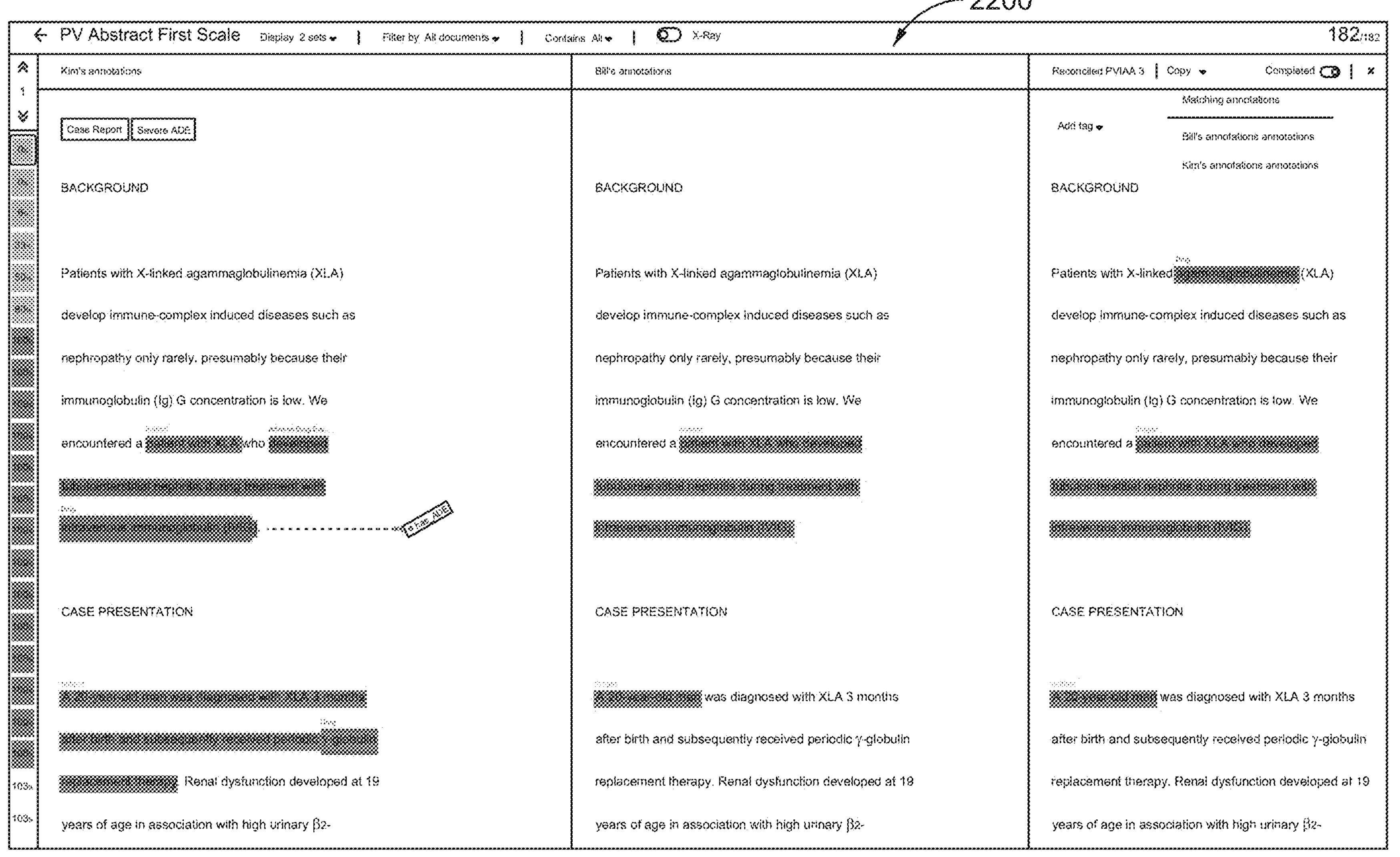
FIG. 23 illustrates a eighteenth screen shot of the AUI showing an example for resolving differences between the annotations by different annotators, according to one inventive implementation.

FIG. 23 illustrates an example of resolving this conflict using the Alpine AUI. As can be readily seen in FIG. 23, Alpine can easily observe and reconcile/resolve differences between different annotators. In this example, a sample document annotated by "Kim" (annotated sample document on the left side of the screenshot) and "Bill" (annotated sample document in the center of the screen shot) can be analyzed and their conflicts resolved. In FIG. 23, a user can review and analyze both the annotated documents, choose the annotation labels that the user finds a better fit for the project dataset, and add annotation labels that both the annotators may have missed out.

In some inventive aspects, for a given sample document that is reviewed by multiple annotators, Alpine allows selection of one annotator's annotation over the other annotator. Alternatively, Alpine allows a user to indicate that both the annotator's annotations are incorrect. In addition, Alpine also allows annotators to capture the examples that they have disagreed on and put them into annotation guidelines in order to educate the other annotators.

In this manner, annotators can review and modify preannotated documents (annotated via extractors) to develop an annotation scheme for the project at hand and an initial set of training documents for a project NLP target model. Alpine also enables automatically changing and augmenting the annotation scheme to improve the accuracy and relevancy of annotations.

"Build Functionality"

The "Build" functionality can facilitate designing and/or training of one or more NLP project target models. The design and training of the NLP target models can be done iteratively using active learning framework to achieve high levels of model accuracy.

Active Learning Framework

Manual annotations can be used to train one or more project NLP target models based on the annotation scheme. Iteratively-trained NLP models based on manual annotations can be used to automatically analyze a larger number of documents in the project dataset.

More specifically, human expert annotators may first review and annotate a relatively small subset of documents in the project dataset using Alpine. The annotation scheme that is developed based on these initial annotations can then be used to annotate a larger number of documents, which in turn may be employed to train one or more project NLP target models. Once trained, these project NLP target models can be used to analyze and automatically annotate a larger set of documents in the project dataset. These newly annotated larger set of documents can be further analyzed and can be used to further correct the annotations automatically generated by the NLP target models. In this manner, a given project NLP target model may be improved with multiple training iterations.

In some inventive aspects, a library of project NLP target models may be designed to analyze documents in a particular information domain of interest (e.g., clinical texts relating to healthcare) to extract particular information from these documents and to provide automatic annotations for these documents. This helps facilitate computational analysis on unstructured or free-form text in respective documents of the project dataset.

In some inventive aspects, project NLP target models may be engineered (e.g., based on a particular lexicon or ontology) to identify any one or more of a variety of entities that may be present in the source text documents. Thus, the project NLP target models may identify entities and relationships that are not explicitly codified as nodes and edges in an RKG. In some inventive aspects, these relationships that are not explicitly codified in an RKG can be added to the RKG to improve and enhance the RKG itself.

In some inventive aspects, a project NLP target model can be developed using Alpine in parallel as the annotation project is unfolding. The initial goal while developing the project NLP target model is to use Artificial Intelligence techniques to extract as much information as possible from annotated documents that the annotators have manually annotated. The annotation labels for spannotations and spannotation relations in the project documents reflect latent content such as entities and relationships in the annotation project based on the expertise of the annotators in the field of domain of the annotation project. The goal is for the project NLP target models to acquire this implicit knowledge so that they can apply it at machine scale.

Figure 24:
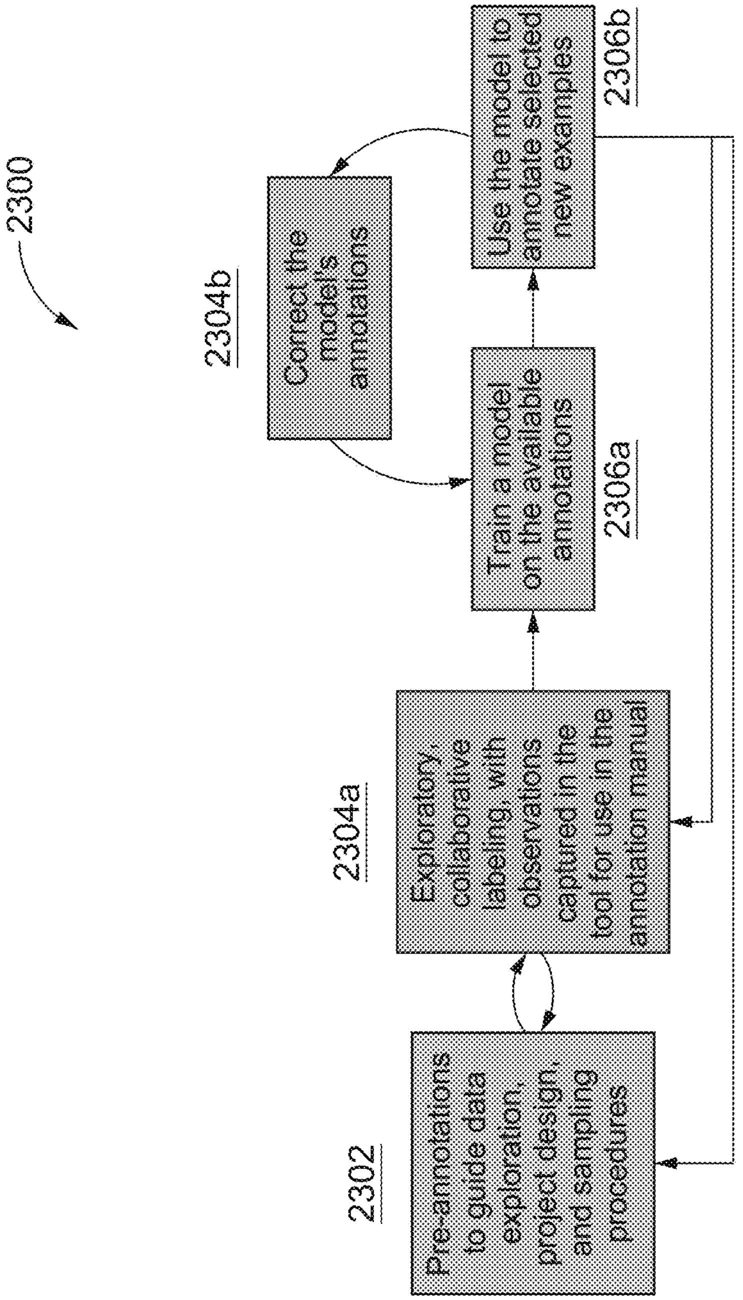
FIG. 24 is a flowchart illustrating an overview of an active learning framework for NLP model training, according to one inventive implementation.

FIG. 24 is a flowchart illustrating an overview of the active learning framework 2300. The active learning framework 2300 can mix annotation that are derived from prebuilt modules such as extractors, NLP models, etc. (at 2302) with free-form collaboration and annotation (i.e., annotation and collaboration between annotators at 2304*a* and 2304*b*), and model development to speed up the annotators and guide the development of the project NLP target models (at 2306*a* and 2306*b*).

Put differently, preannotated documents that were preannotated using the “Explore” functionality (at 2302) can be combined with manual annotations that can be generated using the “Annotate” functionality (at 2304*a*). The preannotated documents which are then manually annotated by annotators can be used as training datasets to design and train project NLP target models (at 2306*a*). The project NLP target models can then be used to automatically annotate other documents in the same project dataset and/or documents in a project dataset that belong to the same domain as the training data (at 2306*b*). These annotations can then be reviewed by annotators, and corrections can be made to the annotation labels and annotation scheme (at 2304*b*). The corrections can be used to re-train the project NLP target models (at 2306*a*). Once the project NLP target models achieve sufficient accuracy these models can be used to preannotate other documents (belonging to the same project dataset and/or same domain as the training dataset) (at 2302). Therefore, the active learning framework supports the non-linear and iterative nature of NLP target model development.

Figure 25:
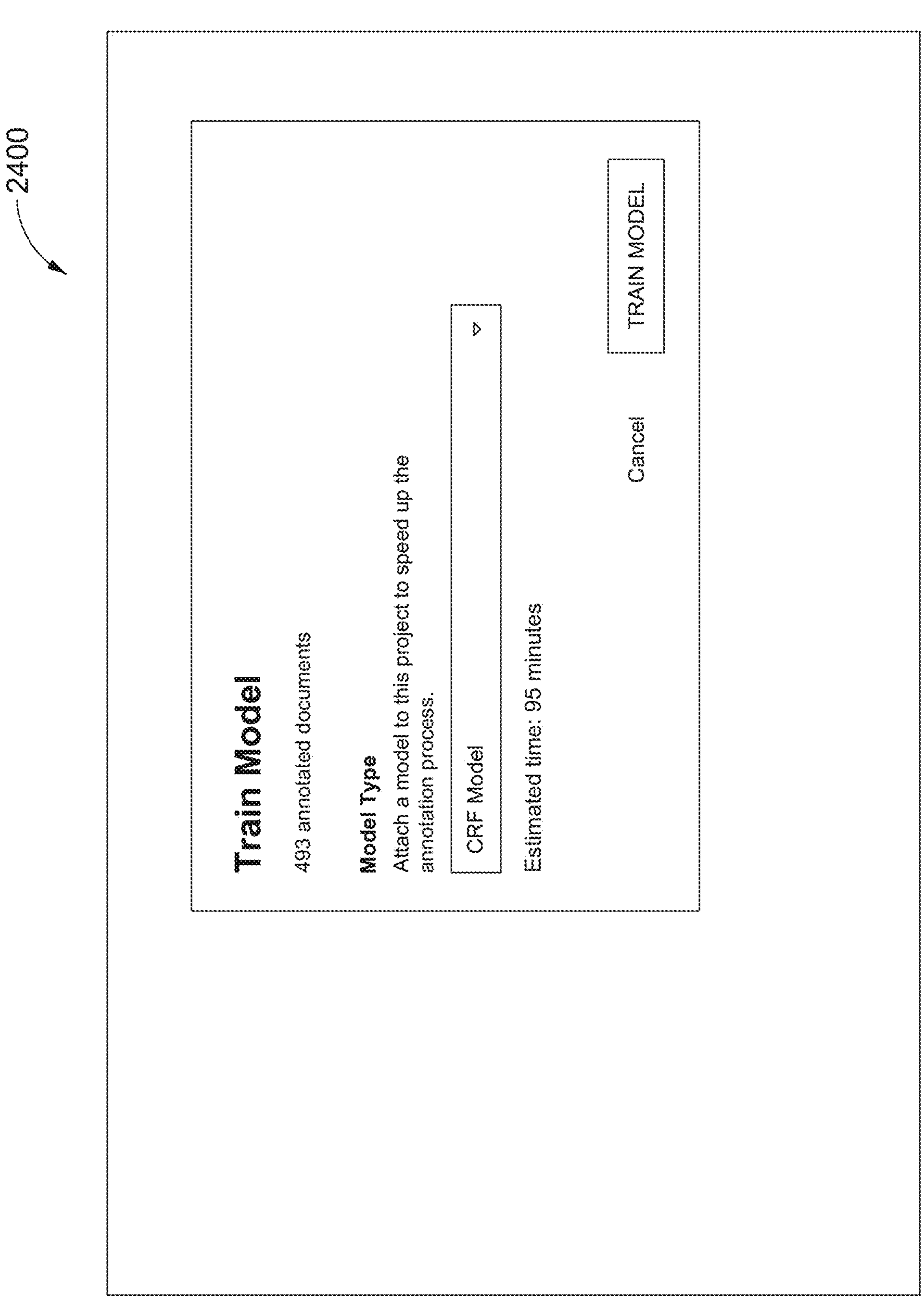
FIG. 25 illustrates a nineteenth screen shot of the AUI providing an option to train a project NLP target model based on annotated documents of a project dataset, according to one inventive implementation.
Figure 26:
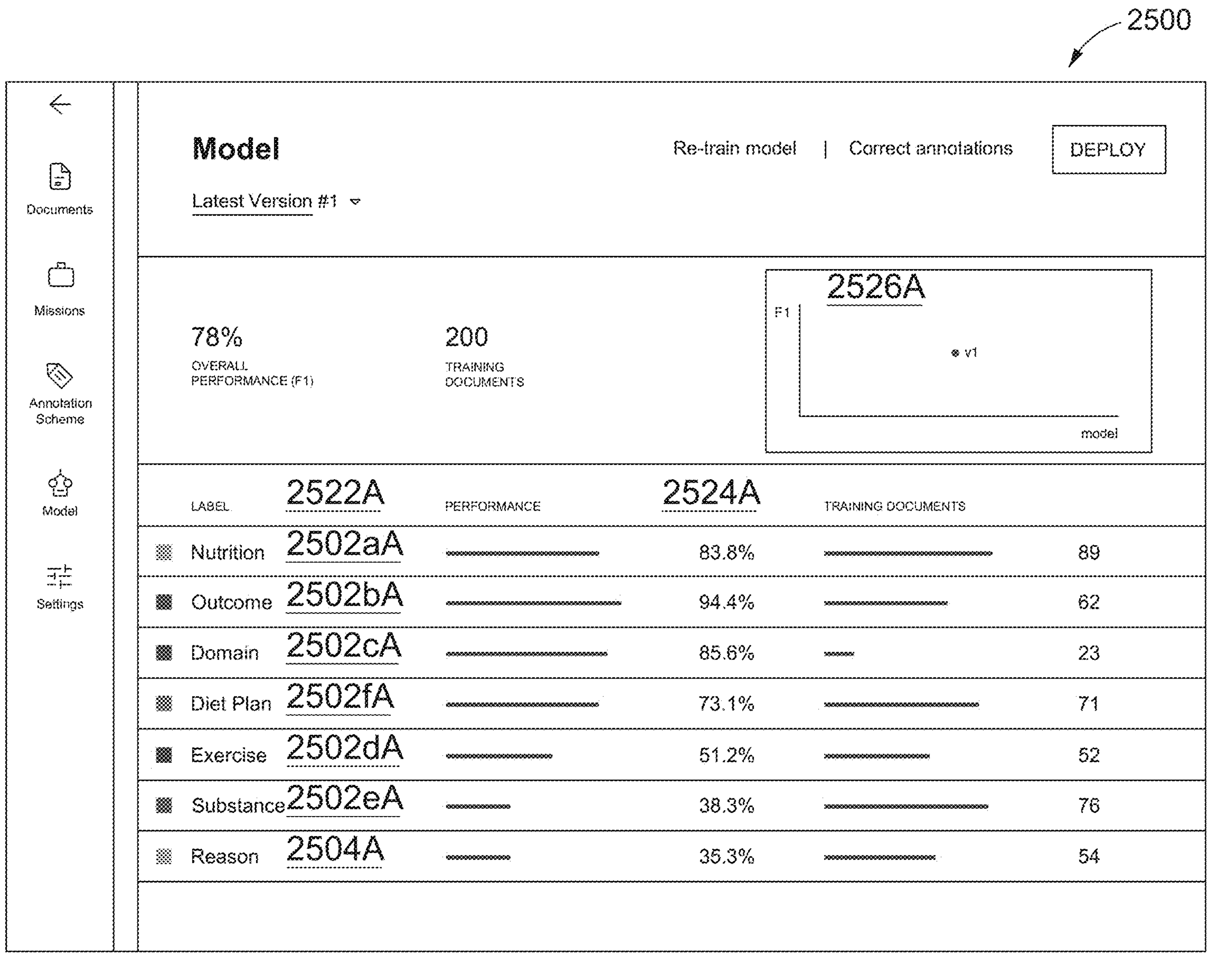
FIG. 26 illustrates a twentieth screen shot of the AUI, in which the model trained in FIG. 25 is applied to unannotated documents of the project dataset to automatically annotate documents, and a first model performance is displayed overall (v1) and with respect to automatically identifying respective entities/concepts corresponding to annotation labels of the annotation scheme, according to one inventive implementation.

FIG. 25 illustrates a nineteenth screen shot 2400 of the AUI that provides an option to train a pre-built project NLP target model based on the annotated documents that were manually annotated by the annotators. FIG. 26 illustrates a twentieth screen shot 2500 of the AUI training a pre-built project NLP model based on the annotated documents that were manually annotated by the annotators. FIG. 26 illustrates an example current state of an initial project NLP target model. The annotation labels 2522A illustrate the annotation scheme dev3339930.eloped for the annotation project. For instance, the annotation labels 2522A include annotation labels for spannotation such as “Nutrition” 2502*a*A (for illustrative purposes as an example, the box on the left to “Nutrition” 2502*a*A is filled with orange color indicating that spannotations that are labelled “Nutrition” 2502*a*A will be highlighted in orange color), “Outcome” 2502*b*A (for illustrative purposes as an example, the box on the left to “Outcome” 2502*b*A is filled with dark blue color indicating that spannotations that are labelled “Outcome” 2502*b*A will be highlighted in dark blue color), “Domain” 2502*c*A (for illustrative purposes as an example, the box on the left to “Domain” 2502*c*A is filled with green color indicating that spannotations that are labelled “Domain” 2502*c*A will be highlighted in green color), “Diet Plan” 2502*f*A (for illustrative purposes as an example, the box on the left to “Diet Plan” 2502*f*A is filled with light blue color indicating that spannotations that are labelled “Diet Plan” 2502*f*A will be highlighted in light blue color), “Exercise” 2502*d*A (for illustrative purposes as an example, the box on the left to “Exercise” 2502*d*A is filled with violet color indicating that spannotations that are labelled “Exercise” 2502*d*A will be highlighted in violet color), and “Substance” 2502*e*A (for illustrative purposes as an example, the box on the left to “Substance” 2502*e*A is filled with pink color indicating that spannotations that are labelled “Substance” 2502*e*A will be highlighted in pink color). The annotation labels 2522A also includes annotation label for spannotation relation such as “Reason” 2504A. Each of the annotation labels 2522A is associated with a performance metric 2524A (also referred to as “F1”). The performance metric 2524A indicates the ability of the project NLP target model to identify spans of texts in the documents that correspond to a respective annotation label 2522A. The plot 2526A helps track project NLP model progress as more and more data is fit to iteratively retrain the model. In this example, the project NLP model is good at identifying ‘Nutrition” 2502*a*A and “Outcome” 2502*b*A. However, the project NLP model in this example has difficulty identifying “Substance” 2502*f*A and “Reason” 2504A. As illustrated in FIG. 26, in the current example the project NLP model is initially trained with 200 documents (other numbers of training documents may be selected in other examples).

Figure 27:
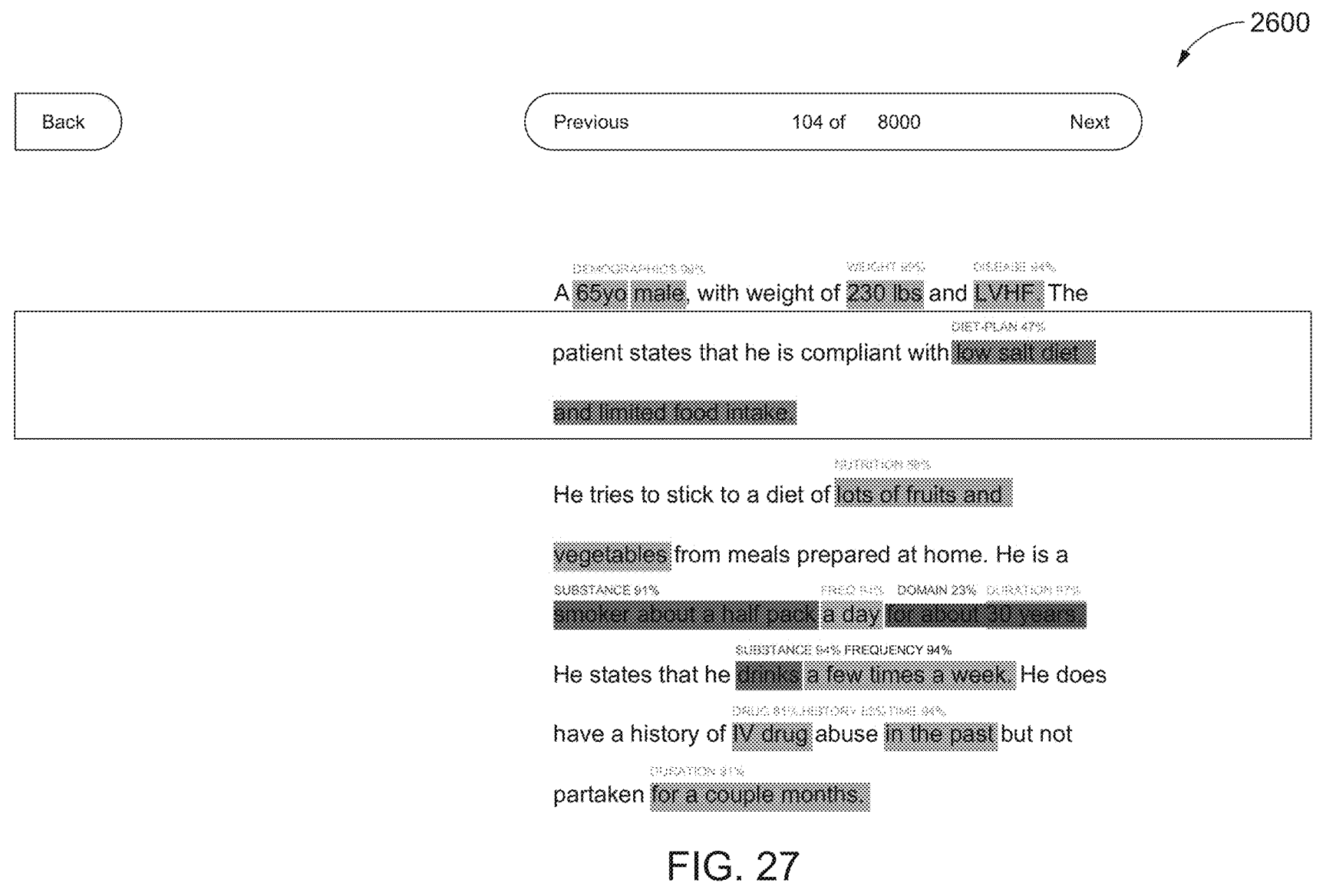

FIG. 27 illustrates a twenty first screen shot 2600 of the AUI predicting annotations in a new document of the annotation project using the initially trained project NLP model. In some inventive aspects, Alpine can select documents from the annotation project for predicting annotations that are most informative to the project NLP model making these automatic annotation predictions. In some inventive aspects, Alpine uses smart sampling to select these documents for automatic annotation by the initially trained project NLP model. For instance, a form of uncertainty sampling may be used where the documents are sampled with a bias in favor of cases where the project NLP target model is highly uncertain. As illustrated in FIG. 27, the document is annotated based on predictions made by the project NLP target model. This document was not previously annotated by a human annotator. However, once the project NLP target model makes annotation predictions, these annotations may be corrected by one or more human annotators. Once the document is corrected by one or more human annotators the document can be used as training data to further improve the project NLP target model.

Figure 28:
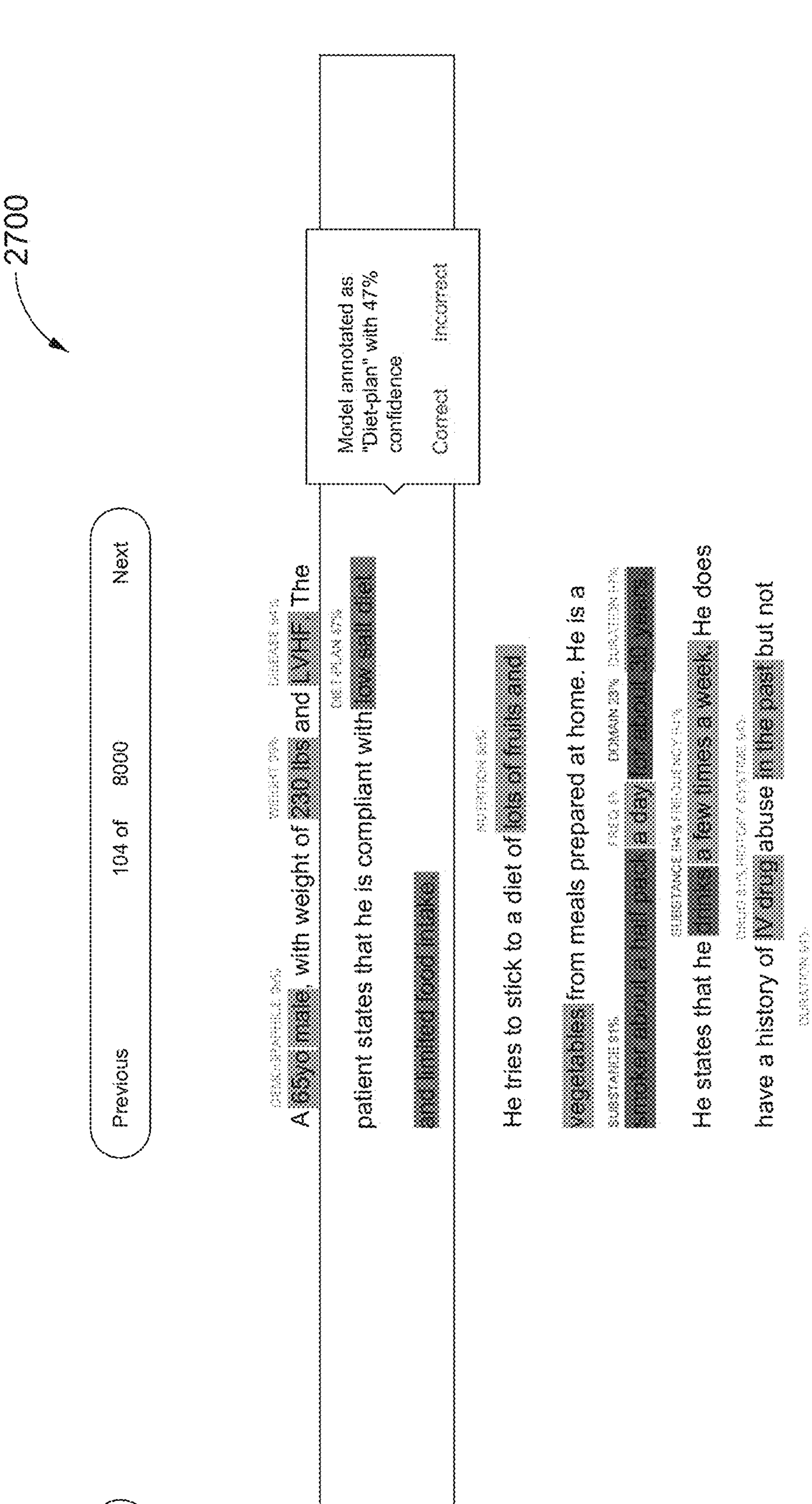
FIG. 28 illustrates a twenty-second screen shot of the AUI, showing the document of FIG. 27 and illustrating how a human annotator may mark one or more model-generated annotations as correct or incorrect, according to one inventive implementation.

FIG. 28 illustrates a twenty second screen shot 2700 of the AUI enabling an annotator to review the predicted annotations by the project NLP target model. The annotator can decide whether the annotations predicted by the project NLP target model are correct and mark the predicted annotation as correct or incorrect accordingly. As the project NLP target model improves, the number of corrections that the annotators have to make to the predicted annotation by the project NLP model will reduce.

Figure 29:
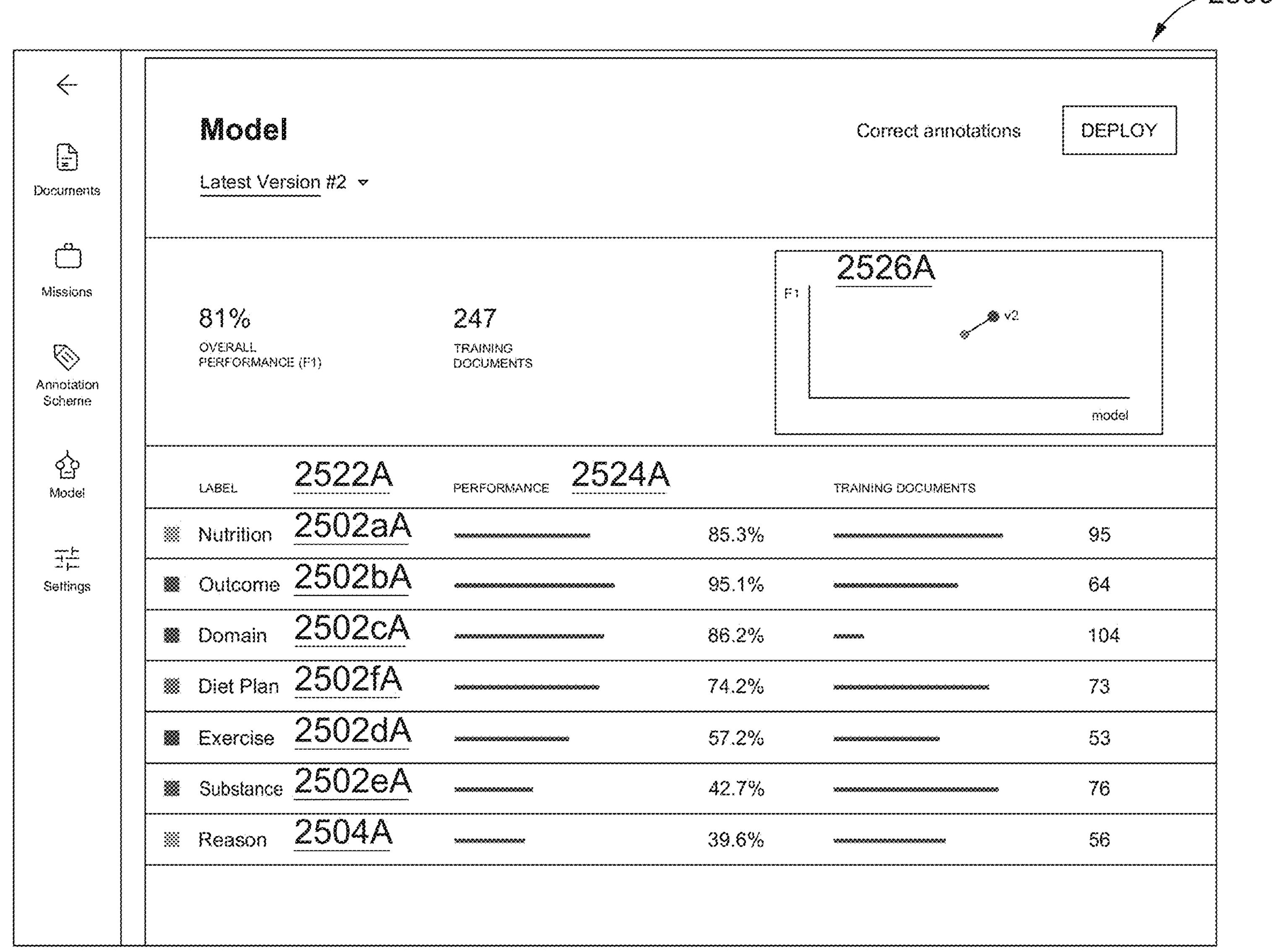
FIG. 29 illustrates a twenty-third screen shot of the AUI, in which the project NLP target model is retrained on additional marked/annotated documents of the project dataset and applied to unannotated/unmarked documents of the project dataset to automatically annotate documents, and a second model performance is displayed overall (v2) and with respect to automatically identifying respective entities/concepts corresponding to annotation labels of the annotation scheme, according to one inventive implementation.

Once the annotator reviews the document, the document can be used as data to re-train the model. FIG. 29 illustrates a twenty third screen shot 2800 of the AUI re-training the project NLP model following inclusion of new data (47 additional documents) after corrections to the annotated predictions by the annotators. As illustrated in FIG. 29, with the inclusion of these additional documents as training data, there is an increase in the performance metric 2524A for each of the annotation labels 2522A in the annotation scheme. The plot 2526A illustrates that the performance metric with respect to the version of the project NLP target model (v2) improves as the version increases. Put differently, the performance metric of initially trained project NLP model (trained with 200 initial documents) is lower than the performance metric of the re-trained project NLP model (trained with 247 documents-47 of which includes corrections to predicted annotations by annotators).

Figure 30:
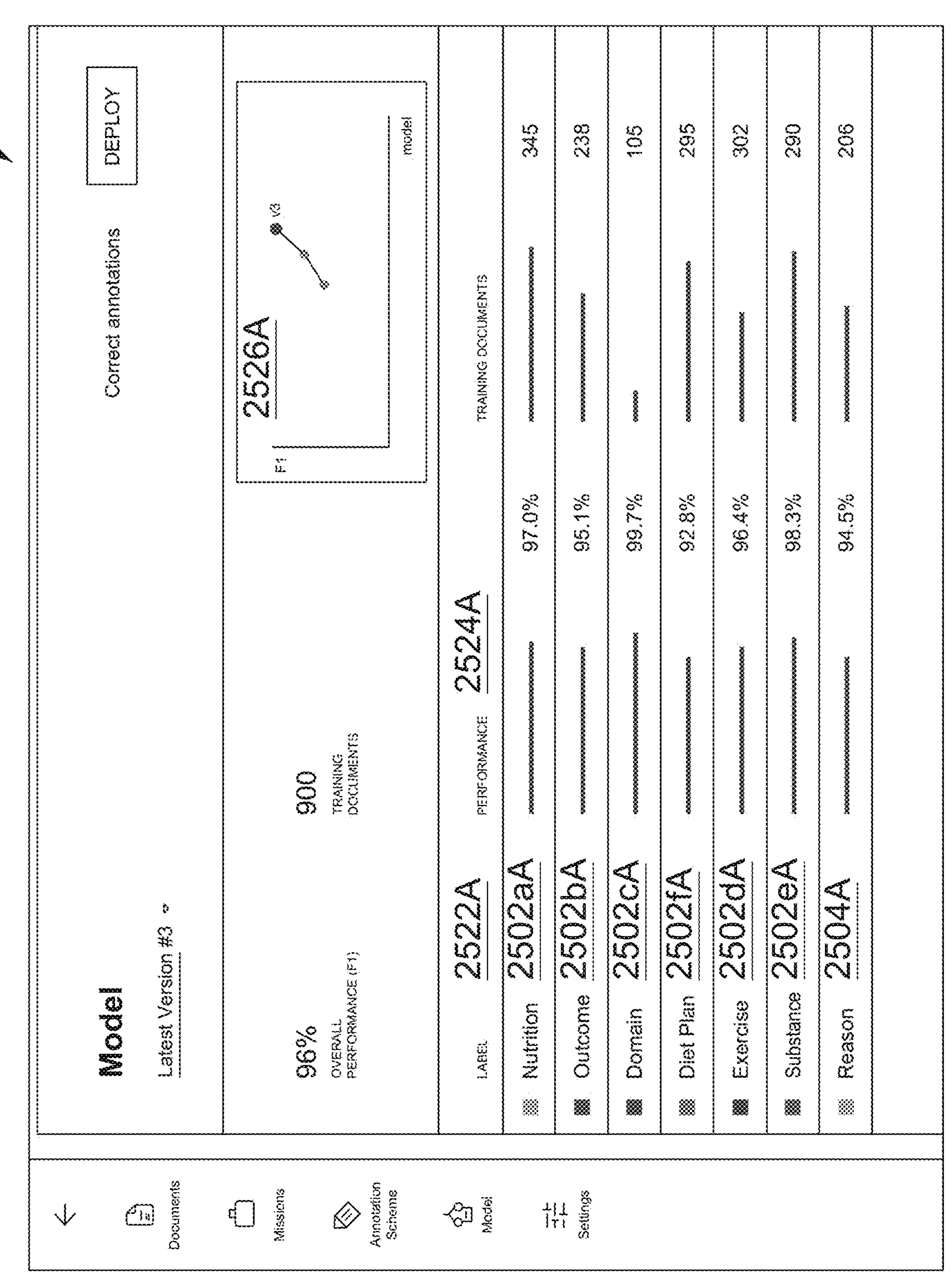
FIG. 30 illustrates a twenty-fourth screen shot of the AUI, in which the project NLP target model is retrained on additional marked/annotated documents of the project dataset and applied to unannotated/unmarked documents of the project dataset to automatically annotate documents, and a third model performance is displayed overall (v3) and with respect to automatically identifying respective entities/concepts corresponding to annotation labels of the annotation scheme, according to one inventive implementation.

FIG. 30 illustrates a twenty fourth screen shot 2900 of the AUI re-training the project NLP model following inclusion of additional data. As illustrated in FIG. 30, by re-training the project NLP model with 900 training documents, the performance metric 2524A for each of the annotation labels 2522A in the annotation scheme increases significantly. For instance, even the annotation labels that the project NLP model had difficulty identifying initially (e.g., "Substance" **2502*f*A and "Reason" 2504A in FIG. 25) have significantly improved performance metrics 2524**A.

Figure 31:
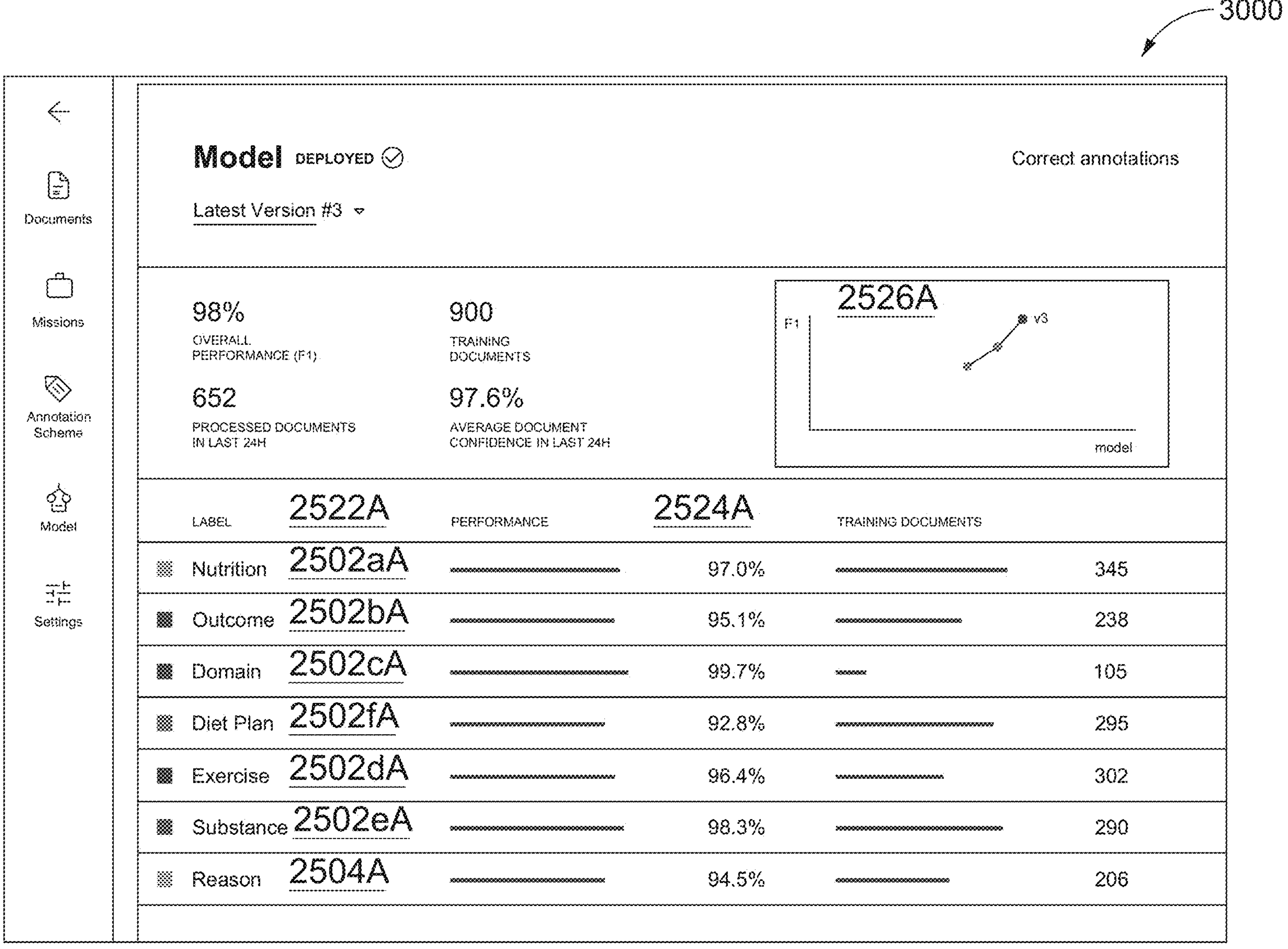
FIG. 31 illustrates a twenty-fifth screen shot of the AUI, showing performance metrics for a deployed project NLP model, according to one inventive implementation.

Once the performance metric of the project NLP model becomes satisfactory, the project NLP model can be deployed to automatically annotate the other documents in the annotation project. FIG. 31 illustrates a twenty fifth screen shot 3000 of the AUI with deployed project NLP model. As illustrated in FIG. 31, the project NLP model has automatically annotated another 652 documents.

Thus, it may be readily appreciated from the foregoing that the active learning framework facilitated by the Alpine AUI enables iterative training of the project NLP target models based on annotated and marked (e.g., corrected) documents all within the same tool. Trained project NLP target models are then deployed to automatically annotate the entire project dataset and thereby identify significant entities and concepts of particular interest to the use-case or business question at hand. These identified entities and concepts constitute structured data extracted from free-form text in the original documents, and in turn may serve as the basis of adding additional structured information to these documents.

To illustrate the foregoing, FIG. 32 illustrates a twenty sixth screen shot 3100 of the AUI, showing the type of structured information (e.g., Roam's NLP Variables) that may be added to respective documents of a project dataset relating to automatic annotations generated by a sufficiently-trained project NLP target model, according to one inventive implementation. As shown in FIG. 32, the labels for the Roam NLP variables include labels in the annotation scheme (e.g., "Disease," "Exercise," "Diet plan"). However, the labels for the Roam NLP variables need not be identical to the labels in the annotation scheme. In some inventive aspects, a user can change the name of labels for the Roam NLP variable using Alpine. Alpine also allows for further meaningful processing based on the project NLP model. In other words, two or more categories in the annotation scheme can be combined and more information can be extracted from different spans to provide meaningful information such as "Mental Disposition." In some inventive aspects, such information that may not be explicitly codified in the RKG can be added to the RKG to enhance and enrich the RKG.

Roam Knowledge Graph (RKG) Architecture

FIG. 33 illustrates an example of an inventive graph-based data storage and retrieval structure referred to herein as a "Roam Knowledge Graph" (RKG) 9100. As noted above, a "knowledge graph" refers to a graph representation of electronic information that may pertain to a particular "domain" or related/overlapping domains of activity and/or knowledge. In various aspects, a Roam Knowledge Graph (RKG) according to the inventive concepts disclosed herein is an effective and highly useful structure for storing and managing data for a variety of use cases and provides specific advantages particularly when data is dynamic (e.g., where regular data updates and/or data growth are important) and when data is heterogeneous and arriving from diverse sources. In other aspects, an RKG particularly facilitates the storage, and automated or semi-automated analysis and modeling, of large bodies of text corpora.

In view of the foregoing, examples of domains for which an RKG similar to that shown in FIG. 33 may be constructed and maintained include, but are not limited to, health care, finance, insurance, e-commerce, entertainment, law, sports, social media, transportation, energy resources and consumption, climate science, education, agriculture, housing, immigration, and other scientific/academic endeavors. In one example discussed herein, an RKG such as the RKG 9100 shown in FIG. 33 may specifically pertain to the health care domain, which encompasses a wide variety of activity and knowledge relating to human health and well-being (e.g., the study and treatment of various ailments and diseases; mitigation and prevention of various ailments and diseases; various forms and techniques of care; diagnoses and administration of drugs; formulation of new drugs, diagnoses and treatments; genes and their relationship to phenotypic expression; various specializations and credentialing for health care practitioners; health care economics, insurance and regulation; and patient demographics).

As illustrated in FIG. 33, in example implementations the RKG 9100 includes multiple subgraphs including at least a first subgraph 9150A and a second subgraph 9150B. The respective subgraphs include "nodes" and "edges" and represent corresponding datasets that pertain to the domain(s) of interest. Each of the subgraphs 9150A and 9150B is linked to a canonical layer 9120 (also referred to herein as a "linking layer" or "semantic layer") of the RKG 9100. Although only two subgraphs 9150A and 9150B are illustrated in FIG. 33 to facilitate an explanation of salient concepts pertaining to the RKG 9100, it should be appreciated that other examples of RKGs pursuant to the various concepts disclosed herein may include more than two subgraphs linked to the canonical layer 9120 (and in many instances significantly more than two subgraphs linked to the canonical layer 9120). As discussed in greater detail below, the canonical layer 9120 of the RKG 9100 generally serves to strategically interconnect and unify information in the underlying datasets represented by the respective subgraphs 9150A and 9150B of the RKG 9100 to provide broader context for the information and facilitate querying and discovery of relationships in the information; in some instances, such relationships may otherwise not be apparent (even to experts in the domain(s) to which the RKG pertains) and/or too complex for human cognition.

Subgraphs Representing Datasets

In general, each of the subgraphs 9150A and 9150B of the RKG 9100 shown in FIG. 33 is a graph representation of a corresponding "dataset" from a particular source, according to a "graph schema." In one aspect, each dataset includes some amount of "structured data," i.e., multiple data elements that can be meaningfully aggregated and that generally are organized as a formatted repository of data elements. In view of the foregoing, a given dataset often includes one or more files representing one or more spreadsheets or database tables with rows and columns, wherein at least some of the rows and or columns include structured data (and wherein the spreadsheets and/or tables also may include row and/or column headers denoting a thing to which the structured data pertains).

A given dataset generally includes information relating to one or more "entities" (things) having particular "entity types" (categories or labels for entities sharing at least one common aspect) that pertain to the domain(s) of interest for which the RKG 100 is constructed and maintained. As shown in FIG. 33, using the health care domain for purposes of illustration, the first subgraph 9150A of the example RKG 9100 represents a first dataset including information relating to the entity type "diseases" and includes representations of the disease entities "Disease 1," "Disease 2," and "Disease 3" according to a first graph schema. The second subgraph 9150B represents a second dataset including information relating to the entity type "drugs" and includes representations of the drug entities "Drug 1" and "Drug 2" according to a second graph schema.

More specifically, in the example RKG 9100 of FIG. 33, each of the subgraphs 9150A and 9150B (as well as the canonical layer 9120) includes multiple "nodes" represented as labeled circles (e.g., one node in the first subgraph 9150A with the label "Disease 2" is shown as node 9152A, and one node in the second subgraph 9150B with the label "Drug 2" is shown as node 9152B). Additionally, at least the first subgraph 9150A of the RKG 9100 also includes multiple edges, wherein each edge is represented as a labeled arrow between two nodes (e.g., one edge in the first subgraph 9150A with the label "HAS_DESCENDENT" is shown as edge 9154A). Thus, each node in the RKG 9100 represents an entity having a particular entity type, each edge represents a relationship of a particular type between two entities, and a graph schema for a given subgraph specifies types for nodes and edges (e.g., corresponding to types of entities and relationships), and a particular arrangement of nodes and edges based on the entities and relationships represented in the corresponding dataset (consider an example in which, in the first subgraph 150A, "Disease 1" is cancer, "Disease 2" is lung cancer, and "Disease 3" is kidney cancer-so Disease 1 is a "parent" to both Disease 2 and Disease 3, thereby giving rise to the relationship "HAS_DESCENDENT").

Regarding nodes in the RKG 9100, each node may have one or more "attributes" (i.e., an identifier, aspect, quality, or characteristic of an entity represented by the node). In example implementations, each node must have at least a primary identifier that is unique in the namespace for the dataset that includes the entity; the primary identifier for a node thus may be different from a name of the corresponding entity that the node represents. As with entities, nodes may be categorized according to different node types, and the node type may be included as an attribute of the node (or may serve as part of the definition for a certain class of nodes corresponding to a particular entity type). Additionally, the label for a node as it appears in a subgraph may be its primary identifier or another attribute associated with the node. For example, the node 9152A in the first subgraph 9150A (representing the entity "Disease 2" from the ICD10 dataset stored in the namespace "CMSICD10," discussed further below) may be defined as a member of the node type class "Disease," and have the unique primary identifier "DIS3265," a name attribute "Disease 2," and have the name attribute assigned as its label in a subgraph representation (as illustrated in FIG. 33). An example description of this node in pseudo-code may be as follows, in which A1, A2 and A3 denote respective attributes of the node:

A1-Node ID: "DIS3295"

A2-Type: "Disease"

A3-Name: "Disease 2"

Regarding edges in the RKG 9100, edges may be similarly categorized according to different types (i.e., of relationships), and a given edge may be associated with a unique primary identifier and one or more attributes. In one aspect, a primary identifier for an edge may be denoted as a "triple" including the primary identifier of the from-node, a descriptor for the type of edge, and the primary identifier of the to-node. For example, the edge 9154A in the first subgraph 9150A shown in FIG. 33 may be denoted as "DIS2555, HAS_DESCENDENT, DIS3295," wherein "DIS2555" is the primary identifier for the node labeled as "Disease 1" and DIS3295 is the primary identifier for the node labeled as "Disease 2." In another aspect, one attribute of an edge may relate to a probability regarding the certainty of the relationship represented by the edge (e.g., a numerical value between 0 and 1, inclusive).

In FIG. 33, the respective datasets represented by the subgraphs 9150A and 9150B generally come from different sources and may be heterogeneous in nature (e.g., vary in data type and/or format). Accordingly, to facilitate data organization and provenance in the structure of the RKG 9100, each of the subgraphs 9150A and 9150B may correspond to (and their underlying codification may be stored in) an isolated "namespace" in computer storage. In illustrative examples, a given namespace generally may be labeled in a manner that somehow identifies the source of the dataset.

For example, the first dataset represented in the first subgraph 9150A of the example RKG 9100 shown in FIG. 33 pertaining to diseases may be the International Classification of Diseases, 10th revision (ICD10) obtained from the Center for Medicare and Medicaid Services (CMS); accordingly, the first dataset (and the underlying codification for the first subgraph) may be logically stored in a first namespace 9156A (e.g., labeled in the example of FIG. 33 as "CMSICD10"). Similarly, the second dataset represented in the second subgraph 9150B pertaining to drugs may be the normalized naming system for generic and branded drugs referred to as RxNorm, obtained from the U.S. National Library of Medicine (NLM); accordingly, the second dataset (and the underlying codification for the second subgraph) may be logically stored in a second namespace 9156B (e.g., labeled in the example of FIG. 33 as "RxNorm").

In view of the foregoing, in the discussion herein a given subgraph of the RKG 9100 may be referred to in some instances by its corresponding namespace label (e.g., in the example of FIG. 33, "CMSICD10" for the first subgraph 9150A, and "RxNorm" for the second subgraph 9150B). Additionally, a given entity type in a particular dataset, as well as a set of nodes having the same type in a corresponding subgraph, may be uniquely identified as a "namespaced entity type" using the hierarchical symbol or nomenclature "Namespace/Entity Type" (e.g., "CMSICD10/Diseases" or "RxNorm/Drugs"). Similarly, a given entity in a particular dataset, as well as a particular node representing that entity in a corresponding subgraph, may be uniquely identified using the hierarchical symbol or nomenclature "Namespace/Entity Type/Entity Identifier" (e.g., "CMSICD10/Diseases/Disease 3" or "RxNorm/Drugs/Drug 1").

Although the example of FIG. 33 illustrates two subgraphs representing datasets pertaining to the health care domain from two particular sources, it should be appreciated that a wide variety of sources may provide datasets pertaining to a wide range of different domains on which an RKG may be based; examples of such sources include, but are not limited to, business entities (public or private companies), academic institutions, research organizations, government agencies, non-profit organizations, news outlets, and individuals.

Additionally, in general, a dataset includes information relating to one or more entities having particular entity types (represented by nodes in a subgraph having particular node types corresponding to the entity types). Examples of different entity types that may be represented in a given dataset (and node types that may be included in a subgraph) include, but are not limited to, physical/tangible objects, places (geographical references), concepts, legal or professional constructs (e.g., companies, organizations, institutions, government agencies, groups and/or networks, and hierarchies within same), products and/or services and various specifications or other information relating to same, events, occupations or roles, professional and/or academic credentials or specialization, publications, financial information, demographic information, statistical information, health-related information (e.g., diagnoses, medical conditions, symptoms, medical research information), and ontologies. A dataset also may include information indicating certain "relationships" between multiple entities, i.e., a nexus between two entities of the same type or different types (represented in a subgraph by an edge/labeled arrow between two nodes). A given dataset may also include information relating to one or more attributes of a given entity or a particular relationship between multiple entities (e.g., an aspect, quality, or characteristic of an entity or a relationship).

In connection with the health care domain, although the datasets represented by the subgraphs 9150A and 9150B shown in FIG. 33 respectively relate to diseases and drugs for purposes of illustration, it should be appreciated that a wide variety of datasets pertaining in some fashion to the health care domain may be represented in the RKG 9100. Examples of such datasets include, but are not limited to, public health statistics and databases, adverse event databases, regulatory documents, insurance company policy documents, electronic medical records, patient surveys, insurance claims, Medical Science Liaison (MSL) notes, Medical Information Requests (MIRs), and medical ontologies obtained from various sources (e.g., the Unified Medical Language System from the U.S. National Library of Medicine, RxNorm, SNOMED CT (Systemized Nomenclature of Medicine), SNOP (Systemized Nomenclature of Pathology), the GALEN Common Reference Model, the National Drug Data File (NDDF), the International Statistical Classification of Diseases and Related Health Problems (ICD10), Chemical Entities of Biological Interest (ChEBI), Current Procedural Terminology (CPT), the Anatomical Therapeutic Chemical (ATC) classification system including Defined Daily Doses (DDD), the International Classification of Functioning, Disability and Health (ICF), LOINC, and the Medical Dictionary for Regulatory Activities (MedDRA)).

Canonical Layer

In the example RKG 9100 shown in FIG. 33, the canonical layer 9120 (also referred to as a "semantic layer" or a "linking layer") includes a set of linking nodes 9122A, 9122B, 9122C, 9124A and 9124B (also referred to as "canonical nodes") of predetermined node types ("canonical node types") logically stored in a separate namespace 9126 of computer storage for the RKG (e.g., the namespace 9126 is labeled in the example of FIG. 33 as "roam"). The canonical nodes in the canonical layer 9120 are connected via linking edges to corresponding (or closely corresponding) nodes in the subgraphs 9150A and 9150B in respective isolated namespaces of the RKG 9100.

In one aspect of an RKG according to the concepts disclosed herein, the canonical layer of an RKG is the only means by which multiple subgraphs of the RKG are interconnected. Stated differently, there is no direct connection via an edge between any node in one subgraph and any node in another subgraph; rather, all edges from a given subgraph in an isolated namespace of an RKG connect that subgraph only to the canonical layer of the RKG and not another subgraph. This aspect can be readily observed in the example of FIG. 33, in which there are no edges between any node in the first subgraph 9150A in the namespace "CMSICD10" and any node in the second subgraph 9150B in the namespace "RxNorm," and there are only edges between these subgraphs and the canonical layer 9120 in the namespace "roam."

In various implementations of an RKG pursuant to the concepts disclosed herein, the canonical node types for the canonical nodes of the canonical layer of an RKG correspond to selected node types that: 1) are present in multiple subgraphs of the RKG, or present in one subgraph of the RKG and likely to appear in one or more other datasets pertaining to the information domain (that may be later added to the RKG as one or more new subgraphs); and 2) have some significance in the information domain(s) (e.g., ontology or ontologies) on which the RKG is based.

In general, for a given domain or domains on which an RKG may be based, canonical node types may be designated based at least in part on an initial analysis of the respective datasets in isolated namespaces to be joined by the canonical layer to assess the prevalence, and/or present or prospective significance in the domain(s), of certain entity types that appear in one or more of the datasets. For example, in an RKG based on multiple datasets relating to global economics, one entity type of prevalence and/or significance may be different countries present in the dataset; accordingly, one canonical node type may be "Country." Similarly, another canonical node type for an RKG based on multiple datasets relating to global economics may be "Currency Unit," another canonical node type may be "Reserve Chairperson," and another canonical node type may be "Exchange Rate." In some aspects, selection of canonical node types involves a strategic decision, based in part on knowledge of the domain(s) of interest, to choose entities that link multiple (and often otherwise isolated) datasets in meaningful ways to provide a broader context for the collection of information in the respective datasets. This linking of respective datasets via strategic selection of linking entities in turn facilitates identification of relationships in the collection of information that may otherwise not be apparent without the greater context provided by an RKG, and/or too complex for human cognition.

In view of the foregoing, examples of canonical node types for the health care domain include, but are not limited to: Disease (e.g., see the nodes 9122A, 9122B and 9122C in the canonical layer 9120 of FIG. 33), Drug (e.g., see the nodes 9124A and 9124B in the canonical layer 9120 of FIG. 33), FDA device code, FDA device name, Geography (e.g., address, census region, city, country, county, geocoordinates, MSA code, state, zip code), Health Care Organization, Health Care Professional, Hospital, Manufacturer, Procedure, Industry Event, Time, and Specialty (e.g., specialization, classification, grouping). As noted above in connection with subgraphs, the respective canonical node types in an RKG may be uniquely identified using the hierarchical symbol or nomenclature "Canonical Layer Namespace/Canonical Node Type" (e.g., "roam/Disease" or "roam/Drug").

In the example RKG 9100 of FIG. 33, two canonical node types (i.e., roam/Disease and roam/Drug) are present in the canonical layer 9120, and these two node types exactly correspond to the different node types shown in the subgraphs 9150A and 9150B of the RKG 9100. However, it should be appreciated that the canonical node types present in the canonical layer of an RKG according to the concepts disclosed herein need not necessarily include all of the node types present in the multiple subgraphs of the RKG (i.e., there may be some node types present in one or more subgraphs that do not have a corresponding canonical node type in the canonical layer of the RKG). Accordingly, unlike the example RKG 9100 shown in FIG. 33, the canonical layer of another RKG may include (and generally does include) a quantity of canonical nodes that is less than (and sometimes significantly less than) the sum of all nodes present in the multiple subgraphs of the RKG. Additionally, there is no logical limit to the number of different canonical node types that may be selected for the canonical layer of an RKG (and corresponding number of canonical nodes themselves); again, as noted above, salient criteria for selecting canonical node types for the canonical layer is that they have some significance in the information domain(s) on which the RKG is based and are present in one or more subgraphs of the RKG. Regardless of its canonical node type, each canonical node is unique in the canonical layer (it is only found once in the canonical layer); stated differently, each canonical entity is represented uniquely by only one node in the canonical layer.

In the example RKG 9100 shown in FIG. 33, a given canonical node in the canonical layer is identical to (e.g., a "clone" of, or deemed to be sufficiently related to) a corresponding subgraph node that appears in at least one subgraph of the RKG. Accordingly, the corresponding subgraph node is connected to the canonical node by an edge of the type "IS" (e.g., see the node 9152A in the first subgraph 9150A connected to the canonical node 9122B in the canonical layer 9120 via an arrow labeled as "IS"). More generally, for an RKG according to the concepts disclosed herein, each edge between a canonical node in the canonical layer and a corresponding node in one or more subgraphs of the RKG is one of the following types: "IS," "IS_PART_OF," or "CONTAINS" (or other terms designating substantially similar relationships, such as "INCLUDES," "IS_INCLUDED_IN," "ENCOMPASSES," "SUBSUMES," and the like). In some implementations, the direction of a labeled arrow denoting an edge between a node in one or more subgraphs and a canonical node may be toward the canonical node, as shown in FIG. 33; however, it should be appreciated that in other implementations the direction of a labeled arrow representing an edge may be from the canonical node to one or more subgraph nodes.

Although each of the canonical nodes in the canonical layer 9120 of the example RKG 9100 shown in FIG. 33 is connected to only one node in one subgraph of the RKG 9100, these canonical nodes may nonetheless be of particular significance in the information domain such that they are expected to be connected to one or more new subgraph nodes at a future time (e.g., as one or more additional datasets pertaining to the information domain(s) are added to the RKG in corresponding new namespaces). In other implementations of an RKG, identical or closely related nodes to a given canonical node ("clone" nodes) appear in at least two subgraphs in different namespaces of the RKG; in this case, at least one canonical node in the canonical layer is connected via multiple edges to at least two corresponding nodes in respective subgraphs in different namespaces of the RKG (and in some implementations, most or all of the canonical nodes are connected to multiple subgraphs in this manner).

Figure 34:
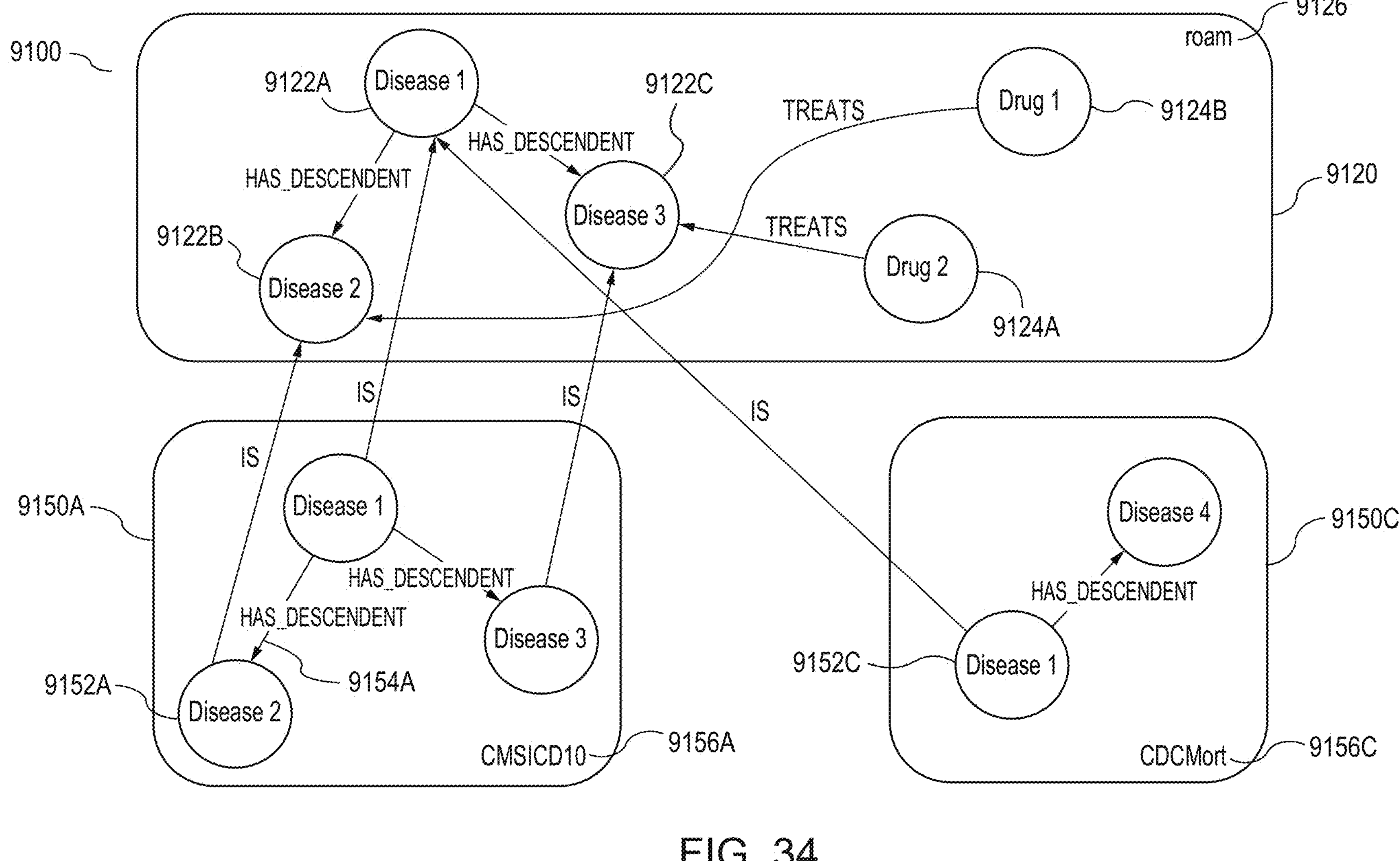
FIG. 34 illustrates the example RKG of FIG. 33 with an additional subgraph, according to one inventive implementation.

FIG. 34 illustrates the foregoing concept. FIG. 34 is based on the RKG 9100 shown in FIG. 33, in which a new third subgraph 9150C has been added to the RKG 9100 (and the second subgraph 9150B is not shown in FIG. 34 to facilitate clarity of the illustration). In FIG. 34, the third subgraph 9150C represents a third dataset pertaining to underlying causes of death in the U.S. obtained from the U.S. Center for Disease Control, in which certain diseases appear as entities; accordingly, the third dataset (and the underlying codification for the third subgraph) is logically stored in a third namespace 9156C (e.g., labeled in the example of FIG. 34 as "CDCMort"). The third subgraph 9150C includes multiple nodes having a node type "Disease," such as the node 9152C with the label "Disease 1." The node 9152C corresponds to the canonical node 9122A (also "Disease 1"-both nodes represent the same entity); accordingly, the canonical node 9122A is not only connected via an "IS" edge (represented by an arrow labeled as "IS") to the node labeled as "Disease 1" in the first subgraph 9150A, but it is also connected via an "IS" edge to the node 9152C in the third subgraph 9150C. In this manner, the canonical node 9122A links the first subgraph 9150A and the third subgraph 9150C.

The example shown in FIG. 34 of the RKG 9100 in which the canonical layer 9120 links two (or more) subgraphs illustrates particular advantages of the canonical layer (and thus the RKG itself) in various implementations. For example, without the canonical layer, if one wanted to directly interconnect (with edges of the type "IS") respective nodes in different subgraphs representing (or deemed to represent) the same entity, one would need to rely on the conventional mathematical construct of a "combination" to determine the number of edges of the type "IS" that would be required to completely interconnect these nodes. More specifically, for a set of n nodes representing (or deemed to represent) the same entities in different subgraphs, the number of edges needed to directly and completely connect respective pairs of the n nodes between the different subgraphs is given by the binomial coefficient:

$$\binom{n}{k} = \frac{n!}{k!(n-k)!}$$

where k=2, and where the binomial coefficient is often colloquially referred to as "n choose k" (or, in the present example, "n choose 2"). In the example of FIG. 34 in which there are only two subgraphs and hence only two nodes to connect (n=2), without the canonical layer only one edge would be required to connect the two corresponding nodes. However, considering an example in which there are ten different subgraphs each containing the node "Disease 1," according to the binomial coefficient above 45 edges would be required to pairwise interconnect these nodes directly (10 choose 2=45).

With the foregoing in mind, using the canonical layer 9120 containing the canonical node "Disease 1" to provide a linking node for the ten subgraphs in the example above, only ten edges would be required to fully interconnect each of the "Disease 1" nodes in the ten different subgraphs to the canonical node "Disease 1" in the canonical layer 9120 (i.e., one edge per subgraph). In this manner, the canonical layer provides for a substantial reduction of graph complexity (e.g., number of edges) required to interconnect respective corresponding nodes in different subgraphs. This in turn offers distinct advantages as the number of subgraphs (and the number of corresponding nodes in different subgraphs) increases for the particular domain(s) of interest; examples of such advantages include, but are not limited to, reductions in data storage and retrieval times, enhanced query/search efficacy and discovery of relationships in different parts of the RKG, enhanced ability to infer relationships in different parts of the RKG, and enhanced ability to train data models for natural language processing (NLP) and other purposes (e.g., using machine learning techniques) based on information extracted from the RKG.

Within the canonical layer of an RKG, a given canonical node may be connected to one or more other canonical nodes via respective edges of a wide variety of types, based at least in part on the diverse relationships that may exist between canonical nodes of the same type or different types. For example, as shown in FIG. 33, the canonical node 9124A ("Drug 2") is connected via an edge of the type "TREATS" to the canonical node 9122C ("Disease 3"); similarly, the canonical node 9124B ("Drug 1") is connected via an edge of the type "TREATS" to the canonical node 9122B ("Disease 2").

More generally, as discussed in greater detail below, edges between subgraph nodes and canonical nodes, or between any two canonical nodes, may be generated based at least in part on: 1) one or more particular attributes of the respective nodes, 2) relationships between entities specified in some manner by the underlying information in the datasets represented by the subgraphs of the RKG, and/or 3) trained models that predict (based on a variety of criteria coded in logic for the model) that the nodes should be connected as having some particular type of articulated relationship (with some corresponding probability).

For example, edges may be generated between subgraph nodes and canonical nodes of certain types (or between two canonical nodes) pursuant to defined logic based on a variety of criteria (e.g., connect subgraph node of type X to canonical node of type X with an edge of type "IS" if the respective primary identifiers of the nodes match; connect subgraph node of type Y to canonical node of type Y with an edge of type "IS" if respective attributes A1, A3 and A5 have the same values for the respective nodes).

In other instances, an edge may be generated between a subgraph node and a canonical node, or between two canonical nodes, based on a trained model (also referred to herein further below as a "model-based connector") that predicts in some respect the relationship between the nodes. More specifically, a trained model may be codified to connect subgraph node A of type X to canonical node B of type X with an edge of type "IS" if the model predicts (based on a variety of criteria coded in the logic for the model) that these nodes should be connected with some degree of certainty (e.g., if at least one of respective attributes A1, A2 and A3 for each node is substantially similar, with some certainty), wherein the degree of certainty may be recorded as a probability attribute of the edge of type "IS" (e.g., using a number from 0 to 1, inclusive). Consider an example in which a canonical node A for a node type "Professional Practitioner" has the attributes {A1-First Name: "Erunia," A2-Last Name: "Agbekele," A3-Profession: "Biologist"}, and a subgraph node B of the same node type includes the attributes {A1-First Name: "E.," A2-Last Name: "Agbekle," A3-Profession: "Biol"}. A model-based connector (trained model) evaluating these nodes may be codified to generate an edge of type "IS" between these two nodes, with some appreciable certainty (e.g., the edge type "IS" may have a probability attribute of 0.93 pursuant to certain parameters of the model), even though none of the respective attributes is identical for the respective nodes.

In various instantiations, the RKG 9100 illustrated in FIG. 33 may be created and maintained using a graph database management system, examples of which include, but are not limited to, Amazon Neptune, Neo4j, Open Link Virtuoso, and OrientDB. The RKG may be represented in a variety of graph-specific file formats, examples of which include, but are not limited to, GraphML, DOT (used by the program Graphvix), RDF (Resource Description Framework), OWL, and GML. The RKG also may be represented in more general file formats such as CSV, JSON and XML. In general, suitable file formats and database management systems for an RKG pursuant to the concepts disclosed herein allow for 1) various node types, 2) various edge types, 3) directed edges, 4) node and edge attributes having at least the types "string," "integer," "float," and lists thereof, and 5) multiple edges between pairs of nodes.

Building a Roam Knowledge Graph (RKG)

Having discussed above the general structure of an RKG pursuant to the inventive concepts herein, the disclosure now turns to inventive methods for building an RKG.

As an initial matter, the information domain(s) for which an RKG is desired is/are first specified, such that multiple datasets from one or more sources may be preliminarily identified that are available and germane to the domain(s) of interest. In one aspect, there is theoretically no limit on the number of datasets that may be considered in the first instance for an RKG (any such limitations may arise, based in at least in part, on the particular graph-specific file format and/or graph database management system employed to create and maintain an RKG). As a general premise, an RKG has notable utility in providing links between two or more datasets, particularly when one or more of the datasets includes dynamic information (e.g., where regular data updates and/or data growth are important) and when the datasets are heterogeneous and arriving from diverse sources.

As noted above, in one aspect, each dataset includes some amount of "structured data" (i.e., multiple data elements that can be meaningfully aggregated and that generally are organized as a formatted repository of data elements) or "semi-structured data" (e.g., having some organizational structure). In particular, a given dataset often includes one or more files representing one or more spreadsheets or database tables with rows and columns, wherein at least some of the rows and or columns include structured data (and wherein the spreadsheets and/or tables also may include row and/or column headers denoting one or more entity types to which the structured data pertains). In some implementations discussed further below, some datasets or files that may be germane to the domain(s) of interest (and hence are suitable candidates for inclusion in an RKG) may contain significant amounts of "unstructured data" (e.g., free-form text). To facilitate inclusion in an RKG of information contained in unstructured data, datasets or files containing such unstructured data may be pre-processed (e.g., according to various machine learning or natural language processing techniques, as discussed further below) to provide at least some structured or semi-structured data in the datasets/files, such that these datasets would be suitable for the inventive graph-building methods discussed herein.

In a given implementation of an RKG, one or more datasets may be obtained from various sources of public information (e.g., government agencies, regulatory bodies, academic or professional institutions or consortia, private companies that maintain public databases, etc.) relating to a given domain or related domains. In some instances, one or more datasets under consideration may be deemed to be a "fundamental dataset" (also referred to herein as a "golden dataset"), i.e., a dataset of factual information from a trusted (and often public) source. In some implementations, one or more such fundamental datasets may be instructive, at least in part, toward the preliminary selection of canonical node types for the canonical layer of an RKG (given the particular entities included in the fundamental dataset(s) and the other information in the dataset(s) pertaining to these entities). In connection with the health care domain, examples of fundamental datasets include, but are not limited to, a list of United States zip codes obtained from the U.S. Postal Service, and National Provider Identifier (NPI) records of health care practitioners obtained from the National Plan and Provider Enumeration System (NPPES) of the U.S. Department of Health and Human Services. In some implementations of an RKG pursuant to the present disclosure, several (if not a majority or in some cases all) of the datasets on which the RKG is based may be fundamental or golden datasets.

Selection of Canonical Node Types

In general, for a given domain or domains on which an RKG may be based, in example implementations canonical node types for the canonical layer may be designated based at least in part on an initial analysis of the respective datasets in isolated namespaces to be joined by the canonical layer (and particularly fundamental datasets) to assess the prevalence, and/or present or prospective significance in the domain(s), of certain entity types that appear in one or more of the datasets. For example, in an RKG based on multiple datasets relating to the domain of "global economics," one entity type of prevalence and/or significance in multiple datasets may be different countries present in the datasets; accordingly, one canonical node type in an RKG pertaining to global economics may be "Country." Similarly, based on other entities present and of some significance in the multiple datasets, another canonical node type for an RKG relating to global economics may be "Currency Unit," another canonical node type may be "Reserve Chairperson," and another canonical node type may be "Exchange Rate."

As noted above, in some aspects selection of canonical node types involves a strategic decision, based in part on knowledge of the domain(s) of interest, to choose entities of certain types that link multiple (and often otherwise isolated) datasets in meaningful ways to provide a broader context for the collection of information in the respective datasets. This linking of respective datasets via strategic selection of linking entity types corresponding to canonical node types in the canonical layer of an RKG in turn facilitates identification, via the RKG once built, of relationships in the collection of information that may otherwise not be apparent without the greater context provided by the RKG and its inventive structure, and/or too complex for human cognition.

With reference again to the example RKG 9100 shown in FIGS. 33 and 34 and the canonical layer 9120 in the namespace "roam," two canonical node types are shown generally relating to the health care domain (i.e., "Disease" and "Drug"). Based on the foregoing discussion regarding the designation of canonical node types in a given domain, and in particular consideration of the health care domain, examples of canonical node types derived from an analysis of a variety of public datasets from different sources relating to the health care domain on which an RKG similar to the RKG 9100 may be based, include, but are not limited to:

roam/Disease
roam/Drug
roam/FDADeviceCode
roam/FDADeviceName
roam/Geography
roam/HealthCareOrganization
roam/HealthCareProfessional
roam/Hospital
roam/Manufacturer
roam/Procedure
roam/IndustryEvent
roam/Time
roam/Specialty In another aspect, it should be appreciated that the canonical node types in the canonical layer of an RKG may change over time. For example, as one or more of the initial datasets on which an RKG is based are updated and/or evolve over time, and/or as one or more new datasets are identified (and stored in one or more new isolated namespaces) to be represented as subgraphs and connected to the canonical layer of an RKG, new entity types in the datasets may be identified as appropriate candidates for augmenting the canonical layer with additional canonical node types (e.g., based on various criteria similar to those discussed above).

Ingesting and "Cleaning" a Dataset

Figure 35:
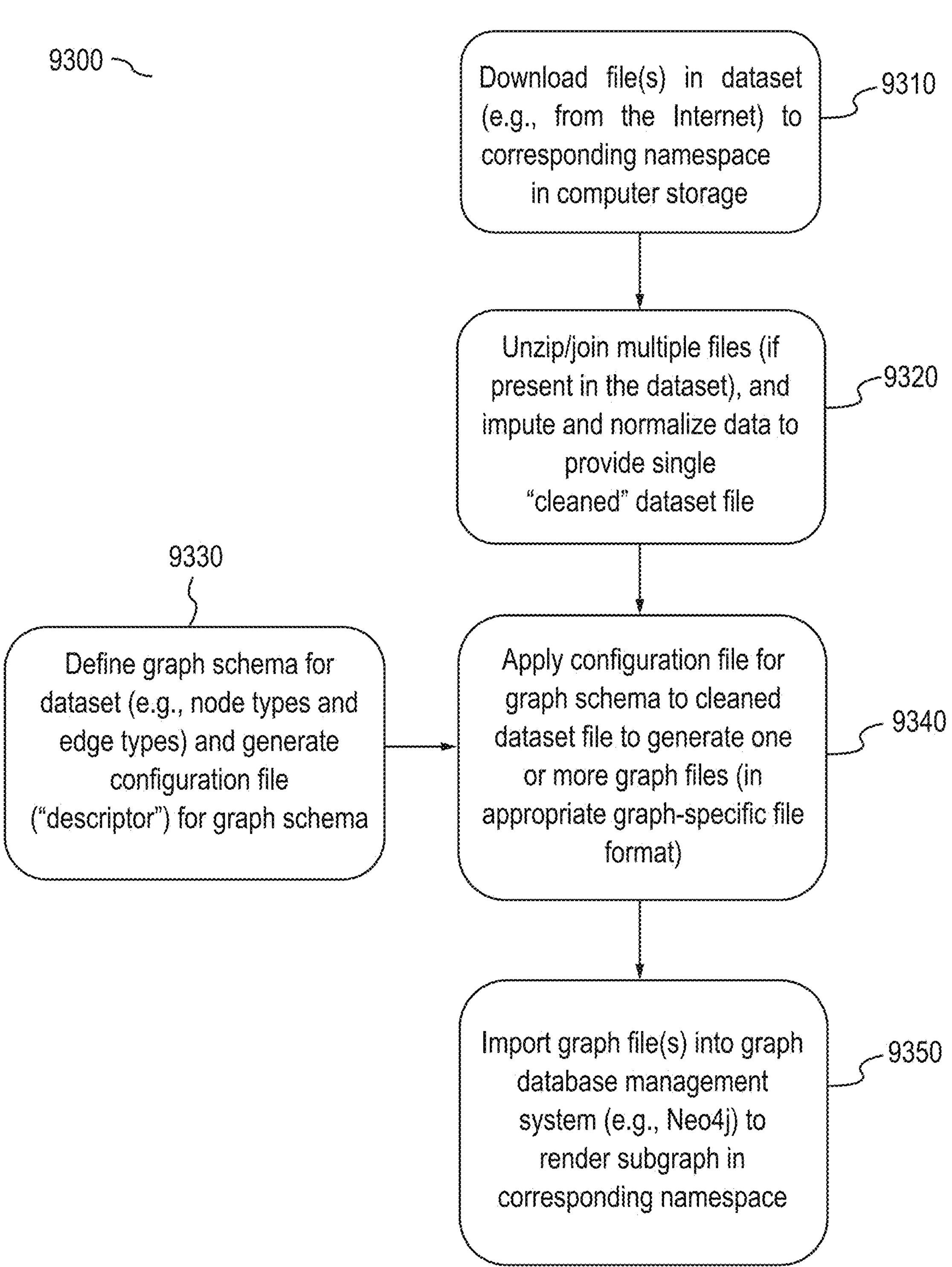
FIG. 35 illustrates an example method for ingesting datasets and generating subgraphs representing the datasets for the RKG of FIG. 33, according to inventive implementations.

Available datasets pertaining to the domain(s) of interest may be respectively downloaded (e.g., from the Internet) and imported into corresponding isolated namespaces of computer storage (which namespaces may be labeled, based at least in part, on the source of the dataset). Thereafter, a given dataset may be processed so as to generate a subgraph representing the dataset. FIG. 35 illustrates an example method 9300 for ingesting a given dataset and generating a subgraph representing the dataset, according to inventive implementations. In the discussion that follows, it should be appreciated that the method 9300 outlined in FIG. 35 may be applied, in whole or in part, in a parallel or serial fashion to ingest multiple datasets and generate corresponding subgraphs representing the datasets. For example, with reference again to the RKG 9100 of FIG. 33, the method 9300 may be applied to each of the two datasets in the respective namespaces "CMSICD10" and "RxNorm" (e.g., sequentially or contemporaneously) to generate the corresponding subgraphs 9150A and 9150B of the RKG 9100.

In block 9310 of FIG. 35, a given dataset may include one or more files that are downloaded to a corresponding namespace in computer storage. For example, one or more files in a dataset may be downloaded via the Internet from a website that provides a portal to an Internet-coupled server or servers maintained by (or providing hosting services to) the source of the dataset. In one example implementation, the method employs conventional techniques to crawl the Internet and download the one or more files relating to the dataset. In some instances, multiple files for a given dataset are obtained from the source as zipped files, and/or the file(s) may be in a particular file format or different file formats (e.g., .csv, json).

In block 9320 of FIG. 35, if the dataset includes related information spread across multiple files, and the files may be zipped, the files for the dataset are unzipped if necessary and joined (e.g., in the sense of a relational database) to create a single file for the dataset (e.g., a single .csv file). Missing values in the data that are known or readily obvious may be imputed (filled in) in a basic sense to generally maintain the integrity of the data in the dataset (e.g., if it is known that a zip file from a particular source includes one file per country, a "country" value can be entered into an appropriate field of the single file representing the joined and unzipped separate files of the ingested dataset). In some implementations, as part of block 9320, at least some of the data in the single file representing the dataset may be "normalized" (or "canonicalized"), i.e., modified in some respect according to a predetermined standard or format so it may be more readily compared to other pieces of data (e.g., in other datasets) relating to the same or similar thing. This process in block 9320 of joining, imputing and/or normalizing may be generally referred to herein as "cleaning," such that a single "cleaned" dataset file is generated in block 9320 based on the originally-ingested dataset.

Building a Subgraph

In block 9330 of the method 9300 shown in FIG. 35, a "graph schema" is created for the dataset to define the node types and the edge types that are used in the subgraph to represent the dataset. In one aspect, the definition of node types and edge types in the graph schema for a given dataset may be based at least in part on the specification of canonical node types for the canonical layer of an RKG. This ensures that at least one of the node types defined in the graph schema for the dataset corresponds to an identical (or substantially similar) canonical node type in the canonical layer of the RKG, to thereby facilitate connection of the subgraph representing the dataset, via an edge of the type "IS" or similar type, to the canonical layer of the RKG, as discussed further below.

The graph schema for a given dataset may be encoded in various manners (e.g., using a suitable coding language and/or file format) to generate a configuration file (also referred to herein as a "descriptor file") defining the graph schema. For example, provided below is an excerpt of a descriptor file, using the Python programming language, to define a graph schema for generating a subgraph for the National Provider Identifier (NPI) dataset, obtained from the National Plan and Provider Enumeration System (NPPES) of the U.S. Department of Health and Human Services and ingested into a namespace "NPI" in computer storage. Although an NPI dataset is not represented in the example RKG 9100 shown in FIGS. 33 and 34, the graph schema defined by the code reproduced immediately below for the NPI dataset illustrates a number of relevant concepts generally applicable to graph schema for subgraphs of an RKG (including the relatively simpler graph schema employed to generate the subgraphs 9150A, 9150B and 9150C shown in FIGS. 33 and 34).

In particular, in creating the example graph schema for the NPI dataset, the descriptor file below defines the node types "Provider," "Address," "Specialization," "Credentials," "AuthorizedOfficial," and "State." For each of these node types, the descriptor file also defines one or more attributes of the node type. Given these node types, the descriptor file for the graph schema also defines edge types between particular pairs of node types as follows (using the "triple" format):

AuthorizedOfficial, REPRESENTS, Provider
Provider, HAS_CREDENTIALS, Credentials
AuthorizedOfficial, HAS_CREDENTIALS, Credentials
Provider, MAILING ADDRESS, Address
Provider, PRACTICE LOCATION, Address
Provider, SPECIALIZES_IN, Specialization
Provider, LICENSED_IN, State The code excerpt for this descriptor file, in the Python programming language, is as follows:

```
namespace = Namespace('NPI')
# Provider
provider_abstract_node = AbstractNode(namespace, 'Provider')
provider_attr_keys = {
'entity_type',
'is_organization_subpart',
'is_sole_proprietor',
'last_updated_date',
'npi_deactivation_date',
'npi_reactivation_date',
'parent_organization_lbn',
'replacement_npi',
'NPI',
'organization_name',
'name_suffix',
'name_prefix',
'first_name',
'middle_name',
'last_name',
'gender.code',
'gender.value',
'credential',
'enumeration_date'}
```

-continued

```
provider_abstract_node.make_abstract_attributes(*provider_attr_keys)
provider_identifier = NodeIdentifier(
   provider_abstract_node,
   provider_abstract_node.get_abstract_attribute('NPI'),
   make_permanent_copy=False)
# Address (provider mailing address and provider practice location)
address_abstract_node = AbstractNode(namespace, 'Address')
address_attr_keys = {
'first_line',
'second_line',
'city_name',
'telephone_no',
'state_code',
'postal_code',
'country_code',
'fax_no',
'telephone_no',
'concatenated_address'}
address_abstract_node.make_abstract_attributes(*address_attr_keys)
address_identifier = NodeIdentifier(
   address_abstract_node,
   address_abstract_node.get_abstract_attribute('concatenated_address'),
   make_permanent_copy=False)
# Specialization
specialization_abstract_node = AbstractNode(namespace, 'Specialization')
specialization_abstract_node.make_abstract_attribute('taxonomy_code')
specialization_identifier = NodeIdentifier(
   specialization_abstract_node,
   specialization_abstract_node.get_abstract_attribute('taxonomy_code'),
   make_permanent_copy=False)
# Credentials
credential_abstract_node = AbstractNode(namespace, 'Credential')
credential_abstract_node.make_abstract_attributes('credential')
credential_identifier = NodeIdentifier(
   credential_abstract_node,
   credential_abstract_node.get_abstract_attribute('credential'),
   make_permanent_copy=False)
# Authorized official:
official_abstract_node = AbstractNode(namespace, 'AuthorizedOfficial')
official_attr_keys = {
'credential',
'first_name',
'middle_name',
'last_name',
'name_prefix',
'name_suffix',
'telephone_no'}
official_abstract_node.make_abstract_attributes(*official_attr_keys)
# AuthorizedOfficial-[:REPRESENTS]->Provider
official_provider_abstract_edge = AbstractEdge(
   official_abstract_node,
   provider_abstract_node,
   relation_type='REPRESENTS')
official_provider_abstract_edge.make_abstract_attribute('title_or_position')
official_provider_subgraph = AbstractSubgraph(
   provider_abstract_node, official_abstract_node,
   official_provider_abstract_edge)
official_identifier = NodeIdentifier(
   official_abstract_node,
   CombineFieldsTransformer(
   provider_abstract_node.get_abstract_attribute('NPI'),
   official_abstract_node.get_abstract_attribute('first_name'),
   official_abstract_node.get_abstract_attribute('last_name')),
make_permanent_copy=False,
subgraph=official_provider_subgraph)
# State
state_abstract_node = AbstractNode(namespace, 'USState')
state_abstract_node.make_abstract_attribute('code')
state_identifier = NodeIdentifier(
   state_abstract_node,
   state_abstract_node.get_abstract_attribute('code'),
   make_permanent_copy=False)
# Edges:
# Provider-[:HAS_CREDENTIALS]-> Credential
provider_credential_abstract_edge = AbstractEdge(
provider_abstract_node,
credential_abstract_node,
relation_type='HAS_CREDENTIALS')
# AuthorizedOfficial-[:HAS_CREDENTIALS]-> Credential
```

-continued

```
official_credential_abstract_edge = AbstractEdge(
   official_abstract_node,
   credential_abstract_node,
   relation_type='HAS_CREDENTIALS')
# Provider-[:MAILING_ADDRESS]-> Address
provider_mailing_address_abstract_edge = AbstractEdge(
   provider_abstract_node,
   address_abstract_node,
   relation_type='MAILING_ADDRESS')
# Provider-[:PRACTICE_LOCATION]-> Address
provider_practice_address_abstract_edge = AbstractEdge(
   provider_abstract_node,
   address_abstract_node,
   relation_type='PRACTICE_LOCATION')
# Provider-[:SPECIALIZES_IN]-> Specialization
provider_specialization_abstract_edge = AbstractEdge(
   provider_abstract_node,
   specialization_abstract_node,
   relation_type='SPECIALIZES_IN')
provider_specialization_abstract_edge.make_abstract_attribute('specialty_
ranking')
# Provider-[:LICENSED_IN]->State
provider_state_abstract_edge = AbstractEdge(
   provider_abstract_node,
   state_abstract_node,
   relation_type='LICENSED_IN')
provider_state_abstract_edge.make_abstract_attribute('license_ranking')
```

Figure 36:
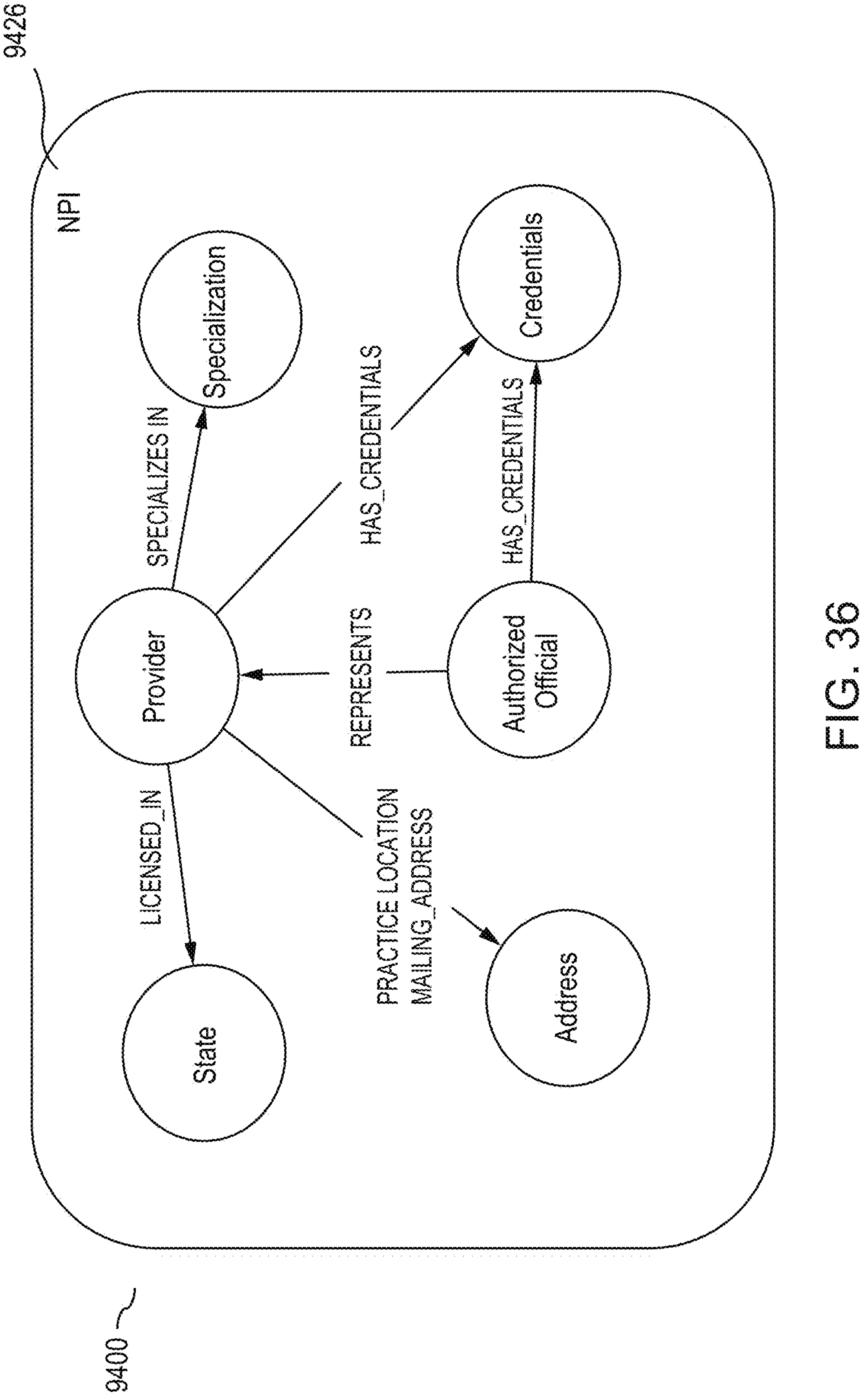
FIG. 36 illustrates an example graph schema for generating a subgraph representing an example public dataset, according to one inventive implementation.

FIG. 36 illustrates an example graph schema 9400, defined by the above descriptor file, for generating a subgraph representing the NPI public dataset in the NPI namespace 9426, according to one inventive implementation. It should be appreciated that FIG. 36 itself is not a subgraph of actual nodes and edges (e.g., as shown in FIGS. 33 and 34) representing the NPI dataset; rather, the graph schema 9400 illustrates node types, edge types, and the particular placement of certain edge types between certain node types. Accordingly, in FIG. 36, the labeled circles do not represent nodes themselves, but rather node types; similarly, the labeled arrows do not represent edges themselves, but rather edge types. The actual subgraph for the NPI dataset is generated by applying the graph schema shown in FIG. 36 to a "cleaned" single file for the NPI dataset. Accordingly, there may be multiple nodes of each of the node types shown in FIG. 36 in a subgraph for the NPI dataset (and, correspondingly, multiple edges of each of the edge types shown in FIG. 36.

More generally, with reference again to FIG. 35, in block 9340 a configuration file (or descriptor file) that defines a graph schema for a given dataset is applied to the cleaned single file for the dataset to generate one or more graph files (in an appropriate graph-specific file format). In block 9350 of FIG. 35, these one or more graph files are in turn imported into a graph database management system to render the subgraph representing the dataset in the corresponding namespace. In one example implementation, with reference again to the subgraph 9150A shown in FIG. 33, the one or more graph files generated by applying the graph schema to the cleaned single file for a given dataset include a "*_nodes.csv" file for each node type (e.g., for the CMSICD10 dataset, a file "disease_nodes.csv" would be generated) and a "*_edges.csv" file for each edge type (e.g., for the CMSICD data set, a file "disease_to_disease.edges.csv" would be generated). These .csv files may be imported, for example, into the Neo4j graph database management system (or another graph database management system) to render the subgraph representing the dataset.

The method 9300 shown in FIG. 35 may be similarly implemented to ingest multiple datasets and generate corresponding subgraphs to be included in an RKG according to the inventive concepts disclosed herein. In some implementations, for a given dataset, the blocks 9310 and 9320 in FIG. 35 may be performed periodically (e.g., once a week, once a month), based at least in part on the dynamic nature of the dataset. Likewise, the blocks 9340 and 9350 in FIG. 35 may be performed periodically (in some cases with the same periodicity as performing blocks 9310 and 9320, but not necessarily with the same periodicity as performing the blocks 9310 and 9320).

Figure 37:
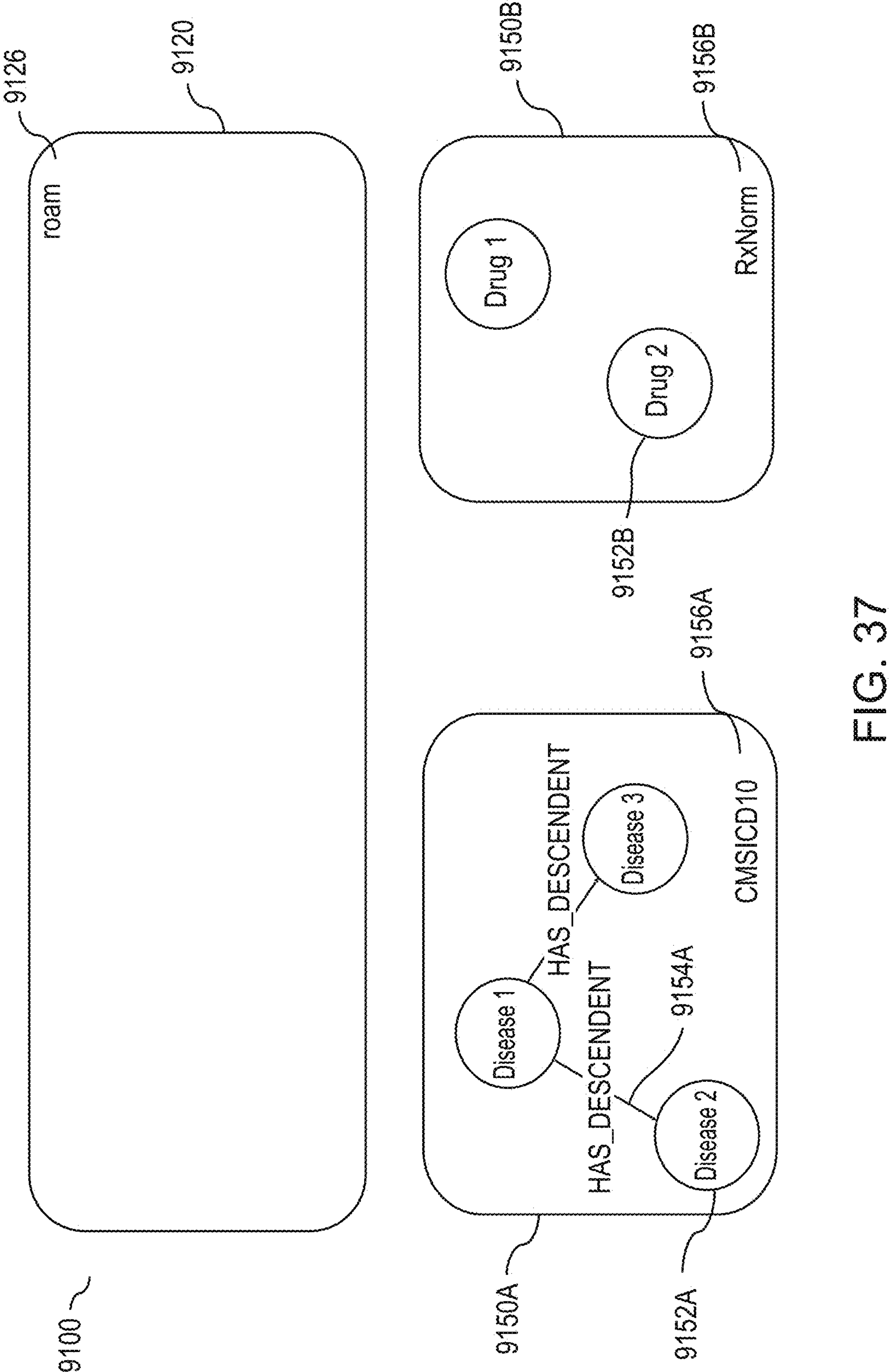
FIG. 37 illustrates the state of graph-building for the example RKG shown in FIG. 33, after the method of FIG. 35 has been applied to two datasets to generate corresponding subgraphs of the RKG, according to one inventive implementation.

Populating the Canonical Layer with Canonical Nodes and Connecting Subgraphs to the Canonical Layer FIG. 37 illustrates the state of graph-building for the RKG 9100 shown in FIG. 33, after the method of FIG. 35 has been applied to the CMSICD10 dataset and the RxNorm dataset. In particular, in FIG. 37, each of the subgraphs 9150A and 9150B is fully rendered in a corresponding isolated namespace, but the canonical layer 9120 is not yet populated and the subgraphs are not yet connected to the canonical layer. Once subgraphs are generated for respective datasets in isolated namespaces of an RKG, the next phases of graph-building involve populating the canonical layer of the RKG with canonical nodes and connecting the subgraphs to the canonical layer.

Figure 38:
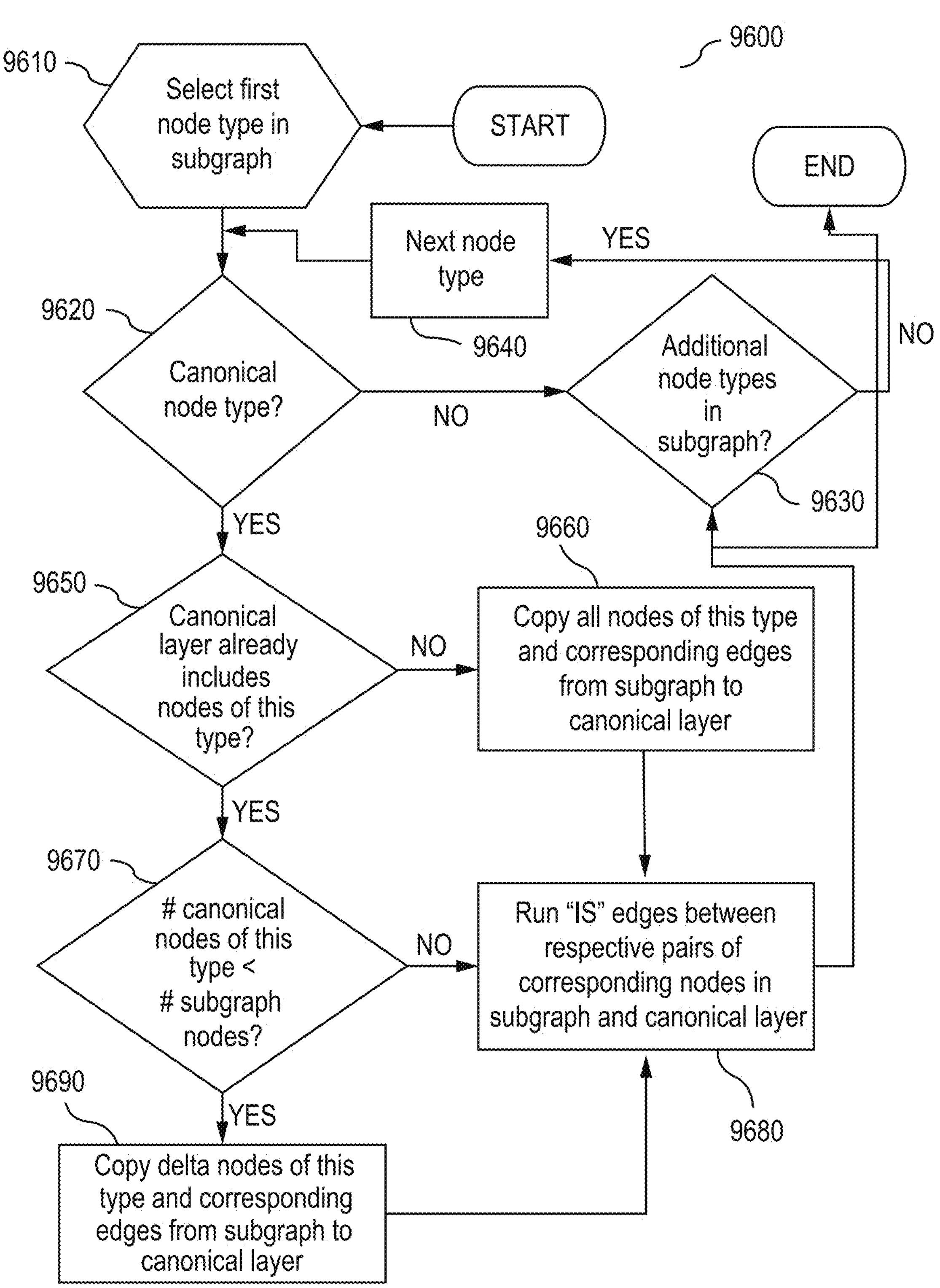
FIG. 38 illustrates an example method for populating a canonical layer of an RKG with canonical nodes and connecting subgraphs of the RKG to the canonical layer, according to one inventive implementation.

FIG. 38 illustrates such a method for populating the canonical layer of the RKG with canonical nodes that are copied from a subgraph representing a dataset and connecting corresponding nodes of the subgraph and the canonical layer with edges of the type "IS" (or edges of substantially similar types to "IS," as discussed above). It should be appreciated that the method of FIG. 38 is performed on a subgraph-by-subgraph basis and may be performed sequentially on a number of subgraphs in succession or contemporaneously on multiple subgraphs.

In block 9610 of FIG. 38, a first node type is selected in the subgraph under consideration; in some implementations this selection may be made arbitrarily. If this first node type is not a canonical node type, as illustrated in blocks 9620, 9630 and 9640 the method then proceeds to the next node type in the subgraph; if there are no more node types remaining for consideration, the method ends. If however the node type presently under consideration is a canonical node type, in block 9650 of FIG. 38 the method considers if there are already nodes of this type in the canonical layer of the RKG. If not, in block 9660 all of the nodes of this type and any edges coupled to these nodes are copied from the subgraph into the canonical layer, and in block 9680 edges of the type "IS" are run between respective pairs of corresponding nodes in the canonical layer and the subgraph. If in block 9650 it is determined that there are already canonical nodes of the type in question in the canonical layer, in block 9670 the method considers if the number of canonical nodes of this type already present in the canonical layer is less than the number of subgraph nodes of this type. If not (i.e., if the set of canonical nodes of the type in question is a superset of the subgraph nodes of the same type), the method proceeds to block 9680 and runs edges of the type "IS" between respective pairs of corresponding nodes in the canonical layer and the subgraph.

In block 9670 of FIG. 38, if the number of canonical nodes of the type in question is less than the number of subgraph nodes of the same type (the set of subgraph nodes of the type in question is a superset of the canonical nodes of this type), then in block 9690 those subgraph nodes of the type in question that are not already in the canonical layer ("delta nodes"), as well as any edges connected to these nodes, are copied into the canonical layer as canonical nodes and edges. In an alternative implementation of block 9690, the entire set of subgraph nodes of the type in question (and their corresponding edges) may be copied into the canonical layer and thereby replace any preexisting canonical nodes of this type. Additionally, in some implementations, the dataset represented by the subgraph under consideration may be particularly identified as a fundamental dataset for this node type (and may replace another previously-designated fundamental dataset for this node type). The method 9600 then proceeds to block 9680 where, as noted above, edges of the type "IS" are run between respective pairs of corresponding nodes in the canonical layer and the subgraph. Once edges of the type "IS" are run between the corresponding nodes of the type in question, the method proceeds to block 9630 to see if there are any remaining node types in the subgraph to consider for possible addition to the canonical layer. The method ends when all node types in the subgraph have been thusly considered.

Figure 39:
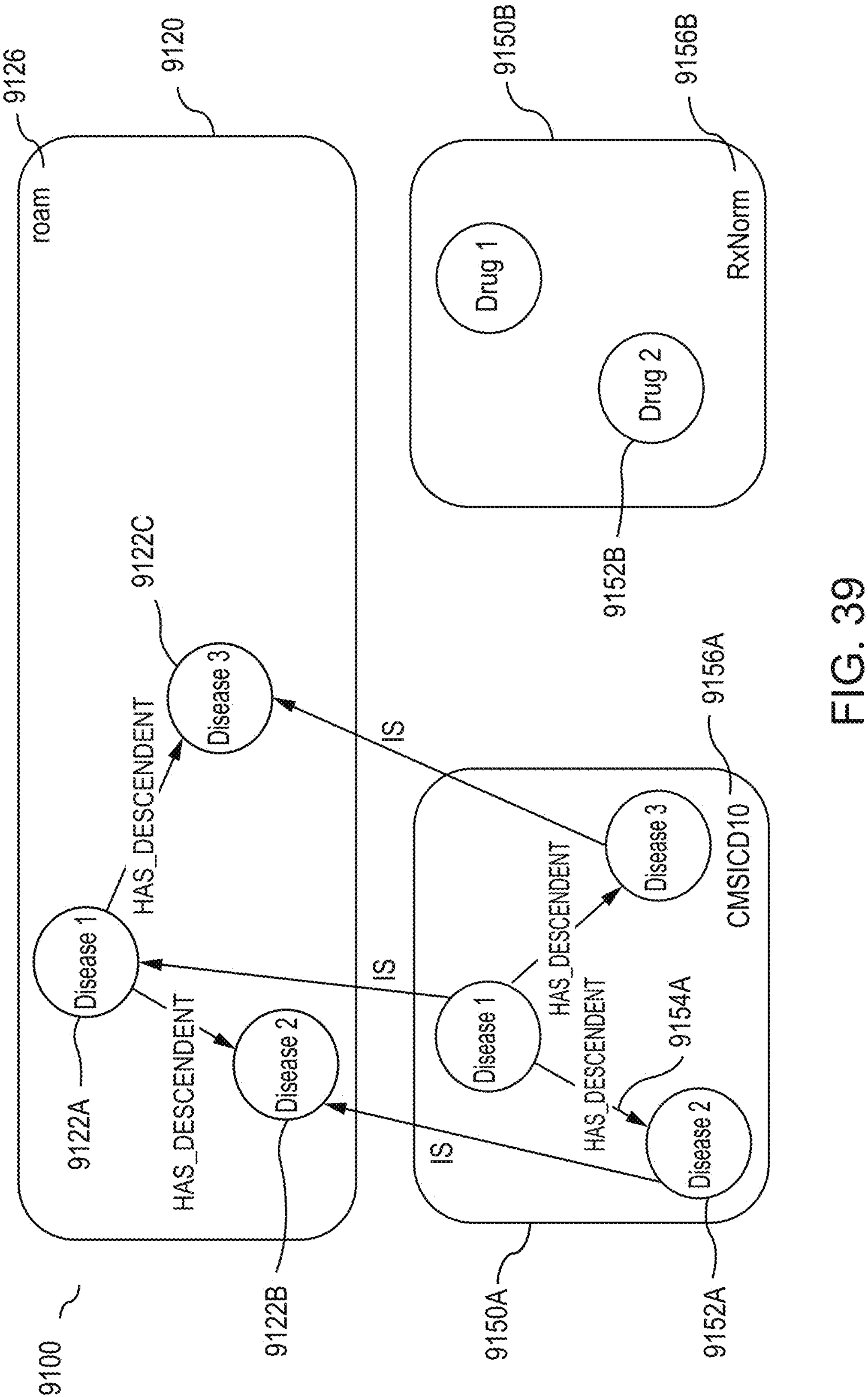
FIG. 39 illustrates the state of graph-building for the example RKG 9100 shown in FIG. 33 after the method of FIG. 38 has been applied to a first subgraph of the RKG, according to one inventive implementation.

To illustrate the application of the method 9600 shown in FIG. 38 in the context of the example RKG 9100 of FIG. 33, FIG. 39 illustrates the state of graph-building for the RKG 100 shown in FIG. 33 after the method of FIG. 38 has been applied to the subgraph 9150A representing the CMSICD10 dataset. Similarly, FIG. 30 illustrates the state of graph-building for the RKG 9100 shown in FIG. 33 after the method of FIG. 38 has been applied to both the subgraph 9150A representing the CMSICD10 dataset and subgraph 9150B representing the RxNorm dataset.

Figure 40:
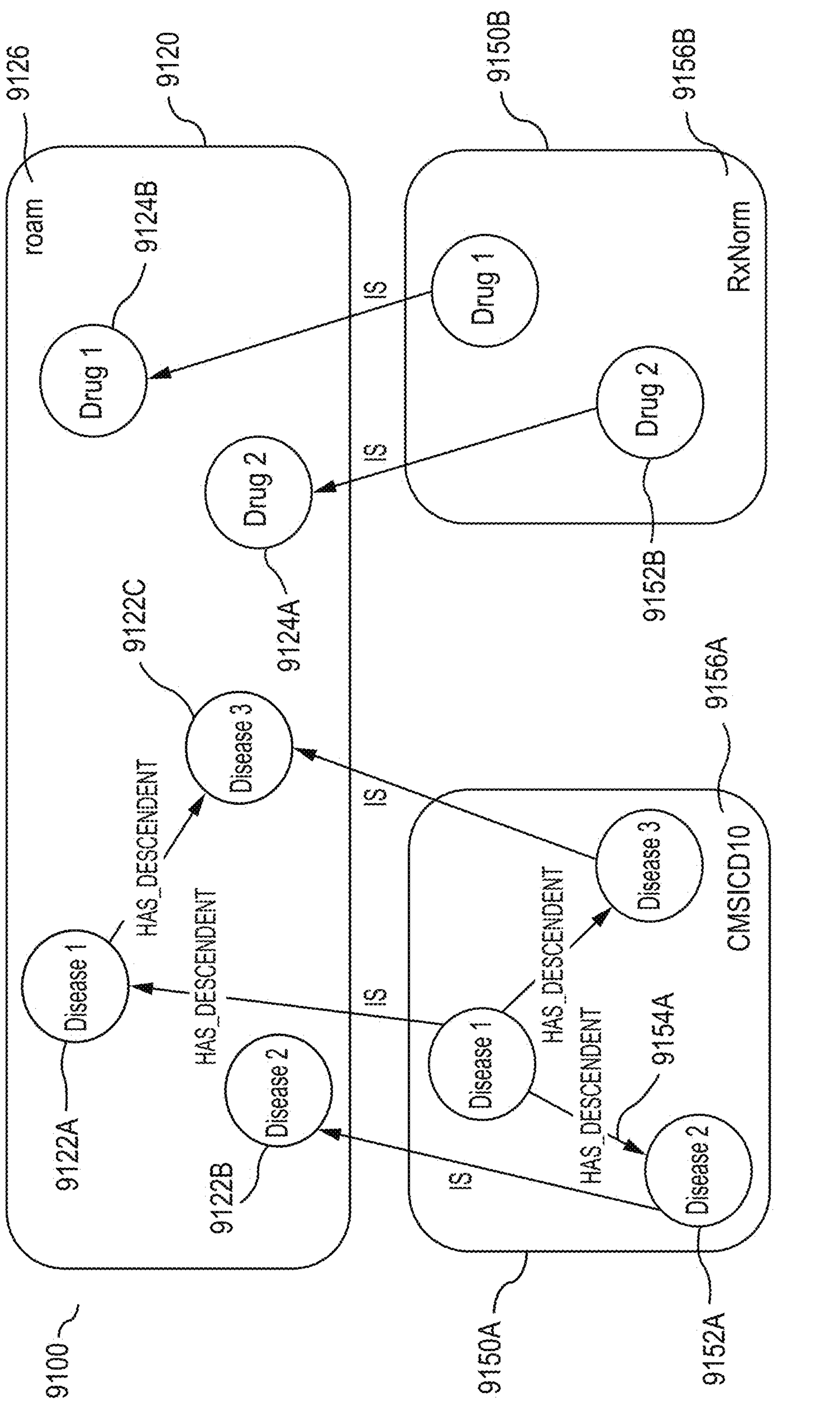
FIG. 40 illustrates the state of graph-building for the example RKG 9100 shown in FIG. 33 after the method of FIG. 38 has been applied to both a first subgraph and a second subgraph of the RKG, according to one inventive implementation.

In the discussion above of FIGS. 38, 39, and 40, the edges that are run between the subgraphs and the canonical layer in these examples may be based on relatively straightforward logic, specifically if the canonical layer is being populated with nodes of particular types for the first time (e.g., based on subgraphs of fundamental datasets). More generally, as noted above, edges may be generated between subgraph nodes and canonical nodes of certain types (or between two canonical nodes) pursuant to defined logic (e.g., in a suitable programming language) based on a variety of criteria. The codification of such logic to definitively generate an edge between two nodes is referred to herein as a "logic-based connector."

For example, a logic-based connector may be defined so as to connect a subgraph node of type X to canonical node of type X with an edge of type "IS" if the respective primary identifiers of the nodes match (e.g., when a subgraph node is copied to the canonical layer). Similarly, such logic may be defined so as to connect a subgraph node of type Y to a canonical node of type Y with an edge of type "IS" if respective attributes A1, A3 and A5 have the same values for the respective nodes (e.g., in some instances in which canonical nodes of the type Y already populate the canonical layer, and a new subgraph is being considered for connection to the canonical layer). In another example relating to connection of canonical nodes, logic for forming certain edges may be defined so as to connect canonical node J of the type "Person" having an attribute "A3-Residence State" with canonical node K of the type "U.S. States" having an attribute "A1-State Name" with an edge of the type "LIVES_IN" if (J, A3=K, A1). Accordingly, a variety of edges between nodes can be generated with certainty based on matching one or more attributes of the respective nodes pursuant to a logic-based connector.

Model-Based Connectors

In another inventive aspect, an edge may be generated between a subgraph node and a canonical node, or between two canonical nodes, based on a trained machine learning (ML) model that predicts, with some degree of certainty, the relationship between the two nodes. ML model-based definitions for generating an edge between two nodes, in the context of an RKG pursuant to the inventive concepts disclosed herein, is referred to as a "model-based connector." In general, the design of a given model-based connector supports the basic decision-making logic "should an edge be created between these two nodes or not?" In various implementations, a model-based connector may be defined (codified) using a suitable programming language (e.g., as discussed above, the Python programming language may be employed) and executed at an appropriate time as part of an overall RKG-building process.

In various aspects, the design of a model-based connector may be situation-based in that it may be tailored to particular node types and available attributes, one or more characteristics of particular datasets, target types of relationships (e.g., desired outcomes) and/or various information derived or inferred from node types other than those for which the edge is generated by the model-based connector. In some examples, a model-based connector may add one or more attributes to one or more of the nodes for which an edge may be generated (e.g., to interpolate missing information about a given subgraph node or canonical node) as a predicate for establishing the relationship between the nodes.

Various types of ML models suitable for purposes of designing a model-based connector according to the inventive concepts herein are known in the relevant arts, examples of which include, but are not limited to, Binary Classification, Multiclass Classification, Linear Regression, Logistic Regression, Decision Tree, Support Vector Machine, Naive Bayes, kNN, K-Means, and Random Forest.

With reference again to the example RKG 9100 shown in a formative state in FIG. 40, after the canonical nodes have preliminarily populated the canonical layer 9120, and respective subgraphs 9150A and 9150B have been connected to the canonical layer pursuant to the method 9600 outlined in FIG. 38, a next phase of graph-building may involve one or more model-based connectors to generate edges between canonical nodes. For example, with reference again to FIG. 33, the two edges of the type "TREATS," one between the node 9124B (roam/Drug/Drug 1) and the node 9122B (roam/Disease/Disease 2), and another between the node 9124A (roam/Drug/Drug 2) and the node 9122C (roam/Disease/Disease 3), may be generated via a model-based connector.

For example, the model-based connector may be designed to add an attribute to each canonical node of the type "Drug" to specify one or more diseases that the drug treats, with some degree of certainty. In some implementations, the model-based connector may add such an attribute to canonical nodes of the type "Drug" based at least in part on information derived or inferred from one or more other datasets (that may or may not be part of the RKG) on which an ML model has been trained. In some implementations, the model-based connector also may add a probability attribute to the nodes of the type "Drug" in connection with the newly-added disease attribute. The logic for the model-based connector may then generate an edge of the type "TREATS" between a given canonical drug node and a given canonical disease node based on matching the model-based disease attribute newly added to the drug node with a corresponding attribute of the disease node. In some implementations, the probability attribute may also (or alternatively) be added as an attribute of the edge of the type "TREATS." The result of applying such a model-based connector as part of a graph-building process, as an additional step following the method outlined in FIG. 38, is illustrated in the example RKG 9100 shown in FIG. 33.

Although the example discussed above illustrates the use of a model-based connector to generate an edge between two canonical nodes, it should be appreciated that model-based connectors may be employed liberally in the graph-building process to generate edges having a wide variety of types between subgraph nodes and canonical nodes, or between canonical nodes. Additionally, given the variety of ML algorithms that may be employed as a basis for a given model-based connector, as well as the range of training data that may be available to such algorithms, it should be appreciated that a wide variety of relationships may be inferred between entities represented by nodes in an RKG, using a model-based connector, to thereby generate edges between nodes with a certain degree of certainty ("confidence").

In another example of a model-based connector, consider a situation in which there are multiple nodes of a certain canonical node type already populating the canonical node layer of an RKG, and each of these nodes has a certain set of attributes. For this example, we consider a canonical node type "roam/Provider" representing various health care practitioners. Also for this example, consider that there are already multiple subgraphs in the RKG having nodes of the type "Provider," each with corresponding attributes and connected to a corresponding canonical node of the type "roam/Provider" via an edge of the type "IS."

Now consider a new dataset for addition to the RKG. Upon initial analysis of the new dataset, it is evident that there are health care professional entities prevalent in the dataset; however, there are no attributes of these entities in the new dataset that would permit exact matching to canonical nodes of the type "roam/Provider" (e.g., pursuant to the method outlined in FIG. 38). In this scenario, a model-based connector may be designed to determine nodes of the type "Provider" in a subgraph representing the new dataset that sufficiently correspond to respective ones of the set of nodes "roam/Provider," and then connect these nodes via an edge of the type "IS" with a corresponding probability attribute (or "confidence" value, e.g., from 0 to 1 inclusive). In one example implementation, the logic for such a model-based connector may be based on training an ML classifier.

To facilitate design of a model-based connector in the above example, the existing RKG prior to addition of the new dataset may be queried (as discussed further below) to extract entity types, entities, and attributes for entities that are deemed to be relevant in some manner to the new dataset, and these may be organized in tabular form. Similarly, early portions of the method 9300 shown in FIG. 35 (e.g., blocks 9310 and 9320) may be performed on the new dataset to generate a single "cleaned" dataset file in a similar tabular form (or the new dataset may be used "as—is" if it is already in an appropriate tabular form). Thus, relevant information extracted from the existing RKG and the new dataset are represented as two tables (e.g., in which the column headers for the respective tables may represent in some manner one or more entity types included in the table, and in which respective rows in each table include values for the entities of the types represented by the column headers). For a given dataset, such tables may include relatively few or several rows, and in some instances hundreds if not thousands of rows. An example of one row for each such table is provided below for purposes of illustration:

Existing RKG

| Last | First | Zip | Affiliation | Specialty |
|---|---|---|---|---|
| Kim | Zoltani | 94304 | Stanford | Dental Surgeon |

New Dataset

| Last | First | Zip | Affiliation | Specialty |
|---|---|---|---|---|
| Kim | Zoltan | 94305 | Stanford Hospital | Dentistry |

Next, the process of designing a model-based connector to connect nodes of a subgraph representing the new dataset to sufficiently corresponding nodes in the canonical layer may employ "active learning." To this end, human annotators would be presented with pairs of entries from each of the two tables and asked to say "Yes, these rows respectively refer to the same person" or "No, these rows respectively refer to different people." Once the human annotators provide a relatively small number of such labels, an ML model (e.g., for a classifier) may be developed for the model-based connector and trained on the initial human annotations. As noted above, there are multiple algorithmic choices for developing such an ML model (e.g., Logistic Regression, Support Vector Machine, Decision Tree). Common to all of these models is the requirement that a feature function be created ("featurization") which is run on raw inputs (in the current example, table rows) to obtain purely numerical representations (e.g., degrees of certainty regarding a possible match). Below is an example of how the two example rows presented above may be "featurized:"

| Identical last names | Identical last initials | Identical first names | Identical first initials | Identical affiliation string | Specialty distance | Geo distance in miles |
|---|---|---|---|---|---|---|
| 1 | 1 | 0 | 1 | 0 | 0.8 | 2 |

In some implementations, the existing RKG itself may be used to build such feature functions. For example, the existing RKG might be used to obtain the 'Specialty distance' values, which indicate how far apart two specialties are in the canonical taxonomy of medical specialties. Similarly, the existing RKG may be useful in getting a distance estimate between two zip codes, in normalizing place and entity names, and in doing more sophisticated name comparisons (e.g., the likelihood of the name Zoltan Kim given the likelihoods of Zoltan as a first name and Kim as a last name).

An ML classifier for the model-based connector may now be trained on the feature representations of the human annotated examples. Fundamentally, this means learning to weight the features in the above table to maximize the likelihood of the human annotated examples. With the model initially trained, it can be used to more strategically select additional rows of the respective tables for the human annotators to label to iterate training cycles. Once the model is performing at an acceptable confidence level, it can then be deployed on the entire new dataset to predict corresponding nodes with sufficient certainty and generate edges of the type "IS" between such pairs of nodes (with the uncertainty recorded as an attribute of the edge of the type "IS"). For the above example, it is likely that a trained model for the model-based connector would say with relatively high confidence that a node in the subgraph representing the Zoltan Kim row in the new dataset identifies the same entity as indicated in the row extracted from roam/Provider; accordingly, the model-based connector would add an edge of the type "IS" between these corresponding nodes in the new dataset and the canonical layer, thereby enriching the RKG with all the information present in the new dataset.

Coordinating the RKG-Building Process

Based on the foregoing discussion on the rudiments of building an RKG according to the inventive concepts disclosed herein, it should be appreciated that RKGs of varying and arbitrary complexity may be built according to these rudiments. For example, an RKG relating to a given domain or domains of interest may be based on several dozens of sizeable datasets from multiple different sources, and thus may include several millions of nodes and edges.

To coordinate and execute the various steps of the methods outlined in FIGS. 3 and 6 for multiple potentially large and complex subgraphs, as well as execute a substantial number of logic-based connectors and model-based connectors, a workflow management system may be employed to define and execute various tasks corresponding to these functions. In general, a "task" is a unit of work corresponding to a particular function relating to graph-building (e.g., "build a subgraph for dataset X," "populate the canonical layer with nodes of type Y from dataset Z," "run model-based connector Q to connect canonical nodes of type R to canonical nodes of type S"). In some implementations, many dozens if not hundreds of such tasks may be defined to build an RKG. As may be appreciated from the discussion above, some of these tasks may be performed contemporaneously (in parallel), while some tasks may depend on the completion of one or more other tasks and thus need to be performed in a particular sequence (in series).

In view of the foregoing, in some example implementations a workflow management system based on Directed Acyclic Graphs (DAGs) for organizing tasks and defining dependencies between tasks is employed to facilitate the process of building an RKG. In particular, one or more DAGs may be employed to schedule tasks that may be done periodically (e.g., see blocks 9310 and 9320 of FIG. 35), run tasks in parallel on multiple computing systems (to reduce execution time for graph-building), and facilitate changes to the RKG and reordering of tasks over time (e.g., as new datasets are considered for expansion of the RKG). One example of such a workflow management system suitable for purposes of RKG building according to the present disclosure is provided by Apache Airflow.

To facilitate the use of DAGs to organize and execute the graph-building process, in another inventive implementation a library of functions and other computational objects (collectively referred to as "graph-building tools") may be created (this library is also referred to herein as "Gryphon"). In one aspect, such a library may be considered a domain-specific programming language (e.g., implemented in Python) to define different "classes" and "objects" (in the sense of object-oriented programming) corresponding to various functions and definitions germane to graph-building (e.g., configuration files or descriptors for subgraph schema; code for logic-based or model-based connectors). In another aspect, with respect to the database management system in which an RKG is created and maintained, the library may be essentially data format-agnostic and database-agnostic. As a DAG executes tasks, it may call on various objects in the library (e.g., via a pointer to a particular object) to execute a particular task.

In one example implementation, a library of such graph-building tools may include a class of objects referred to as "Downloaders," i.e., the set of all files that respectively codify the process of downloading (ingesting) datasets via the Internet to corresponding isolated namespaces in computer storage (e.g., see FIG. 35, block 9310). In this respect, it should be appreciated that there is typically one downloader file in the class "Downloaders" for each dataset to be included in the RKG. Similarly, the library of graph-building tools may include a class of objects referred to as "Importers," i.e., the set of all files that respectively codify the process of creating a single "cleaned" dataset file for each dataset (e.g., see FIG. 35, block 9320). A given downloader file and corresponding importer file may be called upon as a DAG executes one or more tasks directed to the ingestion and cleaning of a given dataset.

Another class of objects in the library of graph-building tools may be referred to as "Descriptors," i.e., the set of all configuration files respectively defining graph schemas for subgraphs representing ingested datasets (e.g., see FIG. 35 block 9330). In this respect, it should again be appreciated that there is typically one configuration file in the class "Descriptors" for each subgraph in an RKG. Another class of objects may be referred to as "Builders," i.e., the set of all files that respectively apply the graph schema defined in a given configuration file in the "Descriptors" class to a corresponding single cleaned dataset file so as to generate one or more graph files representing a subgraph (e.g., see FIG. 35 block 9340). Another class (or individual object) in the library of graph-building tools may be referred to as "RKG_Importer," i.e., a file that codifies the process of importing all subgraphs into isolated namespaces of the RKG (e.g., see block 9350 of FIG. 35), to facilitate subsequent population of canonical nodes and generation of edges between subgraphs and the canonical layer.

Yet another class of objects of particular significance in the library of graph-building tools may be referred to as "Connectors," i.e., the set of all files that codify logic-based connectors and model-based connectors (particularly referred to in the library as MBCs) for populating canonical nodes in the canonical layer and generating edges between subgraphs and the canonical layer of an RKG, as well as edges between canonical nodes in the canonical layer (e.g., see block 9680 of FIG. 38). Given the wide variety of logic-based connectors and model-based connectors that may be employed in an RKG, the number of files/objects in the class "Connectors" does not necessarily correspond to the number of datasets in an RKG (and generally significantly exceeds the number of datasets). Also, it should be appreciated that some connectors are dependent on other connectors being previously executed (e.g., there may be a strict dependency on the order in which certain connectors are run). The various dependencies of running connectors may be facilitated by the manipulation of tasks within a given DAG.

Figure 41:
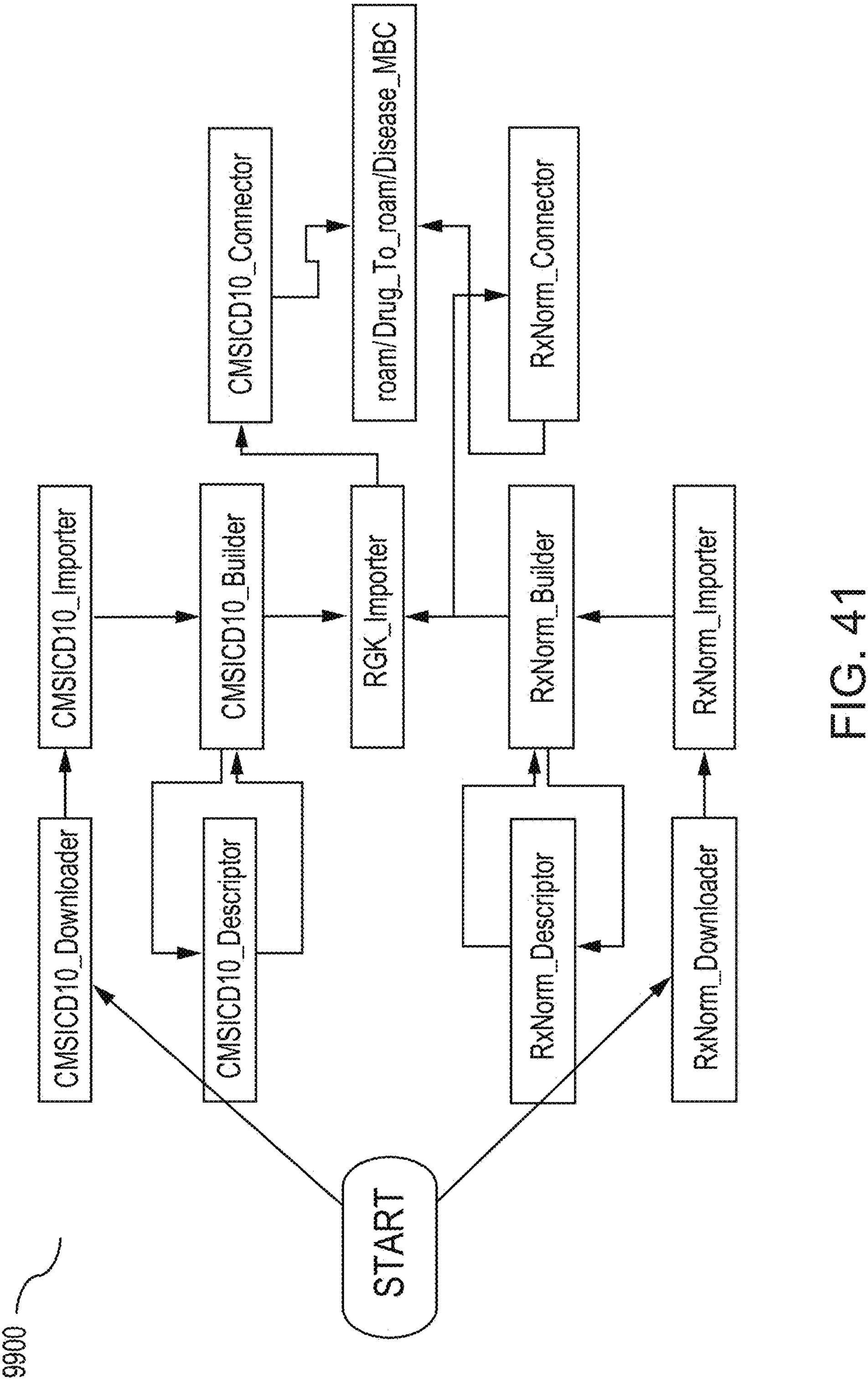
FIG. 41 illustrates an example of a Directed Acyclic Graph (DAG) for building the RKG shown in FIG. 33 using multiple graph-building tools to execute various tasks according to the methods of FIGS. 35 and 38, according to one inventive implementation.

Based on the foregoing example of a library of graph-building tools, FIG. 41 illustrates an example DAG 9900 for building the RKG 9100 shown in FIG. 33, according to one inventive implementation. As may be observed in FIG. 41, some of the tasks shown in the DAG may be executed in parallel (in which respective tasks call on various objects in the library of graph-building tools), while other tasks are executed in a particular sequence. For example, the tasks of downloading and importing datasets, as well as building subgraphs for datasets, may be executed in parallel. Subsequently, all subgraphs are imported into respective isolated namespaces of the RKG via "RKG_Importer." Thereafter, connectors for each subgraph (e.g., to populate canonical nodes of the canonical layer and connect respective pairs of subgraph nodes and canonical nodes with edges of the type "IS") may be run in parallel, after which a model-based connector (MBC) may be executed to generate edges of the type "TREATS" between canonical nodes of the type roam/Drug and canonical nodes of the type roam/Disease.

Querying a Roam Knowledge Graph (RKG)

In some implementations, the process of querying an RKG according to the concepts disclosed herein is dependent, at least in part, on the graph database management system used to create and maintain the RKG.

Cypher Queries

For example, the graph database management system Neo4j employs the "Cypher" declarative query language. An example query of an RKG stored in Neo4j using Cypher is reproduced below. In the RKG for which the query is constructed, there is a subgraph in the namespace "NPI" having nodes of the type "NPI/Provider," and the canonical layer of the RKG includes canonical nodes of the type "roam/HealthcareProfessional," "roam/Geography/Address" and "roam/Specialty/Specialization:"

```
MATCH(p: 'roam/HealthcareProfessional')
  -[:PRACTICE_LOCATION]->(a:
  'roam/Geography/Address'{state_code: 'NY'})
MATCH(p)
  -[:SPECIALIZES_IN]->(s: 'roam/Specialty/Specialization')
MATCH(p)
  -[:IS]-(npi: 'NPI/Provider')
RETURN
  p.first_name AS first_name,
  p.last_name AS last_name,
  p.'gender.code' AS gender,
  a.city_name AS practice_city,
  a.state_code AS practice_state,
  s.code AS specialization_code,
  s.classification AS classification,
  npi.NPI AS NPI,
  npi.credential AS credential
```

The above query codifies the following request: "Find all health care professionals in the RKG who practice in New York state and have a practice specialization, and who are also listed in the NPI public dataset, and return various information about these health care professionals." This query starts a search in the canonical layer of the RKG to identify canonical nodes corresponding to health care professionals (node type p: "roam/HealthcareProfessional"), and continues a search within the canonical layer to identify the canonical node for New York state (a: 'roam/Geography/Address '{state_code: 'NY'}) that is coupled to canonical nodes practitioners via an edge of the type "PRACTICES_LOCATON." The search then continues within the canonical layer to further determine those canonical nodes for health care professionals that are not only coupled to the canonical node for New York state, but are also coupled to canonical nodes corresponding to their respective specializations (s: "roam/Speciality/Specialization") via an edge of the type "SPECIALIZES_IN." Based on the results obtained from the search of the canonical layer, the search responsive to the query then looks in the NPI subgraph for nodes of the type "NPI/Provider" corresponding to only those health care professionals identified in the canonical layer search results (i.e., who practice in New York state and have a specialization).

For each healthcare professional that satisfies the above query, the query extracts certain attributes from the respective nodes identified in the search of the graph to provide a results set. In particular, pursuant to the RETURN declarations specified in the query, some attributes are gathered from the canonical nodes of type "p" ("roam/Healthcare-Professional"), some attributes are gathered from the canonical nodes of type "a" ("roam/Geography/Address"), some attributes are gathered from the canonical nodes of type "s" ("roam/Specialty/Specialization"), and some attributes are gathered from the nodes in the NPI subgraph of the type "npi" ("NPI/Provider"). In the present query example, the query also dictates that the result is presented as a spreadsheet with column headers indicated by the RETURN declarations.

Given the size of the NPI dataset, the spreadsheet for the result set corresponding to the Cypter query example above includes hundreds of thousands of rows; a short illustrative excerpt from this spreadsheet is reproduced below:

| first_name | last_name | gender | practice_city | practice_state | specialization_code | classification | NPI | credential |
|---|---|---|---|---|---|---|---|---|
| MAY | KYI | F | BROOKLYN | NY | 390200000X | Student in an Organized Health Care Education/ Training Program | 1588085567 | M.D |
| ANUDEEPA | SHARMA | F | BROOKLYN | NY | 282NC2000X | General Acute Care Hospital | 1902225428 | |
| ANUDEEPA | SHARMA | F | BROOKLYN | NY | 261QM0855X | Clinic/Center | 1902225428 | |
| ANUDEEPA | SHARMA | F | BROOKLYN | NY | 261Q00000X | Clinic/Center | 1902225428 | |
| PRABHAVATHI | GUMMALLA | F | BROOKLYN | NY | 282NC2000X | General Acute Care Hospital | 1750700852 | M.D |
| O | RAFFO | M | COOPERSTOWN | NY | 207L00000X | Anesthesiology | 1134108244 | M.D. |
| HARISH RAI | SEETHA RAMMOHAN | M | COOPERSTOWN | NY | 207RC0000X | Internal Medicine | 1497082697 | MD, MRCP |
| HERBERT | MARX | M | COOPERSTOWN | NY | 207RC0000X | Internal Medicine | 1164641254 | M.D. |
| AMIRA | ALFIL | F | BROOKLYN | NY | 390200000X | Student in an Organized Health Care Education/ Training Program | 1285045120 | MD, MPH |
| YELVA | LYNFIELD | F | BROOKLYN | NY | 207N00000X | Dermatology | 1194767855 | MD |
| THERESE | MALCOLM | F | BROOKLYN | NY | 207V00000X | Obstetrics & Gynecology | 1558304246 | |
| JOHANNE | THOMAS | F | BROOKLYN | NY | 207L00000X | Anesthesiology | 1134162449 | MD |
| MICHAEL | PITEM | M | BROOKLYN | NY | 2084N0400X | Psychiatry & Neurology | 1225140155 | |
| ROBERT | SPATZ | M | BROOKLYN | NY | 207L00000X | Anesthesiology | 1316988421 | MD |
| MYRON | SOKAL | M | BROOKLYN | NY | 2080N0001X | Pediatrics | 1144263856 | |
| ARUN | KRISHNAN | M | BROOKLYN | NY | 390200000X | Student in an Organized Health Care Education/ Training Program | 1790198265 | |

Semantic Parsing Engine

In other example implementations, a "semantic parsing engine" may be employed to formulate queries of an RKG.

In general, a semantic parsing engine according to the inventive concepts disclosed herein provides a mapping from relatively straightforward English language questions to graph queries (e.g., in Cypher). Each query implicitly identifies a "path" through the graph (as discussed above in connection with the Cypher example query); at the same time, the interactive natural language search capability provided by the semantic parsing engine allows users to pose sophisticated queries in English and receive multifaceted structured answers in response.

Semantic parsing engine is graph-backed in the sense that its grammar and semantic concepts are derived automatically from the graph schema, which is also used to guide the user in formulating and modifying natural English queries in a way that facilitates knowledge discovery. This provides a superior search experience compared to raw database queries.

An enormous amount of U.S. health data has been made available for public over the last few years. Taken together, these datasets have the potential to provide a comprehensive picture of the healthcare domain: drugs, procedures, diseases, providers, and so forth. Even if patient-level data is missing, because of privacy considerations, census and survey data can still support analyses based on fine-grained demographics.

An approach to developing semantic parsers over large health knowledge graphs (HKGs) derived from these public datasets is presented herein. These semantic parsers are graph-backed: the schema for the target graph is used to define the core space of entities, entity-types, and relations; it provides the initial seed sets for defining the semantic lexicon; and it helps delimit the space of rules for syntactic and semantic combination Thus, very large and complex grammars are easily instantiated, addressing one of the major bottlenecks for semantic parsing at scale. The graph schema also improves the interface: it feeds a front-end tool for guiding the user in writing English queries and modifying them in ways that facilitate intuitive discovery of the graph's contents.

A use case for the semantic parser can be natural language search into health knowledge graphs. The alternative is a database query language, which can be cumbersome even for experts and which puts most information out of reach for regular users. Natural language search can remove these obstacles.

The public health datasets under consideration here are not released by a single data source using a consistent set of identifiers. Rather, each dataset presents a partial, potentially biased view of the world, the union of all the information in them is likely to be inconsistent, and establishing even simple links between entities often must be cast as a model-based inference under uncertainty.

In this example, on graph-backed semantic parsers, a small subset of public health datasets was selected that can be assembled into a connected graph with high confidence. The approach disclosed herein can be extended easily to vastly larger graphs created with more complex statistical methods. However, the subset has been used to shine a light on the parser's accuracy and coverage.

Figure 42:
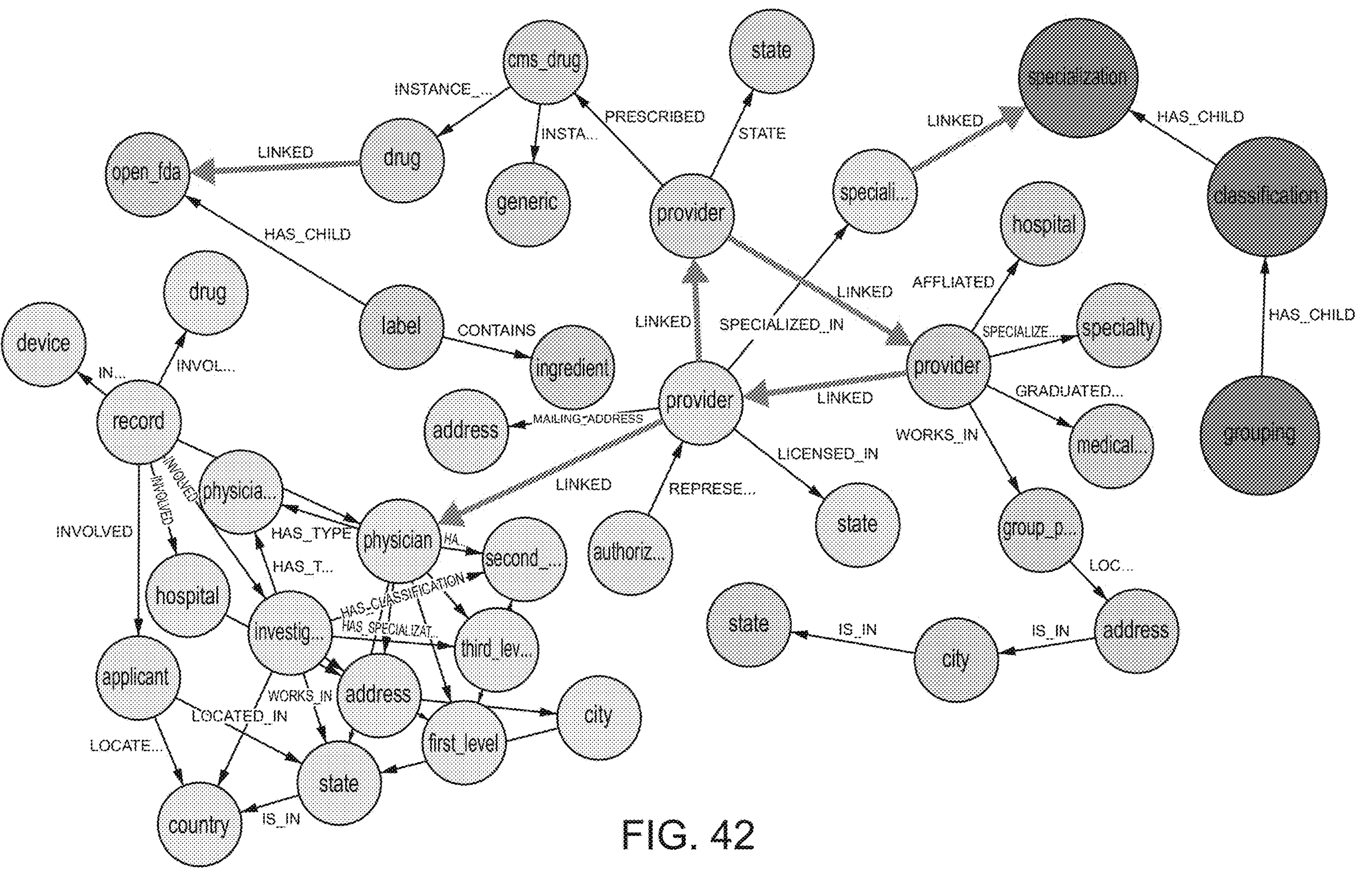
FIG. 42 illustrate an example "health knowledge graph" to demonstrate inventive concepts relating to a semantic parsing engine for querying RKGs, according to one inventive implementation.

The six datasets that have been selected are summarized in table 1 (below). They are united thematically around physicians and their prescribing behavior. FIG. 42 depict the node and edge spaces of the resulting graph. For the most part, these are determined by the structure of the underlying databases.

TABLE 1

| Dataset | Color in FIG. 42 | Description |
|---|---|---|
| National Provider Identifier | Aqua | Registry of healthcare providers |
| CMS Physician Compare | Sky blue | Data on physicians and their practices |
| CMS Open Payments Research | Grey | Research support by manufacturers |
| Healthcare Taxonomy | Cerulean | Three-level classification of medical specialties |
| CMS Prescriptions | Sage | Prescriptions written under Medicare Part D |
| FDA Drug Labels | Olive | Drugs and their associated regulated metadata |

The edges were added to connect these isolated subgraphs and include the word "Linked". These edges are summarized here: NPI ids connect NPI, CMS Physician Compare, and CMS Prescriptions via providers; taxonomy codes connect the NPI with the Healthcare Taxonomy; brand and generic names connect CMS Prescriptions to FDA Drug Labels via drugs; the CMS Open Payments Research dataset, unlike CMS Prescriptions, does not contain NPI ids, so a log-linear classifier was trained using the Dedupe package, matching 4,263 NPI providers with high confidence. The resulting graph is instantiated in Neo4j, and has 4.6 million nodes and 21.2 million edges.

The Semantic Parsing Engine

Figure 43:
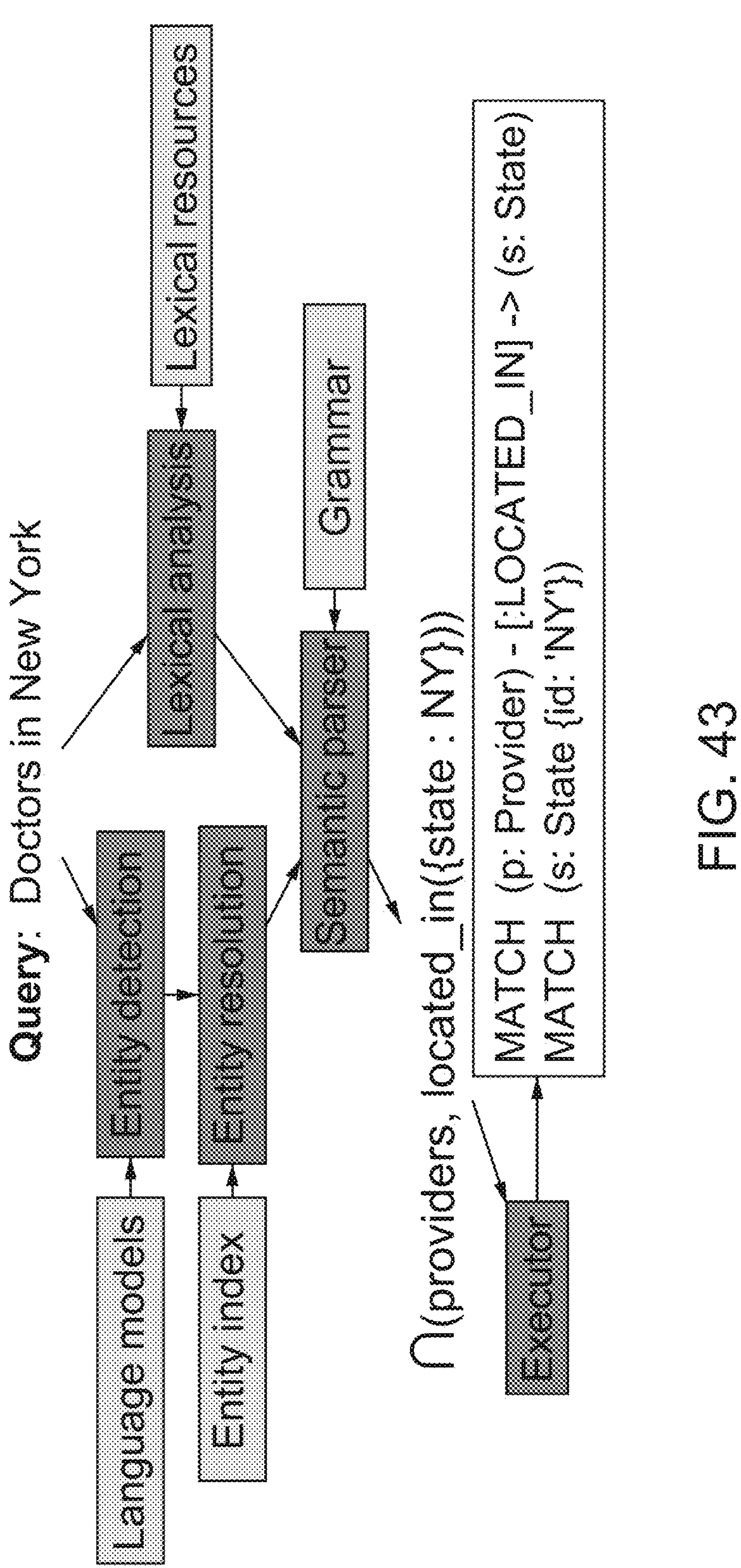
FIG. 43 illustrates a semantic parsing architecture for a semantic parsing engine, according to one inventive implementation.

The semantic parsing engine maps English texts to statements in the declarative Neo4j query language Cypher. FIG. 43 depicts the architecture. The boxes namely "Language models," "Entity index," "Lexical resources," and "Grammar" highlight the numerous ways in which the system is defined by its underlying graph. The language models used for entity detection are trained on 'name'-type attributes of nodes, and resolving those entities is graph-backed: the 'Entity index' is automatically created from the database and provides fast look-up. The 'Lexical analysis' step is similarly graph-backed: node and edge type-names provide the core lexicon, which can then be expand using Wiktionary, WordNet, and heuristic morphological expansion.

The grammar is the most important area of graph-backing; whereas entity and entity-type lists might be obtainable directly from health data resources, semantic grammars are intricate and specialized. Creating and maintaining them is a massive under-taking, and often can be done separately for each database. To avoid this bottleneck, the graph schema can define majority of the grammar rules.

For instance, where the schema contains (Person) → Person Works-in → (Location) the syntax rule PERSON → LOCATION PERSON and semantic rule ∩(Works-in {0}, {1}) can be created. Since relations that are intuitively direct sometimes correspond to long paths in the graph, BRIDGING CONCEPT terms are additionally allowed in the logical forms that have no syntactic realization but establish the desired semantic links, equivalently graph paths. The grammar for the example disclosed herein has 1,786 rules.

Figure 44A:
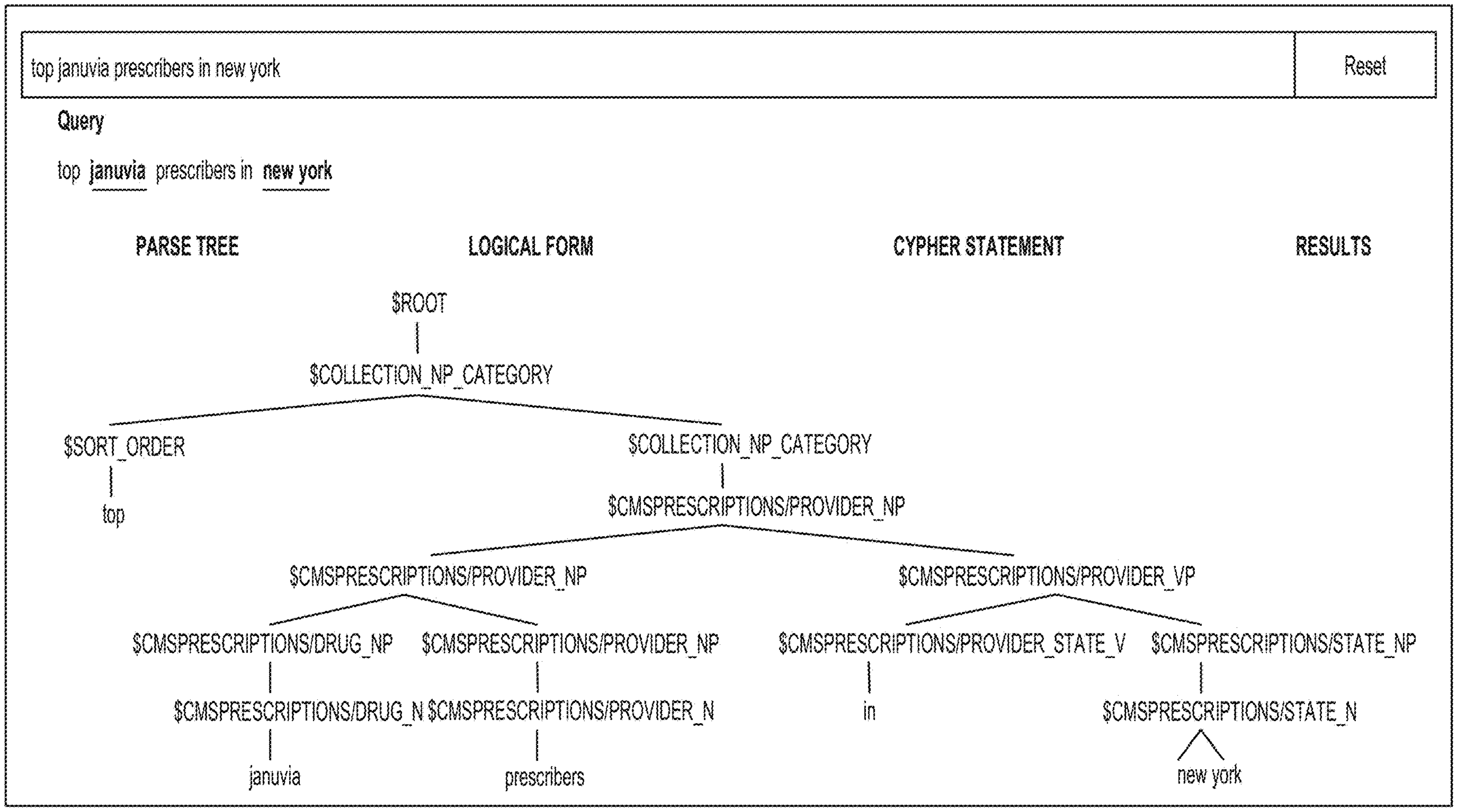
FIG. 44A illustrates an example of a syntactic structure generated by a semantic parsing engine, according to one inventive implementation.
Figure 44B:
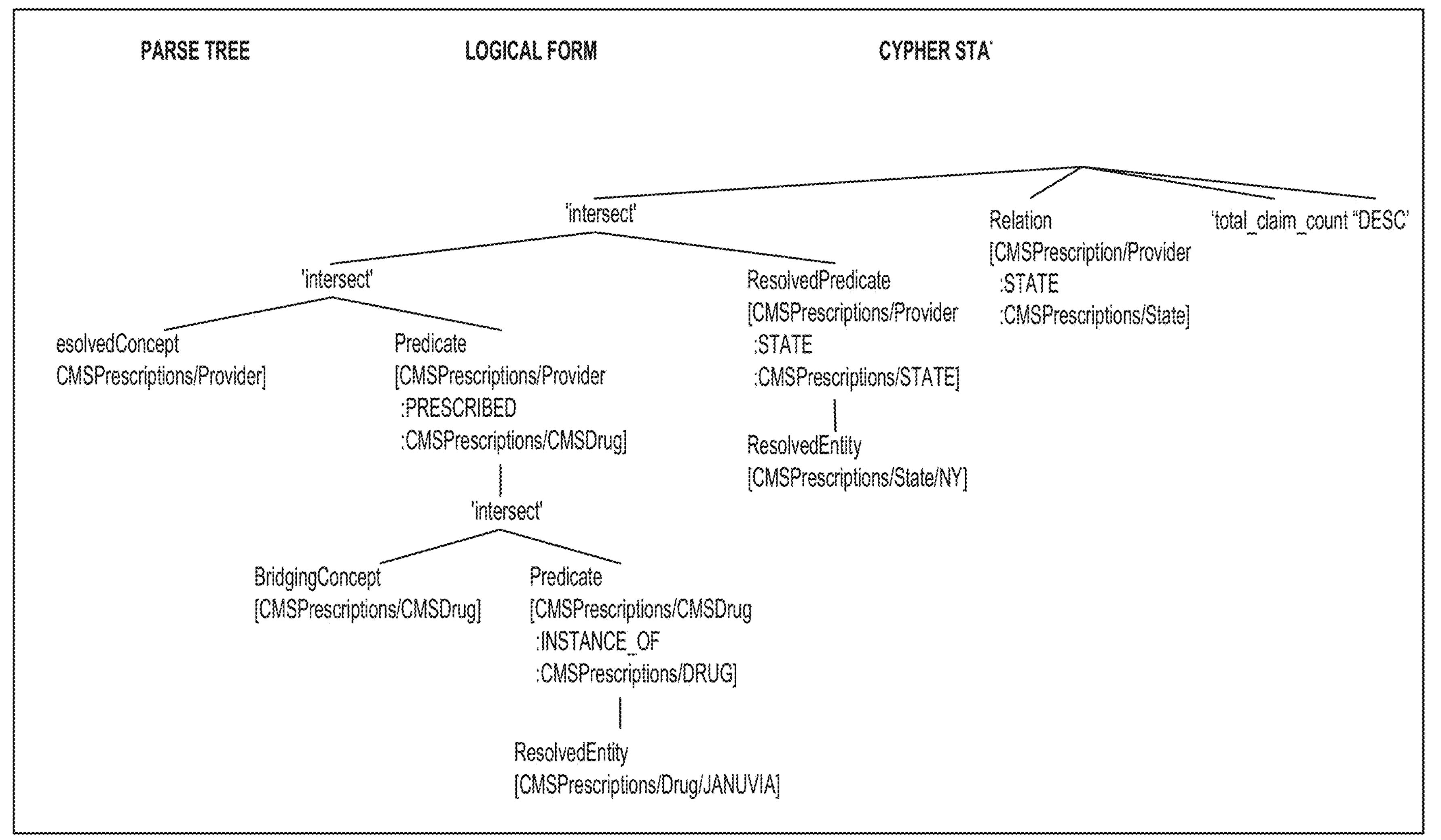
FIG. 44B illustrates an example of a logical form generated by a semantic parsing engine, according to one inventive implementation.

FIGS. 44A-44C illustrate these concepts with partial screenshots of the system's developer view, which exposes the syntax, logical form, and resulting Cypher query for the user's input (along with the database results as a table, not show here). The example is top Januvia prescribers in New York. This query involves three uses of the intersect operator as well as one use of sorted, triggered by the superlative modifier top. Because the CMS Prescriptions sub-graph uses internal 'cms drug' nodes (seen near the top of FIG. 42), a BRIDGINGCONCEPT is triggered to relate provider to drug in the expected way. Where the engine is unable to generate a complete parse, it backs off a search strategy that looks for valid paths in the HKG that include the detected entities and entity types.

Figure 45:
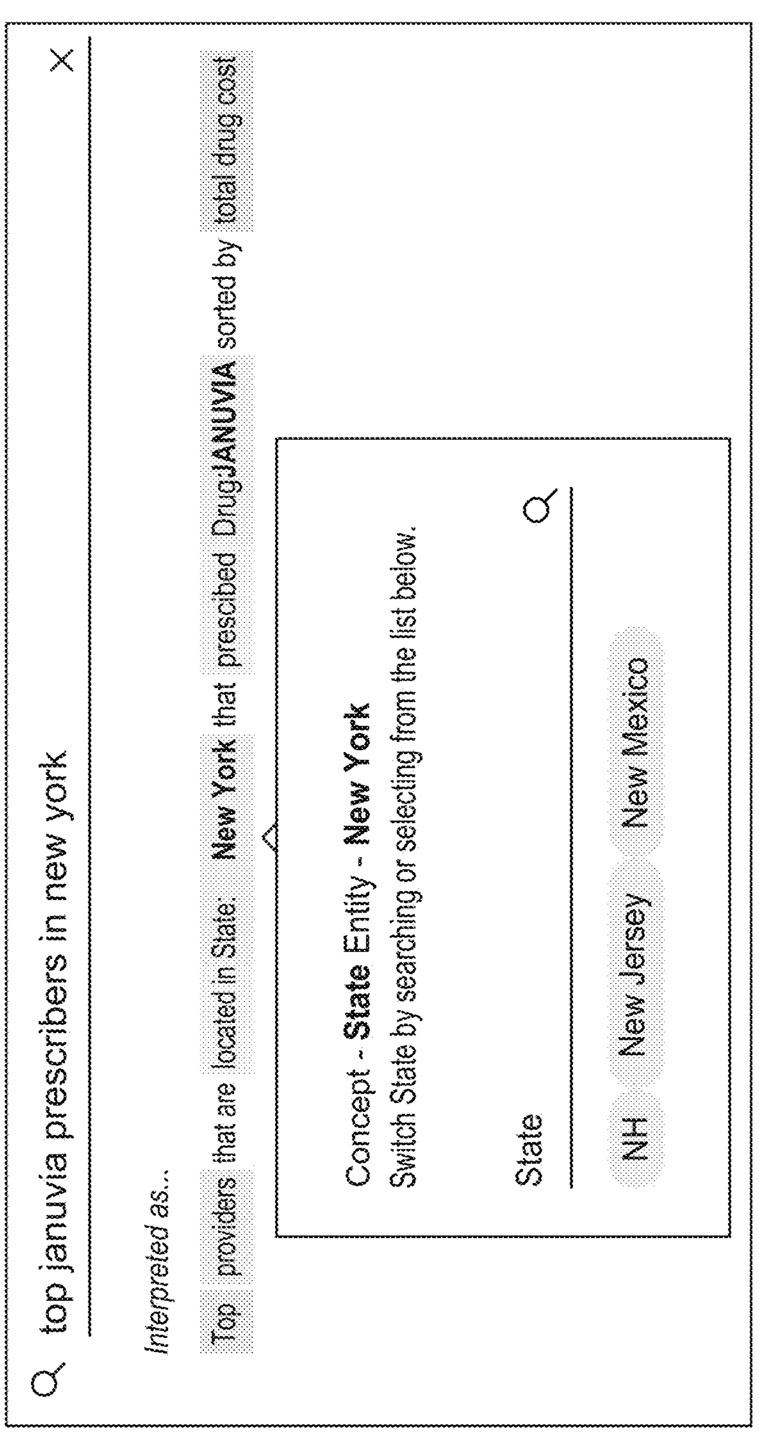
FIG. 45 illustrates an example user interface for a semantic parsing engine showing query expansion and modification, according to one inventive implementation.

The graph is also essential to the user interface. In general, a user's query will reflect a general question. The query is an attempt to sharpen that question in pursuit of actionable intelligence. Presenting the query's results in isolation often doesn't do much to serve this goal; the more the search engine's response can reveal about the underlying graph, the more useful it is. To achieve this, the graph schema can be relied on. FIG. 45 is a snapshot of the user interface that shows how this is done. For any entity-type ("concept") or relation in the query, the user can click on it to see alternatives to it from the graph, as determined by the entity types and graph structure. In FIG. 45, the user has clicked on a state, and the interface has suggested other states that could be put in that position, also giving guidance on how they can be typed in and providing a free text field for making other substitutions. This facilitates rapid query exploration, with the interface accumulating the results for high-level comparisons.

CONCLUSION

All parameters, dimensions, materials, and configurations described herein are meant to be exemplary and that the actual parameters, dimensions, materials, and/or configurations will depend upon the specific application or applications for which the inventive teachings is/are used. It is to be understood that the foregoing embodiments are presented primarily by way of example and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in multiple ways. For example, embodiments may be implemented using hardware, software or a combination thereof. When implemented in software, the software code can be executed on a suitable processor or collection of processors, whether provided in a single computer or distributed among multiple computers.

Further, it should be appreciated that a computer may be embodied in a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in a suitable form, including a local area network or a wide area network, such as an enterprise network, and intelligent network (IN) or the Internet. Such networks may be based on a suitable technology and may operate according to a suitable protocol and may include wireless networks, wired networks or fiber optic networks.

The various methods or processes outlined herein may be coded as software that is executable on one or more processors that employ a suitable operating systems or platform. Additionally, such software may be written using one or more suitable programming languages and/or programming or scripting tools, and also may be compiled as executable machine language code or intermediate code that is executed on a framework or virtual machine. Some implementations may specifically employ one or more of a particular operating system or platform and a particular programming language and/or scripting tool to facilitate execution.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

The invention claimed is:

1. At least one computer, configured for computerized access to at least one dataset and for automating extraction of knowledge from unstructured data, wherein the at least one computer is configured to:

- execute a natural language processing model on a first collection of documents comprising a subset of documents in the dataset to associate metadata with spans in the documents of the first collection, the associated metadata indicating entities and relationships between entities based on an annotation scheme;
- identify corrections to the metadata associated with spans of a document in the first collection by the natural language processing model;
- change or delete metadata applied to one or more documents in the first collection of documents based on the identified corrections;
- retrain the natural language processing model based at least in part on metadata as changed or deleted associated with documents in the first collection of documents;
- until a stop condition is reached, with a collection of documents in place of the first collection of documents, iteratively repeating the act of executing a natural language processing model with the retrained natural language processing model and the acts of identifying corrections, changing or deleting metadata, and retraining the natural language processing model;

executing the natural language processing model, as retrained when the stop condition is reached, on a plurality of documents in the dataset to associate metadata with spans of text indicating entities and relationships between entities; and training an AI system using at least the plurality of documents in the dataset and the associated metadata.

2. The at least one computer of claim 1, wherein the at least one computer is further configured to:

associate an uncertainty with the metadata associated with spans in the documents; and select the one or more documents based on the uncertainty.

3. The at least one computer of claim 1, wherein identify corrections to the metadata associated with spans of a document in the first collection by the natural language processing model comprises identifying differences between the metadata associated with spans of the document by the natural language processing model and by at least one other annotator.

4. The at least one computer of claim 1, wherein at least one dataset comprises a plurality of datasets in the healthcare domain.

5. The at least one computer of claim 1, wherein:

identifying corrections to the metadata comprises displaying a document in a user interface with visual indications of metadata associated with one or more spans within the document, and the user interface comprises controls for receiving user input changing or deleting the metadata.

6. The at least one computer of claim 5, wherein:

displaying the document in the user interface comprises displaying the document with a probability value representative of the association between the metadata and a span of the one or more spans.

7. The at least one computer of claim 1, wherein, for each iteration of executing a natural language processing model, the collection of documents comprises documents in a collection used in a prior iteration for which associated metadata was changed or deleted plus additional documents that were not in the collection used in the prior iteration.

8. At least one non-transitory computer-readable medium encoded with processor-executable instructions that, when executed by at least one processor configured for computerized access to at least one dataset, perform a method for automating extraction of knowledge from unstructured data, the method comprising:

executing a natural language processing model on a first collection of documents comprising a subset of documents in the dataset to associate metadata with spans in the documents of the first collection, the associated metadata indicating entities and relationships between entities;

identifying corrections to the metadata associated with spans of a document in the first collection by the natural language processing model;

changing or deleting metadata applied to one or more documents in the first collection of documents based on the identified corrections;

retraining the natural language processing model based at least in part on metadata as changed or deleted associated with documents in the first collection of documents;

until a stop condition is reached, with a collection of documents in place of the first collection of documents, iteratively repeating the act of executing a natural language processing model with the retrained natural language processing model and the acts of identifying corrections, changing or deleting metadata, and retraining the natural language processing model; and executing the natural language processing model, as retrained when the stop condition is reached, on a plurality of documents in the dataset to associate metadata with spans of text indicating entities and relationships between entities.

9. The at least one non-transitory computer-readable medium of claim 8, wherein the method further comprises:

constructing a knowledge graph based on the metadata associated with the plurality of documents by executing the natural language processing model, as retrained when the stop condition is reached.

10. The at least one non-transitory computer-readable medium of claim 8, wherein the method further comprises:

training an AI system using at least the plurality of documents in the dataset and the associated metadata; and using the trained AI system to predict an adverse event associated with a drug.

11. The at least one non-transitory computer-readable medium of claim 8, wherein the method further comprises:

associating an uncertainty with the metadata associated with spans in the documents; and selecting the one or more documents based on the uncertainty.

12. The at least one non-transitory computer-readable medium of claim 8, wherein the method comprises: performing the method on a plurality of natural language processing models in a library of natural language processing models.

13. The at least one non-transitory computer-readable medium of claim 8, wherein the natural language processing model executed on the first collection of documents is a pre-existing natural language processing model.

14. The at least one non-transitory computer-readable medium of claim 8, wherein the method further comprises:

associating an uncertainty with the metadata associated with spans in the documents;

and selecting the one or more documents based on the uncertainty.

15. A method for automating extraction of knowledge from unstructured data in at least one dataset, the method comprising:

executing a natural language processing model on a first collection of documents comprising a subset of documents in the dataset to associate metadata with spans in the documents of the first collection, the associated metadata indicating entities and relationships between entities;

identifying corrections to the metadata associated with spans of a document in the first collection by the natural language processing model;

changing or deleting metadata applied to one or more documents in the first collection of documents based on the identified corrections;

retraining the natural language processing model based at least in part on metadata as changed or deleted associated with documents in the first collection of documents;

until a stop condition is reached, with a collection of documents in place of the first collection of documents, iteratively repeating the act of executing a natural language processing model with the retrained natural language processing model and the acts of identifying corrections, changing or deleting metadata, and retraining the natural language processing model; and executing the natural language processing model, as retrained when the stop condition is reached, on a plurality of documents in the dataset to associate metadata with spans of text indicating entities and relationships between entities.

16. The method of claim 15, wherein executing the natural language processing model, as retrained when the stop condition is reached, on a plurality of documents in the dataset to associate metadata with spans of text indicating entities and relationships between entities comprises generating a training dataset for a Machine Learning process.

17. The method of claim 16, wherein:

the dataset is a first dataset in a first domain;

the method further comprises: training a further natural language processing model with the training dataset; and executing the further natural language processing model on a second dataset in the first domain.

18. The method of claim 16, wherein changing or deleting metadata applied to one or more documents comprises receiving user input indicating a change or deletion of the metadata.

19. The method of claim 15, wherein:

the natural language processing model is a first natural language processing model;

and the method further comprises training at least a second natural language processing model, wherein the first natural language processing model is configured to identify entities of a first type and the second natural language processing model is configured to identify entities of a second type, different than the first type.

20. The method of claim 15, wherein the method comprises: selecting the collection of documents for multiple iterations such that a larger collection is selected in each successive iteration.

* * * * *